(12) United States Patent
Andreev et al.

(10) Patent No.: US 12,297,257 B2
(45) Date of Patent: *May 13, 2025

(54) MULTISPECIFIC ANTIGEN-BINDING MOLECULES AND USES THEREOF

(71) Applicant: Regeneron Pharmaceuticals, Inc., Tarrytown, NY (US)

(72) Inventors: Julian Andreev, Sleepy Hollow, NY (US); Nithya Thambi, Furlong, PA (US); Frank Delfino, Poughquag, NY (US); Joel Martin, Putnam Valley, NY (US); Gavin Thurston, Briarcliff Manor, NY (US); Katherine Cygnar, New York, NY (US); Nicholas Papadopoulos, The Woodlands, TX (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 903 days.

This patent is subject to a terminal disclaimer.

(21) Appl. No.: 17/483,588

(22) Filed: Sep. 23, 2021

(65) Prior Publication Data

US 2022/0008548 A1     Jan. 13, 2022

Related U.S. Application Data

(63) Continuation of application No. 15/202,822, filed on Jul. 6, 2016, now Pat. No. 11,129,903.

(60) Provisional application No. 62/347,179, filed on Jun. 8, 2016, provisional application No. 62/328,900, filed
(Continued)

(51) Int. Cl.
| | | |
|---|---|---|
| C07K 16/12 | (2006.01) | |
| A61K 39/00 | (2006.01) | |
| A61K 47/68 | (2017.01) | |
| A61P 35/00 | (2006.01) | |
| C07K 14/47 | (2006.01) | |
| C07K 16/18 | (2006.01) | |
| C07K 16/22 | (2006.01) | |
| C07K 16/28 | (2006.01) | |
| C07K 16/30 | (2006.01) | |
| C07K 16/32 | (2006.01) | |

(Continued)

(52) U.S. Cl.
CPC .... *C07K 16/1203* (2013.01); *A61K 47/68033* (2023.08); *A61K 47/6849* (2017.08); *A61K 47/6851* (2017.08); *A61K 47/6855* (2017.08); *A61K 47/6879* (2017.08); *A61P 35/00* (2018.01); *C07K 14/4702* (2013.01); *C07K 16/18* (2013.01); *C07K 16/22* (2013.01); *C07K 16/28* (2013.01); *C07K 16/2833* (2013.01); *C07K 16/2866* (2013.01); *C07K 16/2869* (2013.01); *C07K 16/2896* (2013.01); *C07K 16/30* (2013.01); *C07K 16/32* (2013.01); *C07K 16/468* (2013.01); *C12N 9/6454* (2013.01); *A61K 2039/507* (2013.01); *A61K 2039/572* (2013.01); *C07K 2317/21* (2013.01); *C07K 2317/31* (2013.01); *C07K 2317/35* (2013.01); *C07K 2317/76* (2013.01); *C07K 2317/77* (2013.01); *C07K 2319/00* (2013.01); *C07K 2319/30* (2013.01)

(58) Field of Classification Search
CPC .............. A61K 47/6879; C07K 16/468; C07K 2317/31; C07K 2317/77
See application file for complete search history.

(56) References Cited

U.S. PATENT DOCUMENTS

| | | |
|---|---|---|
| 4,444,878 A | 4/1984 | Paulus |
| 4,975,278 A | 12/1990 | Senter et al. |
| 5,030,717 A | 7/1991 | Tramontano et al. |

(Continued)

FOREIGN PATENT DOCUMENTS

| | | |
|---|---|---|
| KR | 10-2017-0010896 | 2/2017 |
| WO | 1998/016254 A1 | 4/1998 |

(Continued)

OTHER PUBLICATIONS

Hasan et al., Expert Opinion on Therapeutic Targets, 2011, vol. 15, pp. 1211-1225 (Year: 2011).*

(Continued)

*Primary Examiner* — Karen A. Canella
(74) *Attorney, Agent, or Firm* — Alston & Bird LLP

(57) ABSTRACT

The present invention provides multispecific antigen-binding molecules and uses thereof. The multispecific antigen-binding molecules comprise a first antigen-binding domain that specifically binds a target molecule, and a second antigen-binding domain that specifically binds an internalizing effector protein. The multispecific antigen-binding molecules of the present invention can, in some embodiments, be bispecific antibodies that are capable of binding both a target molecule and an internalizing effector protein. In certain embodiments of the invention, the simultaneous binding of the target molecule and the internalizing effector protein by the multispecific antigen-binding molecule of the present invention results in the attenuation of the activity of the target molecule to a greater extent than the binding of the target molecule alone. In other embodiments of the invention, the target molecule is a tumor associated antigen, and the simultaneous binding of the tumor associated antigen and the internalizing effector protein by the multispecific antigen-binding molecule of the present invention causes or facilitates the targeted killing of tumor cells.

30 Claims, 27 Drawing Sheets
Specification includes a Sequence Listing.

Related U.S. Application Data on Apr. 28, 2016, provisional application No. 62/188,860, filed on Jul. 6, 2015.

(51) Int. Cl.
    *C07K 16/46* (2006.01)
    *C12N 9/64* (2006.01)

(56) References Cited

U.S. PATENT DOCUMENTS

| | | |
|---|---|---|
| 5,126,258 A | 6/1992 | Lerner et al. |
| 5,156,965 A | 10/1992 | Schochetman et al. |
| 5,208,020 A | 5/1993 | Chari et al. |
| 5,229,272 A | 7/1993 | Paul et al. |
| 5,500,362 A | 3/1996 | Robinson et al. |
| 5,585,108 A | 12/1996 | Ruddy et al. |
| 5,601,819 A | 2/1997 | Wong et al. |
| 5,602,021 A | 2/1997 | Davis et al. |
| 5,714,586 A | 2/1998 | Kunstmann et al. |
| 5,731,168 A | 3/1998 | Carter et al. |
| 5,821,337 A | 10/1998 | Carter et al. |
| 5,851,527 A | 12/1998 | Hansen |
| 5,858,728 A | 1/1999 | Gram et al. |
| 6,235,714 B1 | 5/2001 | Paul et al. |
| 6,306,393 B1 | 10/2001 | Goldenberg et al. |
| 6,372,205 B1 | 4/2002 | Duncan et al. |
| 6,387,674 B1 | 5/2002 | Trasciatti et al. |
| 6,479,265 B1 | 11/2002 | Napper et al. |
| 6,703,488 B1 | 3/2004 | Burton et al. |
| 6,855,804 B2 | 2/2005 | Paul et al. |
| 7,041,298 B2 | 5/2006 | Deshaies et al. |
| 7,105,348 B2 | 9/2006 | Murphy et al. |
| 7,223,556 B2 | 5/2007 | Zhou et al. |
| 7,235,641 B2 | 6/2007 | Kufer et al. |
| 7,335,504 B2 | 2/2008 | Haupts et al. |
| 7,371,539 B2 | 5/2008 | Church et al. |
| 7,560,424 B2 | 7/2009 | LeBowitz et al. |
| 7,592,429 B2 | 9/2009 | Paszty et al. |
| 7,750,116 B1 | 7/2010 | Doronina et al. |
| 7,754,681 B2 | 7/2010 | Feng |
| 7,771,997 B2 | 8/2010 | Chen et al. |
| 7,914,787 B2 | 3/2011 | Goldenberg et al. |
| 8,058,399 B2 | 11/2011 | Jung |
| 8,257,745 B2 | 9/2012 | Ketelson et al. |
| 8,586,713 B2 | 11/2013 | Davis et al. |
| 8,815,226 B2 | 8/2014 | Yurkovetskiy et al. |
| 9,359,437 B2 | 6/2016 | Davis et al. |
| 9,950,076 B2 | 4/2018 | Nittoli et al. |
| 11,129,903 B2 | 9/2021 | Andreev et al. |
| 11,191,844 B2 | 12/2021 | Andreev et al. |
| 11,208,458 B2 | 12/2021 | Baik et al. |
| 11,352,446 B2 | 6/2022 | Cygnar et al. |
| 11,578,135 B2 | 2/2023 | Papadopoulos et al. |
| 2005/0112694 A1 | 5/2005 | Carter et al. |
| 2005/0142141 A1 | 6/2005 | Pardridge |
| 2005/0271626 A1 | 12/2005 | Chen et al. |
| 2006/0099205 A1 | 5/2006 | Adams |
| 2007/0041978 A1 | 2/2007 | Hatiori et al. |
| 2007/0258987 A1 | 8/2007 | Francisco et al. |
| 2007/0280945 A1 | 12/2007 | Stevens et al. |
| 2008/0305497 A1 | 12/2008 | Kosmeder et al. |
| 2010/0081796 A1 | 4/2010 | Brinkmann et al. |
| 2010/0129314 A1 | 5/2010 | Singh et al. |
| 2010/0233173 A1 | 9/2010 | Wu et al. |
| 2010/0330034 A1 | 12/2010 | Bigler et al. |
| 2010/0331527 A1 | 12/2010 | Davis et al. |
| 2011/0184049 A1 | 7/2011 | Chuah et al. |
| 2011/0195454 A1 | 8/2011 | McWhirter et al. |
| 2012/0315276 A1 | 12/2012 | Otto et al. |
| 2013/0022606 A1 | 1/2013 | Otto et al. |
| 2013/0101546 A1 | 4/2013 | Yurkovetskiy et al. |
| 2013/0129739 A1 | 5/2013 | Otto et al. |
| 2013/0171147 A1 | 7/2013 | Otto et al. |
| 2013/0243775 A1 | 9/2013 | Papadopoulos et al. |
| 2013/0259833 A1 | 10/2013 | Pan |
| 2013/0272968 A1 | 10/2013 | Otto et al. |
| 2014/0065158 A1 | 3/2014 | Ma et al. |
| 2014/0141003 A1 | 5/2014 | Freiberg et al. |
| 2014/0271659 A1 | 9/2014 | Ma et al. |
| 2014/0356366 A1 | 12/2014 | Cheong et al. |
| 2015/0056221 A1 | 2/2015 | Papadopoulos et al. |
| 2015/0056222 A1 | 2/2015 | Papadopoulos et al. |
| 2016/0108133 A1 | 4/2016 | Armstrong et al. |
| 2016/0375147 A1 | 12/2016 | Nittoli et al. |
| 2017/0007715 A1 | 1/2017 | Andreev et al. |
| 2017/0209591 A1 | 7/2017 | Nittoli et al. |
| 2018/0002433 A1 | 1/2018 | Zhang et al. |
| 2018/0355017 A1 | 12/2018 | Baik et al. |
| 2019/0000984 A1 | 1/2019 | Andreev et al. |
| 2019/0112588 A1 | 4/2019 | Baik et al. |
| 2019/0309061 A1 | 10/2019 | Papadopoulos et al. |
| 2020/0095338 A1 | 3/2020 | Cygnar et al. |
| 2020/0399623 A1 | 12/2020 | Baik et al. |
| 2022/0008548 A1 | 1/2022 | Andreev et al. |
| 2022/0195011 A1 | 6/2022 | Baik et al. |
| 2022/0267477 A1 | 8/2022 | Cygnar et al. |

FOREIGN PATENT DOCUMENTS

| | | |
|---|---|---|
| WO | 1999/036437 A1 | 7/1999 |
| WO | 2001/009186 A1 | 2/2001 |
| WO | 2001/036005 A2 | 5/2001 |
| WO | 2005/089808 A2 | 9/2005 |
| WO | 2006/072166 A1 | 7/2006 |
| WO | WO 2006/108052 A2 | 10/2006 |
| WO | WO 2007/075270 A1 | 7/2007 |
| WO | 2008/011710 A1 | 1/2008 |
| WO | 2008/011711 A1 | 1/2008 |
| WO | 2008/014404 A2 | 1/2008 |
| WO | 2008/019290 A2 | 2/2008 |
| WO | WO 2008/022295 A1 | 2/2008 |
| WO | 2008/122039 A2 | 10/2008 |
| WO | 2008/150485 A2 | 12/2008 |
| WO | 2009/094561 A1 | 7/2009 |
| WO | 2009/120922 A2 | 10/2009 |
| WO | 2010/010324 A1 | 1/2010 |
| WO | 2010/115552 A1 | 10/2010 |
| WO | 2010/119119 A1 | 10/2010 |
| WO | 2011/018611 A1 | 2/2011 |
| WO | 2011/029823 A1 | 3/2011 |
| WO | 2011/069794 A1 | 6/2011 |
| WO | 2011/130598 A1 | 10/2011 |
| WO | 2011/147986 A1 | 12/2011 |
| WO | 2012/005982 A2 | 1/2012 |
| WO | 2012/136519 A1 | 10/2012 |
| WO | 2012/143379 A1 | 10/2012 |
| WO | 2012/143523 A1 | 10/2012 |
| WO | 2012/143524 A1 | 10/2012 |
| WO | 2012/166559 A1 | 12/2012 |
| WO | 2013/053872 A1 | 4/2013 |
| WO | 2013/053873 A1 | 4/2013 |
| WO | 2013/055990 A1 | 4/2013 |
| WO | 2013/055993 A1 | 4/2013 |
| WO | 2013/068874 A1 | 5/2013 |
| WO | 2013/085925 A1 | 6/2013 |
| WO | 2013/138400 A1 | 9/2013 |
| WO | 2013/166604 A1 | 11/2013 |
| WO | 2014/065661 A1 | 5/2014 |
| WO | WO 2014/085621 A1 | 6/2014 |
| WO | 2014/143909 A1 | 9/2014 |
| WO | 2014/145090 A1 | 9/2014 |
| WO | 2014/182970 A1 | 11/2014 |
| WO | 2015/026907 A1 | 2/2015 |
| WO | 2015/031396 A1 | 3/2015 |
| WO | WO 2016/077840 A2 | 5/2016 |
| WO | WO 2016/085820 A1 | 6/2016 |
| WO | 2016/160615 A1 | 10/2016 |
| WO | WO 2017/100467 A1 | 6/2017 |
| WO | 2017/134197 A1 | 8/2017 |
| WO | WO 2006/088503 A1 | 8/2017 |
| WO | WO 2017/131496 A1 | 8/2017 |
| WO | WO 2017/147414 A1 | 8/2017 |

(56) References Cited

FOREIGN PATENT DOCUMENTS

| | | |
|---|---|---|
| WO | WO 2017/190079 A1 | 11/2017 |
| WO | WO 2018/226861 A1 | 12/2018 |
| WO | WO 2019/157224 A1 | 8/2019 |

OTHER PUBLICATIONS

Almagro et al., "Progress and Challenges in the Design and Clinical Development of Antibodies for Cancer Therapy," Front. Immunol., 8: 1751, (Jan. 2018).

Baik et al., "Next-generation antibody-guided enzyme replacement therapy in Pompe disease mice," Mol. Genet. Metab., 123:S21, (2018).

Berger, et al., "Fusion protein technologies for biopharmaceuticals: Applications and challenges," MAbs, 7(3):456-460, (2015).

Boado et al., "IgG-enzyme fusion protein: pharmacokinetics and anti-drug antibody response in rhesus monkeys," Bioconjug. Chem., 24(1):97-104, (2013).

Boado, et al., "Genetic engineering of a lysosomal enzyme fusion protein for targeted delivery across the human blood-brain barrier," Biotechnol. Bioeng., 99(2):475-484, (2008).

Braun et al., "Preclinical studies of lymphocyte gene therapy for mild Hunter syndrome (mucopolysaccharidosis type II)," Hum. Gene Ther., 7(3):283-290, (1996), Abstract.

Brown et al., :"Tolerance of single, but not multiple, amino acid replacements in antibody VH CDR 2: a means of minimizing B cell wastage from somatic hypermutation?," J. Immunol., 156(9): 3285-3291, (1996).

Chiu et al., "Antibody Structure and Function: The Basis for Engineering Therapeutics," Antibodies (Basel), 8(4):55, (2019).

Darvish-Damavandi, et al., "Towards the development of an enzyme replacement therapy for the metabolic disorder propionic acidemia," Mol. Genet. Metab. Rep., 8:51-60, (2016).

Devay et al., "Improved Lysosomal Trafficking Can Modulate the Potency of Antibody Drug Conjugates," Bioconjug. Chem., 28(4): 1102-1114, (Feb. 2017).

Ferrua et al., "Twenty-Five Years of Gene Therapy for ADA-SCID: From Bubble Babies to an Approved Drug," Hum. Gene Ther., 28(11): 972-981, (2017), Abstract.

Hsu et al., "Enhanced delivery of a-glucosidase for Pompe disease by ICAM-1-targeted nanocarriers: comparative performance of a strategy for three distinct lysosomal storage disorders," Nanomedicine, 8(5):731-739, (2012).

Mazor et al.. "Enhanced tumor-targeting selectivity by modulating bispecific antibody binding affinity and format valence," Sci. Rep., 7:40098, (Jan. 2017).

Ohashi et al., "Enzyme replacement therapy for lysosomal storage diseases," Pediatr. Endocrinol. Rev., 10 Suppl 1:26-34, (2012), Abstract.

Pardridge, "Blood-brain barrier drug delivery of IgG fusion proteins with a transferrin receptor monoclonal antibody," Expert Opin. Drug Deliv., 12(2):207-22, (Aug. 20, 2014).

Paterson et al., "Exploiting transferrin receptor for delivering drugs across the blood-brain barrier," Drug Discov. Today Technol., 20:49-52, (Oct. 27, 2016).

Puzzo et al., "Rescue of Pompe disease in mice by AAV-mediated liver delivery of secretable acid a-glucosidase," Sci. Tranl. Med., 9(418):eaam6375, (2017).

Rofo et al., "Enhanced neprilysin-mediated degradation of hippocampal Aβ42 with a somatostatin peptide that enters the brain," Theranostics, 11(2):789-804, (Jan. 2021).

Rudikoff et al., "Single amino acid substitution altering antigen-binding specificity," Proc. Natl. Acad. Sci. U.S.A., 79(6):1979-1983, (Mar. 1982).

Saftig et al., "Lysosome biogenesis and lysosomal membrane proteins: trafficking meets function," Nature Reviews, Molecular Cell Biology, vol. 10, 623-635, (Sep. 2009).

Tanaka et al., "A novel approach to CNS dysfunction of Pompe disease with a fusion protein consisting of anti-transferrin receptor antibody and GAA enzyme," Mol. Genet. Metab., 129(2):S150-S151, (Feb. 2020).

U.S. Appl. No. 15/202,822, Advisory Action mailed Apr. 9, 2020.

U.S. Appl. No. 15/202,822, Final Office Action mailed Jan. 10, 2020.

U.S. Appl. No. 15/202,822, Final Office Action mailed Dec. 24, 2020.

U.S. Appl. No. 15/202,822, Non-Final Office Action mailed Jun. 15, 2020.

U.S. Appl. No. 15/202,822, Non-Final Office Action mailed Jun. 25, 2019.

U.S. Appl. No. 15/202,822, Non-Final Office Action mailed Oct. 19, 2018.

U.S. Appl. No. 15/202,822, Notice of Allowance mailed Apr. 27, 2021.

U.S. Appl. No. 15/202,822, Notice of Allowance mailed Sep. 2, 2021.

U.S. Appl. No. 15/202,822, Requirement for Restriction/Election mailed Apr. 3, 2018.

U.S. Application No. 15/738, 801, Final Office Action mailed Sep. 25, 2020.

U.S. Application No. 15/738, 801, Non-Final Office Action mailed Mar. 5, 2020.

U.S. Appl. No. 15/738,801, Notice of Allowance mailed Jul. 14, 2021.

U.S. Appl. No. 15/738,801, Notice of Allowance mailed Nov. 15, 2021.

U.S. Appl. No. 15/738,801, Non-Final Office Action mailed Jan. 22, 2021.

Epping et al., (2008) "PRAME expression and clinical outcome of breast cancer," Brit J Cancer, 99:398-403.

Russo et al., (1995) "Expression of the MAGE gene family in primary and metastatic human breast cancer: Implications for tumor antigen-specific immunotherapy," Int J Cancer (Pred Oncol), 64:216-221.

Benjamini E. "Immunology: A Short Course," Wiley-Liss, Inc. New York, NY, 2nd Edition, 1991, p. 40 only.

Drenth and Waxman, Mutations in sodium-channel gene SCN9A cause a spectrum of human genetic pain disorders, J. Clin. Invest., 2007, 117(12):3603-3609.

Ferrara et al., "Recombinant renewable polyclonal antibodies," mAbs, 2015, 7(1):32-41.

Hořejši and Vlček "Novel structurally distinct family of leucocyte surface glycoproteins including CD9, CD37, CD53 and CD63," FEBS, Aug. 1991, 288(1,2): 1-4.

Statement of Relatedness under MPEP Jun. 2001 with Respect to U.S. Appl. No. 17/483,588 dated Jan. 4, 2022.

Agarwal et al., "A Pictet-Spengler ligation for protein chemical modification," Proc. Natl. Acad. Sci., USA, 2013, 110:46-51.

Ahmad et al., "scFv Antibody: Principles and Clinical Application," Clinical and Developmental Immunology, vol. 2012, article ID 980250, 15 pages.

Al-Lazikani et al., "Standard Conformations for the Canonical Structures of Immunoglobulins," J. Mol. Biol., 1997, 273:927-948.

Altschul et al., "Basic Local Alignment Search Tool," J. Mol. Biol., 1990, 215:403-410.

Altschul et al., "Gapped BLAST and PSI-BLAST: a new generation of protein database search programs," Nucleic Acids Res., 1997, 25(17):3389-3402.

Andreev et al., "Abstract A131: Rapid constitutive internalization and degradation of prolactin receptor (PRLR) is associated with potent cell killing by PRLR antibody drug conjugates (ADC)," Molecular targets and Cancer Therapeutics, 14(12):supp. 2, Abstract No. A131 (Dec. 2015).

Andreev et al., "Bispecific Antibodies and Antibody—Drug Conjugates (ADCs) Bridging HER2 and Prolactin Receptor Improve Efficacy of HER2 ADCs," Mol. Cancer Ther., Apr. 2017, 16(4):681-693.

Arribas and Cutler, "Weibel-Palade Body Membrane Proteins Exhibit Differential Trafficking After Exocytosis in Endothelial Cells," Traffic, 2000, 1:783-793.

(56) References Cited

OTHER PUBLICATIONS

Azad et al., "A fully human CXCR4 antibody demonstrates diagnostic utility and therapeutic efficacy in solid tumor xenografts," Oncotarget, 2016, 7(11):12344-12358.
Bareford and Swaan, "Endocytic mechanisms for targeted drug delivery," Advanced Drug Delivery Reviews, Elsevier, Amsterdam, NL, 2007, 59(8):748-758.
Benedict et al., "Determination of the binding affinity of an anti-CD34 single-chain antibody using a novel, flow cytometry based assay," J Immunol Methods., 1997, 201(2):223-231.
Berditchevski et al., "Generation of Monoclonal Antibodies to Integrin-associated Proteins," Journal of Biological Chemistry, Nov. 1997, 272(46):29174-29180.
Bode et al., "Antibody-Directed Fibrinolysis: An Antibody Specific for Both Fibrin and Tissue Plasminogen Activator," Journal of Biological Chemistry, Jan. 1989, 264(2):944-948.
Boersma et al., "DARPins and other repeat protein scaffolds: advances in engineering and applications," Curr. Opin. Biotechnol., 2011, 22:849-885.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Bostrom et al., "Variants of the Antibody Herceptin That Interact with HER2 and VEGF at the Antigen Binding Site," Science, 2009, 323(5921):1610-1614.
Bouilly et al., "Prolactin signaling mechanisms in ovary," Molecular and Cellular Endocrinology, 2012, 356:80-87.
Brissinck et al., (1993) "Bispecific Antibodies in Lymphoma," Intern. Rev. Immunol., 10(2-3): 187-194.
Caplus Accession No. 1990:211724, Year 1990.
Carrico et al., "Introducing genetically encoded aldehydes into proteins," Nat. Chem. Biol., 2007, 3:321-322.
Chen et al., "In vivo studies of the anti-tumor effects of a human prolactin antagonist, hPRL-G129R," International Journal of Oncology, 20:813-818 (2002).
Clevenger and Kline, "Prolactin receptor signal transduction," 10(10) Lupus, (2001) 10:706-718.
Clynes et al., "Fc receptors are required in passive and active immunity to melanoma," Proc. Natl. Acad. Sci. (USA), 1998, 95:652-656.
Core et al., "Hemojuvelin and bone morphogenetic protein (BMP) signaling in iron homeostasis," Frontiers in Pharmacology, May 13, 2014, 5(104):1-9.
Devay et al., "Characterization of proprotein convertase subtilisin/kexin type 9 (PCSK9) trafficking reveals a novel lysosomal targeting mechanism via amyloid precursor-like protein 2 (APLP2)," J. Biol. Chem., Apr. 2, 2013, 288(15):10805-10818, doi: 10.1074/jbc.M113.453373. Epub Feb. 19, 2013.
Devay et al., "Improved Lysosomal Trafficking Can Modulate the Potency of Antibody Drug Conjugates," Bioconjugate Chem., 2017, 28(4):1102-1114, DOI: 10.1021/acs.bioconjchem.7b00013.
Dipadova et al., "A Broadly Cross-Protective Monoclonal Antibody Binding to *Escherichia coli* and *Salmonella lipopolysaccharides*," Infection and Immunity, Sep. 1993, 61(9):3863-3872.
Doronina et al., "Development of potent monoclonal antibody auristatin conjugates for cancer therapy," Nature Biotechnology, 2003, 21(7):778-784 and p. 941 Corrigendum.
Ducry and Stump, "Antibody-Drug Conjugates: Linking Cytotoxic Payloads to Monoclonal Antibodies," Bioconjugate Chem., 2010, 21:5-13.
Duffield et al., "The tetraspanin CD63 enhances the internalization of the H,K-ATPase ß-subunit," Proc. Nail. Acad. Sci. USA, Dec. 2003, 100(26):15560-15565.
Ehring, "Hydrogen Exchange/Electrospray Ionization Mass Spectrometry Studies of Structural Features of Proteins and Protein/Protein Interactions," Analytical Biochemistry, 1999, 267(2):252-259.
Eigenbrot et al., "Structural basis for high-affinity HER2 receptor binding by an engineered protein," PNAS, 2010, 107(34):15039-15044.
Engen and Smith, "The Basics of Ion Chromatography," Anal. Chem., 2001, 73:256A-265A.
Ferland et al., "The effect of chloroquine on lysosomal prolactin receptors in rat liver," Endocrinology, 1984, 115(5):1842-1849.
Flannery et al., "Palmitoylation-dependent association with CD63 targets the CA2+ sensor synaptotagmin VII to lysosomes," J. Cell Biol., Nov. 2010, 191(3):599-613.
Fu et al., "Insights into HER2 signaling from step-by-step optimization of anti-HER2 antibodies," mAbs, 2014, 6(4):978-990.
Genty et al., "Endocytosis and degradation of prolactin and its receptor in Chinese hamster ovary cells stably transfected with prolactin receptor cDNA," Mol. Cell Endocrinol., 1994, 99(2):221-228.
Geuijen et al. "Affinity ranking of antibodies using flow cytometry: Application in antibody phage display-based target discovery," J Immunol Methods, 2005, 302(1-2):68-77.
Ghosh et al., "An Endocytosed TGN38 Chimeric Protein is Delivered to the TGN after Trafficking Through the Endocytic Recycling Compartment in CHO Cells," J. Cell Biol., Aug. 1998, 142(4):923-936.
Gomery et al., "Antibody WN1 222-5 mimics Toll-like receptor 4 binding in the recognition of LPS," Proc. Natl. Acad. Sci USA, 2012, 109(51):20877-20882.
Gonnet et al., "Exhaustive Matching of the Entire Protein Sequence Database," Science, 1992, 256: 1443-1445.
Gordon et al., "Clinical Activity of Pertuzumab (rhuMAb 2C4), a HER Dimerization Inhibitor, in Advanced Ovarian Cancer: Potential Predictive Relationship With Tumor HER2 Activation Status," mAbs, 2006, 24(26):4324-4332.
Guan et al., "The correlation between the expression of PRL-R and ER/PR in breast cancer," Medline, 2010, 30:596-598, Accession No. 2010210497, 1 page.
Gupta et al., "Dual-targeting immunotherapy of lymphoma: potent cytotoxicity of anti-CD20/CD74 bispecific antibodies in mantle cell or other lymphomas," Blood, Jan. 23, 2012, 119(16):3767-3778.
Hamblett et al., "Effects of Drug Loading on the Antitumor Activity of a Monoclonal Antibody Drug Conjugate," American Association for Cancer Research, Oct. 15, 2004, 10(20):7063-7070.
Hevir et al., "Expression of estrogen and progesterone receptors and estrogen metabolizing enzymes in different breast cancer cell lines," Chemico-Biological Interactions, 2011, 191:206-216, doi:10.1016/j.cbi.2010.12.013.
Hofer et al., "An engineered selenocysteine defines a unique class of antibody derivatives," Proc. Natl. Acad. Sci., USA, 2008, 105:12451-12456.
Hollander et al., "Selection of Reaction Additives Used in the Preparation of Monomeric Antibody-Calicheamicin Conjugates," Bioconjugate Chem., 2008, 19:358-361.
Holliger et al., ""Diabodies": Small bivalent and bispecific antibody fragments," PNAS USA, 1993, 90:6444-6448.
Horwitz et al., "Variant T47D human breast cancer cells with high progesterone-receptor levels despite estrogen and antiestrogen resistance," Cell. Mar. 28, 1982(3):633-642.
Jarantow et al., "Impact of Cell-surface Antigen Expression on Target Engagement and Function of an Epidermal Growth Factor Receptor x c-MET Bispecific Antibody," J Biol Chem., Oct. 9, 2015, 290(41):24689-24704, doi: 10.1074/jbc.M115.651653.
Jeger et al., "Site-Specific and Stoichiometric Modification of Antibodies by Bacterial Transglutaminase," Angew Chemie, Inter. Ed., 2010, 49:9995-9997.
Junghans et al., "Anti-Tac-H, a Humanized Antibody to the Interleukin 2 Receptor with New Features for Immunotherapy in Malignant and Immune Disorders," Cancer Res. 1990, 50:1495-1502.
Kabat et al., (1991) "Tabulation and Analysis of Amino Acid and Nucleic Acid Sequences of Precursors, V-Regions, C-Regions, J-Chain, T-Cell Receptors for Antigen, T-Cell Surface Antigens, alpha2-Microglobulins, Major Histocompatibility Antigens, Thy-1, Complement, C-Reactive Protein, Thymopoietin, Integrins, Post-gamma Globulin, a 2-Macroglobulins, and Other Related Proteins",

(56) References Cited

OTHER PUBLICATIONS

Sequences of Proteins of Immunological Interest, Fifth Edition; NIH Publication No. 91-3242, National Institutes of Health, Bethesda, Md. (37 pages).
Kelly et al., "Preclinical Activity of the Novel Anti-Prolactin Receptor (PRLR) Antibody-Drug Conjugate REGN2878-DM1 in PRLR-Positive Breast Cancers," Mol. Cancer Ther., 2017, 16(7):1299-1311, doi: 10.1158/1535-7163.MCT-16-0839.Epub2017Apr4.
Klein et al., "Progress in overcoming the chain association issue in bispecific heterodimeric IgG antibodies," mAbs, 2012, 4:6 653-663 (12 pages).
Kobayashi et al., "The Tetraspanin CD63/lamp3 Cycles between Endocytic and Secretory Compartments in Human Endothelial Cells," Molecular Biology, May 2000, 11:1829-1843.
Kontermann, "Dual targeting strategies with bispecific antibodies," mAbs, 2012, 4(2):182-197.
Kufer et al., "A revival of bispecific antibodies," Trends Biotechnol., 2004, 22(5):238-244.
Lambert and Chari, "Ado-trastuzumab Emtansine (T-DM1): An Antibody-Drug Conjugate (ADC) for HER2-Positive Breast Cancer," Journal of Medicinal Chemistry, (Aug. 28, 2014), 57(16):6949-6964.
Langer, "New Methods of Drug Delivery," Science, 1990, 249:1527-1533.
Lee et al., "Impaired Retrograde Membrane Traffic Through Endosomes in a Mutant CHO Cell Defective in Phosphalidyl Serine Synthesis," Genes to Cells, 2012, 17:728-736.
Li et al., "Cell Type and Culture Condition-Dependent Alternative Splicing in Human Breast Cancer Cells Revealed by Splicing-Sensitive Microarrays," Cancer Res., Feb. 15, 2006, 66(4):1990-1999.
Li et al., "Dkk1 Stabilizes Wnt Co-Receptor LRP6: Implication for Wnt Ligand-Induced LRP6 Down-Regulation," PLoS One Jun. 2010, 5(6):e11014.
Lieu et al., "The Golgin GCC88 Is Required for Efficient Retrograde Transport of Cargo from the Early Endosomes to the Trans-Golgi Network," Mol. Bioi. Cell, Dec. 2007, 18:4979-4991.
Lloyd et al., "Modelling the human immune response: performance of a 1011 human antibody repertoire against a broad panel of therapeutically relevant antigens," Protein Engineering, Design & Selection, 2009, 22(3):159-168.
Mantegazza et al., "CD63 Tetraspanin Slows Down Cell Migration and Translocates to the Endosomal-Lysosomal- MIICs Route after Extracellular Stimuli in Human Immature Dendritic Cells," Blood, Aug. 2004, 104(4):1183-1190.
Martin et al., "Modeling antibody hypervariable loops: A combined algorithm," Proc. Natl. Acad. Sci. USA, 1989, 86:9268-9272.
McDonagh et al., "Antitumor Activity of a Novel Bispecific Antibody That Targets the ErbB2/ErbB3 Oncogenic Unit and Inhibits Heregulin-Induced Activation of ErbB3", Molecular Cancer Therapeutics, Mar. 2012, 11(3):582-593, XP002684950, ISSN: 1535-7163, DOI:10.1158/1535-7163.MCT-11-0820.
Moody et al., "Receptor Crosslinking: A General Method to Trigger Internalization and Lysosomal Targeting of Therapeutic Receptor:Ligand Complexes," Molecular Therapy, 2015, 23(12):1888-1898.
Mordenti et al., "Interspecies Scaling of Clearance and Volume of Distribution Data for Five Therapeutic Proteins," Pharmaceutical Research, 1991, 8:1351-1359.
Muller-Loennies, et al., "Identification of a Cross-reactive Epitope Widely Present in Lipopolysaccharide from Enterobacteria and Recognized by the Cross-protective Monoclonal Antibody WN1 222-5," J. Biol. Chem., 2003, 278(28):25618-25627.
Ollivier-Bousquet "Transferrin and Prolactin Transcytosis in the Lactating Mammary Epithelial Cell," Journal of Mammary Gland Biology and Neoplasia, 1998, 3(3):303-313.
Pearson, "Using the FASTA Program to Search Protein and DNA Sequence Databases," Chapter 26, Methods Mol. Biol., 1994, 26:307-331.
Phillips et al., "Dual Targeting of HER2-Positive Cancer with Trastuzumab Emtansine and Pertuzumab: Critical Role for Neuregulin Blockade in Antitumor Response to Combination Therapy," Clinical Cancer Research, 2014, 20(2):456-468.
Poljak et al., "Production and structure of diabodies," Structure, 1994, 2:1121-1123.
Pols and Klumperman, "Trafficking and Function of the Tetraspanin CD63," Exp. Cell Res., Oct. 2009, 315:1584-1592.
Powell et al., "Compendium of Excipients for Parenteral Formulations" PDA J. Pharm. Sci. Technol., 1998, 52:238-311.
Rabuka et al., "Site-specific chemical protein conjugation using genetically encoded aldehyde tags," Nat. Protocols, 2012, 7(6):1052-1067.
Reineke, "Antibody Epitope Mapping Using Arrays of Synthetic Peptides," Methods Mol. Biol., Chapter 26, 2004, 248:443-463.
Rhoden et al., "A Modeling and Experimental Investigation of the Effects of Antigen Density, Binding Affinity, and Antigen Expression Ratio on Bispecific Antibody Binding to Cell Surface Targets," J Biol. Chem. 291, May 2016, 291(21):11337-11347, doi: 10.1074/jbc.M116.714287.
Ridgway et al., "'Knobs-into-holes' engineering of antibody CH3 domains for heavy chain heterodimerization," Protein Eng., 1996, 9(7):617-621.
Říhová "Receptor-mediated targeted drug or toxin delivery," Advanced Drug Delivery Reviews, 1998, 29:273-289.
Robinson et al., "Targeting ErbB2 and ErbB3 with a bispecific single-chain Fv enhances targeting selectivity and induces a therapeutic effect in vitro", British Journal of Cancer, vol. 99, No. 9, Oct. 28, 2008 (Oct. 28, 2008), pp. 1415-1425, XP009115294, ISSN: 0007-0920, Doi: 10.1038/SJ.BJC. 6604700.
Ryan et al., "Polyclonal Antibody Production Against Chito-Oligosaccharides," Food & Agriculture Immunol., 2001, 13:127-130.
Sapra et al., "Monoclonal antibody-based therapies in cancer: Advances and challenges," Pharmacol. & Therapeutics, 2013, 138:452-469.
Schanzer et al., (Jul. 2014) "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties," J. Biol. Chem., 289(27):18693-18706.
Schiweck et al., "Sequence analysis and bacterial production of the anti-c-myc antibody 9E10: the $V_H$ domain has an extended CDR-H3 and exhibits unusual solubility," FEBS Lett., 1997, 414(1):33-38.
Schumacher et al., "Current Status: Site-Specific Antibody Drug Conjugates," J. Clin. Immunol., 2016, 36(Suppl 1):S100-S107.
Scotti et al., "Additive effects of a prolactin receptor antagonist, G129R, and herceptin on inhibition of HER2-overexpressing breast cancer cells," Breast Cancer Research and Treatment, 2008, 111:241-250.
Sefton, "Implantable Pumps," CRC Crit. Ref. Biomed. Eng., 1987, 14(3):201-240.
Senter, "Activation of Prodrugs by Antibody-Enzyme Conjugates: A New Approach to Cancer Therapy," FASEB J., 1990, 4:188-193.
Shahied et al., "Bispecific Minibodies Targeting HER2/neu and CD16 Exhibit Improved Tumor Lysis When Placed in a Divalent Tumor Antigen Binding Format," J. Bioi. Chem., Dec. 2004, 279(52):53907-53914.
Shaunak et al., "Site-specific PEGylation of native disulfide bonds in therapeutic proteins," Nat. Chem. Biol., 2006, 2(6):312-313.
Shields et al., "Lack of Fucose on Human IgG1 N-Linked Oligosaccharide Improves Binding to Human Fc RIII and Antibody-dependent Cellular Toxicity," Journal of Biological Chemistry, 2002, 277(30):26733-26740.
Shimamoto et al., "Peptibodies: A flexible alternative format to antibodies," Mabs, 2012, 4(5):586-591.
Takino et al., "Tetraspanin CD63 promotes targeting and lysosomal proteolysis of membrane-type 1 matrix metalloproteinase," Biochem. Biophys. Res. Commun., 2003, 304:160-166.
Tavare et al., "An effective immuno-PET imaging method to monitor CD8-dependent responses to immunotherapy," Cancer Res., 2016, 76(1):73-82.
Taylor et al., "A transgenic mouse that expresses a diversity of human sequence heavy and light chain immunoglobulins," Nucl. Acids Res., 1992, 20(23): 6287-6295.

(56) References Cited

OTHER PUBLICATIONS

Tomer, "Characterization of a discontinuous epitope of the human immunodeficiency virus (HIV) core protein p24 by epitope excision and differential chemical modification followed by mass spectrometric peptide mapping analysis," Protein Science, 2000, 9:487-496.
Tuscano et al., "The Bs20x22 anti-CD20-CD22 bispecific antibody has more lymphomacidal activity than do the parent antibodies alone," Cancer Immunol. Immunother., Feb. 24, 2011, 60(6):771-780.
Tutt et al., "TRISPECIFIC F(ab')$_3$ Derivatives That Use Cooperative Signaling Via the TCR/CD3 Complex and CD2 To Activate and Redirect Resting Cytotoxic T Cells," J. Immunol., 1991, 147(1):60-69.
Varghese et al., "Polyubiquitination of Prolactin Receptor Stimulates Its Internalization, Postinternalization Sorting, and Degradation via the Lysosomal Pathway," Molecular and Cellular Biology, 28:5275-5287 (Sep. 2008).
Vincent and Zurini, "Current strategies in antibody engineering: Fc engineering and pH-dependent antigen binding, bispecific antibodies and antibody drug conjugates," Biotechnol. J., 2012, 7:1444-1450.
Ward et al., "Binding activities of a repertoire of single immunoglobulin variable domains secreted from *Escherichia coli*," Nature, 1989, 341:544-546.
Wu et al., "Receptor-mediated in Vitro Gene Transformation by Soluble DNA Carrier System," J. Biol. Chem., 1987, 262(10):4429-4432.
Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.
Life Technologies/ThermoFisher scientific product 35-9200 https://www.thermofisher.com/antibody/product/Prolactin-Receptor-Antibody-clone-1A2B1-Monoclonal/35-9200 (Accessed on Mar. 19, 2019).
Trastuzumab https://www.accessdata.fda.gov/drugsatfda_docs/label/1998/trasgen092598lb.pdf (Sep. 1998).
Dako A0485 https://www.agilent.com/cs/library/packageinsert/public/103814005.PDF (2013).
International Search Report and Written Opinion for PCT/US2016/065647, Mailed Jun. 8, 2017.
International Search Report and Written Opinion Received for PCT Application No. PCT/US2013/030636, mailed Aug. 6, 2013.
International Search Report and Written Opinion and Received for PCT Application No. PCT/US2016/041055, mailed Dec. 5, 2016.
Alves et al., (2003) "EphA2 as Target of Anticancer Immunotherapy: Identification of HLA-A*0201-Restricted Epitopes," Cancer Res, 63:8476-8480.
Cazet et al., (2009) "Gp3 synthase overexpression enhances proliferation and migration of MDA-MB-231 breast cancer cells," Biol Chem, 390:601-609.
Chia et al., (2001) "Prognostic Significance of a Novel Hypoxia-Regulated Marker, Carbonic Anhydrase IX, in Invasive Breast Carcinoma," J Clin Oncol, 19(16):3660-3668.
Eller et al., (Jul. 13, 2015) "Human Cancer Antigen Globo H Is a Cell-Surface Ligand for Human Ribonuclease 1," ACS Cent. Sci., 1:181-190.
Geng et al., (Jul. 27, 2012) "Three to tango: MUC1 as a ligand for both E-selectin and ICAM-1 in the breast cancer metastatic cascade," Frontiers in Oncology, 2(76)1-8.
Hakomori S. (2001) "Tumor-Associated Carbohydrate Antigens Defining Tumor Malignancy: Basis for Development of Anti-Cancer Vaccines," In: Wu, A.M. (ed) The Molecular Immunology of Complex Carbohydrates-2, Kluwer Academic / Plenum Publishers / Springer, Boston, MA Adv Exp Med Biol, 491:369-402.

Kraft et al., "Anti-CD63 antibodies suppress IgE-dependent allergic reactions in vitro and in vivo," JEM, 2005, 201(3):385-396.
Orlowski et al., (Apr. 25, 2012) "Binding of carbonic anhydrase IX to extracellular loop 4 of the NBCe1 $Na^+$/$HCO3^-$ cotransporter enhances NBCe1-mediated $HCO3^-$ influx in the rat heart," Am. J. Physiol. Cell Physiol., 303:C69-C80.
Perez-Pinera et al., Author Manuscript, (2007) "Anaplastic Lymphoma Kinase is Expressed in Different Subtypes of Human Breast Cancer," Biochem Biophys Res Commun, 358(2):399-403.
Rajkumar and Gullick (1994) "The Type I growth factor receptors in human breast cancer" Breast Cancer Res Treat, 29:3-9.
Rump et al., (Mar. 5, 2004) "Binding of Ovarian Cancer Antigen CA125/MUC16 to Mesothelin Mediates Cell Adhesion," Journal of Biological Chemistry, 279(10):9190-9198.
Sarcione and Hart (1985) "Biosynthesis of Alpha Fetoprotein by MCF-7 Human Breast Cancer Cells," Int J Cancer, 35:315-318.
Sommers et al., (1994) "Alteration in B-Catenin Phosphorylation and Plakoglobin Expression in Human Breast Cancer Cells," Cancer Res, 54:3544-3552.
Stoica, et al., (May 18, 2001) "Identification of Anaplastic Lymphoma Kinase as a Receptor for the Growth Factor Pleiotrophin," Journal of Biological Chemistry, 276(20):16772-16779.
Thomas et al., (Jun. 6, 2008) "Carcinoembryonic Antigen and CD44 Variant Isoforms Cooperate to Mediate Colon Carcinoma Cell Adhesion to E- and L-selectin in Shear Flow," Journal of Biological Chemistry, 283(23):15647-15655.
Tormey et al., (1975) "Biological Markers in Breast Carcinoma: I. Incidence of Abnormalities of CEA, HCG, Three Polyamines, and Three Minor Nucleosides," Cancer, 35:1095-1100.
Wang et al., (2012) "Clinicopathological Significance of Mesothelin Expression in Invasive Breast Cancer," J Int Med Res, 40:909-916.
Wingett et al., (1998) "CD40 is functionally expressed on human breast carcinomas: Variable inducibility by cytokines and enhancement of Fas-mediated apoptosis," Breast Cancer Res Treat, 50:27-36.
Zhang et al., (2014) "Folate Receptor a Associated with Triple-Negative Breast Cancer and Poor Prognosis," Arch Pathol Lab Med, 138:890-895.
Zrihan-Licht et al., (1994) "Characterization and molecular cloning of a novel MUC1 protein, devoid of tandem repeats, expressed in human breast cancer tissue," Eur J Biochem., 224:787-795.
Statement of Relatedness under MPEP 2001.06 with Respect to the instant U.S. Application filed Sep. 23, 2021.
Angal et al. (1993) "A single amino acid substitution abolishes the heterogeneity of chimeric mouse/human (IgG4) antibody," Molecular Immunology 30(1):105-108 Abstract Only.
Audran et al., "Internalization of human macrophage surface antigens induced by monoclonal antibodies," Journal of Immunological Methods, 1995, 188:147-154.
Demetrick, et al. "ME491 Melanoma-Associated Glycoprotein Family: Antigenic Identity of ME491, NKI/C-3, Neuroglandular Antigen (NGA), and CD63 Proteins," Journal Natl. Cancer Inst., 1992; 84(6):422-429.
Huston et al, "Protein engineering of antibody binding sites: Recovery of specific activity in an anti-digoxin single-chain Fv analogue produced in *Escherichia coli*," PNAS, 1988, 85:16:5879-5883.
Lee et al., "Novel strategy for a bispecific antibody: induction of dual target internalization and degradation," Oncogene, 2016, 35(34):4437-4446.
Robinson e al., "Optimizing the stability of single-chain proteins by linker length and composition mutagenesis," PNAS, 1998, 95(11):5929-5934.
Statement of Relatedness under MPEP Jun. 2001 with Respect to U.S. Appl. No. 17/483,588 dated Aug. 17, 2022.

* cited by examiner

SEQUENCE LISTING

```
<160> NUMBER OF SEQ ID NOS: 12

<210> SEQ ID NO 1
<211> LENGTH: 502
<212> TYPE: PRT
<213> ORGANISM: Artificial sequence
<220> FEATURE:
<223> OTHER INFORMATION: synthetic

<400> SEQUENCE: 1
```

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His Gly Pro Gly Glu Pro Arg
            260                 265                 270

Gly Pro Thr Ile Lys Pro Cys Pro Cys Lys Cys Pro Ala Pro Asn
        275                 280                 285

Leu Leu Gly Gly Pro Ser Val Phe Ile Phe Pro Pro Lys Ile Lys Asp
    290                 295                 300

Val Leu Met Ile Ser Leu Ser Pro Ile Val Thr Cys Val Val Asp
305                 310                 315                 320

Val Ser Glu Asp Asp Pro Asp Val Gln Ile Ser Trp Phe Val Asn Asn
                325                 330                 335

Val Glu Val His Thr Ala Gln Thr Gln Thr His Arg Glu Asp Tyr Asn
            340                 345                 350

Ser Thr Leu Arg Val Val Ser Ala Leu Pro Ile Gln His Gln Asp Trp
        355                 360                 365

Met Ser Gly Lys Glu Phe Lys Cys Lys Val Asn Asn Lys Asp Leu Pro
370                 375                 380

Ala Pro Ile Glu Arg Thr Ile Ser Lys Pro Lys Gly Ser Val Arg Ala
385                 390                 395                 400

Pro Gln Val Tyr Val Leu Pro Pro Glu Glu Met Thr Lys Lys
                405                 410                 415

Gln Val Thr Leu Thr Cys Met Val Thr Asp Phe Met Pro Glu Asp Ile
                420                 425                 430

Tyr Val Glu Trp Thr Asn Asn Gly Lys Thr Glu Leu Asn Tyr Lys Asn
            435                 440                 445

Thr Glu Pro Val Leu Asp Ser Asp Gly Ser Tyr Phe Met Tyr Ser Lys
        450                 455                 460

Leu Arg Val Glu Lys Lys Asn Trp Val Glu Arg Asn Ser Tyr Ser Cys
465                 470                 475                 480

Ser Val Val His Glu Gly Leu His Asn His Thr Thr Lys Ser Phe
                485                 490                 495

Ser Arg Thr Pro Gly Lys
                500

<210> SEQ ID NO 2
<211> LENGTH: 496
<212> TYPE: PRT
<213> ORGANISM: Artificial sequence
<220> FEATURE:
<223> OTHER INFORMATION: synthetic

<400> SEQUENCE: 2

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

-continued

```
Gln Pro Tyr Pro Cys Ala Glu Asp Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
            130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
                180                 185                 190

Ser Asp Cys Ala Ser Gly Leu Cys Cys Ala Arg His Phe Trp Ser Lys
            195                 200                 205

Ile Cys Lys Pro Val Leu Lys Glu Gly Gln Val Cys Thr Lys His Arg
        210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His Gly Pro Gly Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

```
<210> SEQ ID NO 3
<211> LENGTH: 122
<212> TYPE: PRT
<213> ORGANISM: Artificial sequence
<220> FEATURE:
<223> OTHER INFORMATION: synthetic

<400> SEQUENCE: 3

Glu Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Ile Lys Tyr Phe Arg Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala His Tyr Tyr Cys
                85                  90                  95

Ala Lys Glu Ser Ser Ser Trp Tyr Phe Tyr His Gly Leu Asp Val Trp
            100                 105                 110

Gly Gln Gly Thr Met Val Thr Val Ser Ser
        115                 120

<210> SEQ ID NO 4
<211> LENGTH: 114
<212> TYPE: PRT
<213> ORGANISM: Artificial sequence
<220> FEATURE:
<223> OTHER INFORMATION: synthetic

<400> SEQUENCE: 4

Glu Ile Val Met Thr Gln Ser Pro Leu Ser Leu Pro Val Ser Pro Gly
1               5                   10                  15

Glu Pro Ala Ser Ile Ser Cys Arg Ser Asn Gln Ser Leu Leu His Ser
                20                  25                  30

Asn Gly Asn Asn Tyr Leu Ala Trp Tyr Leu Gln Lys Pro Gly Gln Ser
            35                  40                  45

Pro His Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Gly Asp Val Gly Thr Tyr Phe Cys Met Gln Ser
                85                  90                  95

Leu Gln Ala Pro Pro Phe Thr Phe Gly Pro Gly Thr Lys Val Glu Ile
            100                 105                 110

Lys Arg

<210> SEQ ID NO 5
<211> LENGTH: 692
<212> TYPE: PRT
<213> ORGANISM: Artificial sequence
<220> FEATURE:
<223> OTHER INFORMATION: synthetic

<400> SEQUENCE: 5

Met Gly Thr Val Ser Ser Arg Arg Ser Trp Trp Pro Leu Pro Leu Leu
1               5                   10                  15
```

```
Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
            85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
            420                 425                 430
```

```
Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 6
<211> LENGTH: 15
<212> TYPE: PRT
<213> ORGANISM: Artificial sequence
<220> FEATURE:
<223> OTHER INFORMATION: synthetic

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 662
<212> TYPE: PRT
<213> ORGANISM: Homo sapiens

<400> SEQUENCE: 7

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
```

```
            35                  40                  45
Val Val Val Leu Lys Glu Glu Thr His Leu Ser Gln Ser Glu Arg Thr
 50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                     85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln Ser Ile Pro Trp Asn Leu
                115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
                180                 185                 190

Cys Asp Ser His Gly Thr His Leu Ala Gly Val Val Ser Gly Arg Asp
                195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
                275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
                355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Val Ala Arg Cys Ala
                435                 440                 445

Pro Asp Glu Glu Leu Leu Ser Cys Ser Ser Phe Ser Arg Ser Gly Lys
450                 455                 460
```

```
Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gly His Val
        515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
        610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 8
<211> LENGTH: 267
<212> TYPE: PRT
<213> ORGANISM: Homo sapiens

<400> SEQUENCE: 8

Glu Ala Trp Phe Pro Glu Asp Gln Arg Val Leu Thr Pro Asn Leu Val
1               5                   10                  15

Ala Ala Leu Pro Pro Ser Thr His Gly Ala Gly Trp Gln Leu Phe Cys
            20                  25                  30

Arg Thr Val Trp Ser Ala His Ser Gly Pro Thr Arg Met Ala Thr Ala
        35                  40                  45

Val Ala Arg Cys Ala Pro Asp Glu Glu Leu Leu Ser Cys Ser Ser Phe
50                  55                  60

Ser Arg Ser Gly Lys Arg Arg Gly Glu Arg Met Glu Ala Gln Gly Gly
65                  70                  75                  80

Lys Leu Val Cys Arg Ala His Asn Ala Phe Gly Gly Glu Gly Val Tyr
                85                  90                  95

Ala Ile Ala Arg Cys Cys Leu Leu Pro Gln Ala Asn Cys Ser Val His
            100                 105                 110

Thr Ala Pro Pro Ala Glu Ala Ser Met Gly Thr Arg Val His Cys His
        115                 120                 125

Gln Gln Gly His Val Leu Thr Gly Cys Ser Ser His Trp Glu Val Glu
    130                 135                 140

Asp Leu Gly Thr His Lys Pro Pro Val Leu Arg Pro Arg Gly Gln Pro
145                 150                 155                 160

Asn Gln Cys Val Gly His Arg Glu Ala Ser Ile His Ala Ser Cys Cys
```

```
              165                 170                 175
His Ala Pro Gly Leu Glu Cys Lys Val Lys Glu His Gly Ile Pro Ala
            180                 185                 190

Pro Gln Glu Gln Val Thr Val Ala Cys Glu Glu Gly Trp Thr Leu Thr
        195                 200                 205

Gly Cys Ser Ala Leu Pro Gly Thr Ser His Val Leu Gly Ala Tyr Ala
    210                 215                 220

Val Asp Asn Thr Cys Val Val Arg Ser Arg Asp Val Ser Thr Thr Gly
225                 230                 235                 240

Ser Thr Ser Glu Gly Ala Val Thr Ala Val Ala Ile Cys Cys Arg Ser
                245                 250                 255

Arg His Leu Ala Gln Ala Ser Gln Glu Leu Gln
            260                 265

<210> SEQ ID NO 9
<211> LENGTH: 243
<212> TYPE: PRT
<213> ORGANISM: Homo sapiens

<400> SEQUENCE: 9

Gly Ala Gly Trp Gln Leu Phe Cys Arg Thr Val Trp Ser Ala His Ser
1               5                   10                  15

Gly Pro Thr Arg Met Ala Thr Ala Val Ala Arg Cys Ala Pro Asp Glu
            20                  25                  30

Glu Leu Leu Ser Cys Ser Ser Phe Ser Arg Ser Gly Lys Arg Arg Gly
        35                  40                  45

Glu Arg Met Glu Ala Gln Gly Gly Lys Leu Val Cys Arg Ala His Asn
    50                  55                  60

Ala Phe Gly Gly Glu Gly Val Tyr Ala Ile Ala Arg Cys Cys Leu Leu
65                  70                  75                  80

Pro Gln Ala Asn Cys Ser Val His Thr Ala Pro Pro Ala Glu Ala Ser
                85                  90                  95

Met Gly Thr Arg Val His Cys His Gln Gln Gly His Val Leu Thr Gly
            100                 105                 110

Cys Ser Ser His Trp Glu Val Glu Asp Leu Gly Thr His Lys Pro Pro
        115                 120                 125

Val Leu Arg Pro Arg Gly Gln Pro Asn Gln Cys Val Gly His Arg Glu
    130                 135                 140

Ala Ser Ile His Ala Ser Cys His Ala Pro Gly Leu Glu Cys Lys
145                 150                 155                 160

Val Lys Glu His Gly Ile Pro Ala Pro Gln Glu Gln Val Thr Val Ala
                165                 170                 175

Cys Glu Glu Gly Trp Thr Leu Thr Gly Cys Ser Ala Leu Pro Gly Thr
            180                 185                 190

Ser His Val Leu Gly Ala Tyr Ala Val Asp Asn Thr Cys Val Val Arg
        195                 200                 205

Ser Arg Asp Val Ser Thr Thr Gly Ser Thr Ser Glu Gly Ala Val Thr
    210                 215                 220

Ala Val Ala Ile Cys Cys Arg Ser Arg His Leu Ala Gln Ala Ser Gln
225                 230                 235                 240

Glu Leu Gln

<210> SEQ ID NO 10
<211> LENGTH: 399
<212> TYPE: PRT
```

-continued

<213> ORGANISM: Homo sapiens

<400> SEQUENCE: 10

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
            20                  25                  30

Ala His Ser Gln Cys Lys Ile Leu Arg Cys Asn Ala Glu Tyr Val Ser
            35                  40                  45

Ser Thr Leu Ser Leu Arg Gly Gly Ser Gly Ala Leu Arg Gly
        50                  55                  60

Gly Gly Gly Gly Arg Gly Gly Val Gly Ser Gly Gly Leu Cys
65                  70                  75                  80

Arg Ala Leu Arg Ser Tyr Ala Leu Cys Thr Arg Thr Ala Arg Thr
                85                  90                  95

Cys Arg Gly Asp Leu Ala Phe His Ser Ala Val His Gly Ile Glu Asp
                100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
    195                 200                 205

Ala Leu Gly Ala Asn Ala Thr Ala Thr Arg Lys Leu Thr Ile Ile Phe
210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser
385                 390                 395

<210> SEQ ID NO 11
<211> LENGTH: 622
<212> TYPE: PRT
<213> ORGANISM: Homo sapiens

<400> SEQUENCE: 11

```
Met Lys Glu Asn Val Ala Ser Ala Thr Val Phe Thr Leu Leu Leu Phe
 1               5                  10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Gly Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380
```

```
Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
            405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
            435                 440                 445

Thr Leu Leu Asn Glu Ala Gly Lys Asp Ala Leu Lys Ser Ser Gln Thr
            450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
            515                 520                 525

Glu Asn Ser Gly Lys Pro Lys Lys Pro Gly Thr Pro Glu Asn Asn Lys
            530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
            595                 600                 605

Leu Asp Tyr Leu Asp Pro Ala Cys Phe Thr His Ser Phe His His
            610                 615                 620

<210> SEQ ID NO 12
<211> LENGTH: 21
<212> TYPE: PRT
<213> ORGANISM: Homo sapiens

<400> SEQUENCE: 12

Asp Ala His Leu Leu Glu Lys Gly Lys Ser Glu Glu Leu Leu Ser Ala
1               5                   10                  15

Leu Gly Cys Gln Asp
            20
```

MULTISPECIFIC ANTIGEN-BINDING MOLECULES AND USES THEREOF

CROSS-REFERENCE TO RELATED APPLICATIONS

This application is a continuation of U.S. application Ser. No. 15/202,822, which claims the benefit of priority under 35 USC § 119 (e) of U.S. Provisional Application No. 62/347,179, filed on Jun. 8, 2016, U.S. Provisional Application No. 62/328,900, filed on Apr. 28, 2016, and U.S. Provisional Application No. 62/188,860, filed on Jul. 6, 2015, all of which are herein specifically incorporated by reference in their entirety.

FIELD

The present invention relates to the field of therapeutic proteins, and in particular, to the field of therapeutic proteins that are capable of inactivating, blocking, attenuating, eliminating and/or reducing the concentration of one or more target molecules in vitro or in vivo.

BACKGROUND

Therapeutic treatments often require the inactivation or blocking of one or more target molecules that act on or in the vicinity of a cell. For example, antibody-based therapeutics often function by binding to a particular antigen expressed on the surface of a cell, or to a soluble ligand, thereby interfering with the antigen's normal biological activity. Antibodies and other binding constructs directed against various cytokines (e.g., IL-1, IL-4, IL-6, IL-13, IL-22, IL-25, IL-33, etc.), or their respective receptors, for instance, have been shown to be useful in treating a wide array of human ailments and diseases. Therapeutic agents of this type typically function by blocking the interaction between the cytokine and its receptor in order to attenuate or inhibit cellular signaling. In certain contexts, however, it would be therapeutically beneficial to inactivate or inhibit the activity of a target molecule in a manner that does not necessarily involve blocking its physical interaction with another component. One way in which such non-blocking attenuation of a target molecule could be achieved would be to reduce the extracellular or cell surface concentration of the target molecule. Although genetic and nucleic acid-based strategies for reducing the amount or concentration of a given target molecule are known in the art, such strategies are often fraught with substantial technical complications and unintended side effects in therapeutic settings. Accordingly, alternative non-blocking strategies are needed to facilitate the inactivation or attenuation of various target molecules for therapeutic purposes.

BRIEF SUMMARY

The present invention is based, at least in part, on the concept of attenuating or inactivating a target molecule by facilitating or bringing about a physical linkage between the target molecule and an internalizing effector protein. Through this type of physical intermolecular linkage, the target molecule can be forced to be internalized into the cell along with the internalizing effector protein, and processed by the intracellular degradative machinery, or otherwise attenuated, sequestered, or inactivated. This mechanism represents a novel and inventive strategy for inactivating or attenuating the activity of a target molecule without necessarily blocking the interaction between the target molecule and its binding partners.

Accordingly, the present invention provides a multispecific antigen-binding molecule that is capable of simultaneously binding a target molecule (T) and an internalizing effector protein (E). More specifically, the present invention provides a multispecific antigen-binding molecule comprising a first antigen-binding domain (D1), and a second antigen-binding domain (D2), wherein D1 specifically binds T, and D2 specifically binds E, and wherein the simultaneous binding of T and E by the multispecific antigen-binding molecule attenuates the activity of T to a greater extent than the binding of T by D1 alone. The enhanced attenuation of the activity of T may be due to the forced internalization/degradation of T through its physical linkage to E; however, other mechanisms of action are possible and are not excluded from the scope of the present invention.

In addition, the present invention provides methods of using the multispecific antigen-binding molecule to inactivate or attenuate the activity of a target molecule (T). In particular, the present invention provides a method for inactivating or attenuating the activity of T by contacting T and an internalizing effector protein (E) with a multispecific antigen-binding molecule, wherein the multispecific antigen-binding molecule comprises a first antigen-binding domain (D1) and a second antigen-binding domain (D2), wherein D1 specifically binds T, and wherein D2 specifically binds E; and wherein the simultaneous binding of T and E by the multispecific antigen-binding molecule attenuates the activity of T to a greater extent than the binding of T by D1 alone.

In certain embodiments of the present invention, D1 and/or D2 comprise(s) at least one antibody variable region. For example, the multispecific antigen-binding molecule can, in some embodiments, be a bispecific antibody, wherein D1 comprises an antibody heavy and light chain variable region (HCVR/LCVR) pair that specifically binds T, and wherein D2 comprises an HCVR/LCVR pair that specifically binds E. Alternatively, D1 and/or D2 may comprise a peptide or polypeptide that specifically interacts with the target molecule (T) and/or the internalizing effector protein (E). For example, if the target molecule is a cell surface receptor, then D1 may comprise a portion of a ligand that specifically binds the cell surface receptor target molecule. Similarly, if the internalizing effector protein is a cell surface internalizing receptor, then D2 may comprise a portion of a ligand that specifically binds the cell surface internalizing receptor. In certain embodiments, D1 comprises an antibody variable region that specifically binds T, and D2 comprises a peptide or polypeptide that specifically binds E. In yet other embodiments, D1 comprises a peptide or polypeptide that specifically binds T, and D2 comprises an antibody variable region that specifically binds E. In any configuration, however, the end result is that T and E are capable of being physically linked, directly or indirectly, via the simultaneous binding of T and E by a multispecific antigen-binding molecule.

Other embodiments will become apparent from a review of the ensuing detailed description.

DETAILED DESCRIPTION

Figure 1:
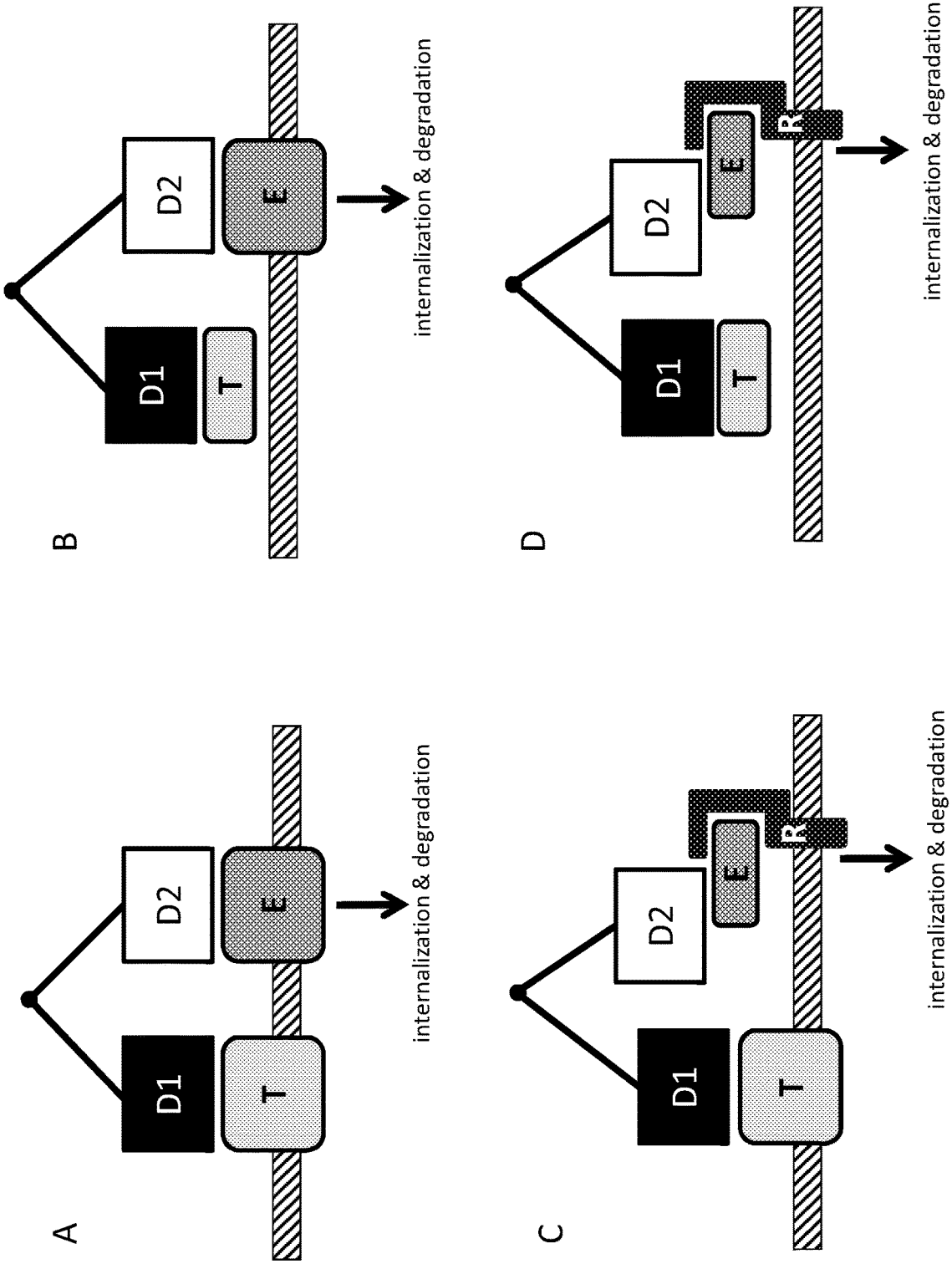
FIG. 1 (panels A-D) provides schematic representations of four general exemplary mechanisms of action for the multispecific antigen binding molecules of the present invention. In each illustrated configuration D1 is a first antigen-binding domain; D2 is a second antigen binding domain; T is a target molecule; E is an internalizing effector protein; and R is a receptor which internalizes upon binding E. Panel A depicts the situation in which both T and E are membrane-associated. Panel B depicts the situation in which T is soluble and E is membrane-associated. Panel C depicts the situation in which T is membrane-associated and E is a soluble protein that interacts with, and is internalized into the cell via the interaction of E and R. Panel D depicts the situation in which T is soluble and E is a soluble protein that interacts with, and is internalized into the cell via the interaction of E and R.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Multispecific Antigen-Binding Molecules

The present inventors have surprisingly discovered that a target molecule's activity can be attenuated by linking the target molecule to an internalizing effector protein via a multispecific antigen-binding molecule.

Accordingly, the present invention provides multispecific antigen binding molecules comprising a first antigen-binding domain (also referred to herein as "D1"), and a second antigen-binding domain (also referred to herein as "D2"). D1 and D2 each bind different molecules. D1 specifically binds a "target molecule". The target molecule is also referred to herein as "T". D2 specifically binds an "internalizing effector protein". The internalizing effector protein is also referred to herein as "E". According to the present invention, the simultaneous binding of T and E by the multispecific antigen-binding molecule attenuates the activity of T to a greater extent than the binding of T by D1 alone. As used herein, the expression "simultaneous binding," in the context of a multispecific antigen-binding molecule, means that the multispecific antigen-binding molecule is capable of contacting both a target molecule (T) and an internalizing effector protein (E) for at least some period of time under physiologically relevant conditions to facilitate the physical linkage between T and E. Binding of the multispecific antigen-binding molecule to the T and E components may be sequential; e.g., the multispecific antigen-binding molecule may first bind T and then bind E, or it may first bind E first and then bind T. In any event, so long as T and E are both bound by the multispecific antigen-binding molecule for some period of time (regardless of the sequential order of binding), the multispecific antigen-binding molecule will be deemed to "simultaneously bind" T and E for purposes of the present disclosure. Without being bound by theory, the enhanced inactivation of T is believed to be caused by the internalization and degradative rerouting of T within a cell due to its physical linkage to E. The multispecific antigen-binding molecules of the present invention are thus useful for inactivating and/or reducing the activity and/or extracellular concentration of a target molecule without directly blocking or antagonizing the function of the target molecule.

According to the present invention, a multispecific antigen-binding molecule can be a single multifunctional polypeptide, or it can be a multimeric complex of two or more polypeptides that are covalently or non-covalently associated with one another. As will be made evident by the present disclosure, any antigen binding construct which has the ability to simultaneously bind a T and an E molecule is regarded as a multispecific antigen-binding molecule. Any of the multispecific antigen-binding molecules of the invention, or variants thereof, may be constructed using standard molecular biological techniques (e.g., recombinant DNA and protein expression technology), as will be known to a person of ordinary skill in the art.

Antigen-Binding Domains

The multispecific antigen-binding molecules of the present invention comprise at least two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest. The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

In certain embodiments in which the target molecule or the internalizing effector protein is a receptor molecule, an "antigen-binding domain," for purposes of the present invention, may comprise or consist of a ligand or portion of a ligand that is specific for the receptor. For example, if the target molecule (T) is IL-4R, the D1 component of the multispecific antigen-binding molecule may comprise the IL-4 ligand or a portion of the IL-4 ligand that is capable of specifically interacting with IL-4R; or if the internalizing effector protein (E) is transferrin receptor, the D2 component of the multispecific antigen-binding molecule may comprise transferrin or a portion of transferrin that is capable of specifically interacting with the transferrin receptor.

In certain embodiments in which the target molecule or the internalizing effector protein is a ligand that is specifically recognized by a particular receptor (e.g., a soluble target molecule), an "antigen-binding domain," for purposes of the present invention, may comprise or consist of the receptor or a ligand-binding portion of the receptor. For example, if the target molecule (T) is IL-6, the D1 component of the multispecific antigen-binding molecule may comprise the ligand-binding domain of the IL-6 receptor; or if the internalizing effector protein (E) is an indirectly internalized protein (as that term is defined elsewhere herein), the D2 component of the multispecific antigen-binding molecule may comprise a ligand-binding domain of a receptor specific for E.

Methods for determining whether two molecules specifically bind one another are well known in the art and include, for example, equilibrium dialysis, surface plasmon resonance, and the like. For example, an antigen-binding domain, as used in the context of the present invention, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies and Antigen-Binding Fragments of Antibodies

As indicated above, an "antigen-binding domain" (D1 and/or D2) can comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., T or E). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The D1 and/or D2 components of the multispecific antigen-binding molecules of the present invention may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The multispecific antigen-binding molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The multispecific antigen-binding molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Bispecific Antibodies

According to certain embodiments, the multispecific antigen-binding molecules of the invention are bispecific antibodies; e.g., bispecific antibodies comprising an antigen-binding arm that specifically binds a target molecule (T) and an antigen-binding arm that specifically binds an internalizing effector protein (E). Methods for making bispecific antibodies are known in the art and may be used to construct multispecific antigen-binding molecules of the present invention. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats).

Multimerizing Components

The multispecific antigen-binding molecules of the present invention, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the multispecific antigen-binding molecules of the present invention comprise two multimerizing domains, M1 and M2, wherein D1 is attached to M1 and D2 is attached to M2, and wherein the association of M1 with M2 facilitates the physical linkage of D1 and D2 to one another in a single multispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

Internalizing Effector Proteins (E)

In the context of the present invention, the D2 component of the multispecific antigen-binding molecule specifically binds an internalizing effector protein ("E"). An internalizing effector protein is a protein that is capable of being internalized into a cell or that otherwise participates in or contributes to retrograde membrane trafficking. In some instances, the internalizing effector protein is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of D2 to an internalizing effector protein causes the entire multispecific antigen-binding molecule, and any molecules associated therewith (e.g., a target molecule bound by D1), to also become internalized into the cell. As explained below, internalizing effector proteins include proteins that are directly internalized into a cell, as well as proteins that are indirectly internalized into a cell.

Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway. Specific non-limiting examples of internalizing effector proteins that are directly internalized into a cell include, e.g., CD63, MHC-I (e.g., HLA-B27), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (Myelin And Lymphocyte protein, a.k.a. VIP17), IGF2R, vacuolar-type $H^+$ ATPase, diphtheria toxin receptor, folate receptor, glutamate receptors, glutathione receptor, leptin receptors, scavenger receptors (e.g., SCARA1-5, SCARB1-3, CD36), etc.

In certain embodiments, the internalizing effector protein is prolactin receptor (PRLR). It was discovered that PRLR is, not only a target for certain therapeutic applications, but is also an effective internalizing effector protein on the basis of its high rate of internalization and turn-over. The potential for PRLR as an internalizing effector protein, for example, is illustrated in WO2015/026907, where it is demonstrated, inter alia, that anti-PRLR antibodies are effectively internalized by PRLR-expressing cells in vitro.

In embodiments in which E is a directly internalized effector protein, the D2 component of the multispecific antigen-binding molecule can be, e.g., an antibody or antigen-binding fragment of an antibody that specifically binds E, or a ligand or portion of a ligand that specifically interacts with the effector protein. For example, if E is Kremen-1 or Kremen-2, the D2 component can comprise or consist of a Kremen ligand (e.g., DKK1) or Kremen-binding portion thereof. As another example, if E is a receptor molecule such as ASGR1, the D2 component can comprise or consist of a ligand specific for the receptor (e.g., asialoorosomucoid [ASOR] or Beta-GalNAc) or a receptor-binding portion thereof.

Internalizing effector proteins that are indirectly internalized into a cell include proteins and polypeptides that do not internalize on their own, but become internalized into a cell after binding to or otherwise associating with a second protein or polypeptide that is directly internalized into the cell. Proteins that are indirectly internalized into a cell include, e.g., soluble ligands that are capable of binding to an internalizing cell surface-expressed receptor molecule. A non-limiting example of a soluble ligand that is (indirectly) internalized into a cell via its interaction with an internalizing cell surface-expressed receptor molecule is transferrin. In embodiments wherein E is transferrin (or another indirectly internalized protein), the binding of D2 to E, and the interaction of E with transferrin receptor (or another internalizing cell-surface expressed receptor molecule), causes the entire multispecific antigen-binding molecule, and any molecules associated therewith (e.g., a target molecule bound by D1), to become internalized into the cell concurrent with the internalization of E and its binding partner.

In embodiments in which E is an indirectly internalized effector protein such as a soluble ligand, the D2 component of the multispecific antigen-binding molecule can be, e.g., an antibody or antigen-binding fragment of an antibody that specifically binds E, or a receptor or portion of a receptor that specifically interacts with the soluble effector protein. For example, if E is a cytokine, the D2 component can comprise or consist of the corresponding cytokine receptor or ligand-binding portion thereof.

Target Molecules (T)

In the context of the present invention, the D1 component of the multispecific antigen-binding molecule specifically binds a target molecule ("T"). A target molecule is any protein, polypeptide, or other macromolecule whose activity or extracellular concentration is desired to be attenuated, reduced or eliminated. In many instances, the target molecule to which D1 binds is a protein or polypeptide [i.e., a "target protein"]; however, the present invention also includes embodiments wherein the target molecule ("T") is a carbohydrate, glycoprotein, lipid, lipoprotein, lipopolysaccharide, or other non-protein polymer or molecule to which D1 binds. According to the present invention, T can be a cell surface-expressed target protein or a soluble target protein. Target binding by the multispecific antigen-binding molecule may take place in an extracellular or cell surface context. In certain embodiments, however, the multispecific antigen-binding molecule binds a target molecule inside the cell, for example within an intracellular component such as the endoplasmic reticulum, Golgi, endosome, lysosome, etc.

Examples of cell surface-expressed target molecules include cell surface-expressed receptors, membrane-bound ligands, ion channels, and any other monomeric or multimeric polypeptide component with an extracellular portion that is attached to or associated with a cell membrane. Non-limiting, exemplary cell surface-expressed target molecules that may be targeted by the multispecific antigen-binding molecule of the present invention include, e.g., cytokine receptors (e.g., receptors for IL-1, IL-4, IL-6, IL-13, IL-22, IL-25, IL-33, etc.), as well as cell surface targets including other type 1 transmembrane receptors such as PRLR, G-protein coupled receptors such as GCGR, ion channels such as Nav1.7, ASIC1 or ASIC2, non-receptor surface proteins such as MHC-I (e.g., HLA-B*27), etc.

In embodiments in which T is a cell surface-expressed target protein, the D1 component of the multispecific antigen-binding molecule can be, e.g., an antibody or antigen-binding fragment of an antibody that specifically binds T, or a ligand or portion of a ligand that specifically interacts with the cell surface-expressed target protein. For example, if T is IL-4R, the D1 component can comprise or consist of IL-4 or a receptor-binding portion thereof.

Examples of soluble target molecules include cytokines, growth factors, and other ligands and signaling proteins. Non-limiting exemplary soluble target protein that may be targeted by the multispecific antigen-binding molecule of the present invention include, e.g., IL-1, IL-4, IL-6, IL-13, IL-22, IL-25, IL-33, SOST, DKK1, etc. Soluble targets molecules also include, e.g., non-human target molecules such as allergens (e.g., Fel D1, Betv1, CryJ1), pathogens (e.g., *Candida albicans, S. aureus,* etc.), and pathogenic molecules (e.g., lipopolysaccharide [LPS], lipotechoic acid [LTA], Protein A., toxins, etc.). In embodiments in which T is a soluble target molecule, the D1 component of the multispecific antigen-binding molecule can be, e.g., an antibody or antigen-binding fragment of an antibody that specifically binds T, or a receptor or portion of a receptor that specifically interacts with the soluble target molecule. For example, if T is IL-4, the D1 component can comprise or consist of IL-4R or a ligand-binding portion thereof.

Target molecules also include tumor-associated antigens, as described elsewhere herein.

PH-Dependent Binding

The present invention provides multispecific antigen-binding molecules comprising a first antigen-binding domain (D1) and a second antigen-binding domain (D2), wherein one or both of the antigen-binding domains (D1 and/or D2) binds its antigen (T or E) in a pH-dependent manner. For example, an antigen-binding domain (D1 and/or D2) may exhibit reduced binding to its antigen at acidic pH as compared to neutral pH. Alternatively, an antigen-binding domain (D1 and/or D2) may exhibit enhanced binding to its antigen at acidic pH as compared to neutral pH. Antigen-binding domains with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antigen-binding domains with pH-dependent characteristics. For example, by substituting one or more amino acid of an antigen-binding domain (e.g., within a CDR) with a histidine residue, an antigen-binding domain with reduced antigen-binding at acidic pH relative to neutral pH may be obtained.

In certain embodiments, the present invention includes multispecific antigen-binding molecules comprising a D1 and/or D2 component that binds its respective antigen (T or E) at acidic pH with a $K_D$ that is at least about 3, 5, 10, 11, 12, 13, 14, 15, 16, 17, 18, 19, 20, 25, 30, 35, 40, 45, 50, 55, 60, 65, 70, 75, 80, 85, 90, 95, 100, or more times greater than the $K_D$ of the D1 and/or D2 component for binding to its respective antigen at neutral pH. pH dependent binding may also be expressed in terms of the $t_{1/2}$ of the antigen-binding domain for its antigen at acidic pH compared to neutral pH. For example, the present invention includes multispecific antigen-binding molecules comprising a D1 and/or D2 component that binds its respective antigen (T or E) at acidic pH with a $t_{1/2}$ that is at least about 5, 6, 7, 8, 9, 10, 15, 20, 25, 30, 35, 40, 45, 50, 55, 60, or more times shorter than the $t_{1/2}$ of the D1 and/or D2 component for binding to its respective antigen at neutral pH.

Multispecific antigen-binding molecules of the present invention that comprise a D1 and/or D2 component with reduced antigen binding at acidic pH as compared to neutral pH, when administered to animal subjects, may in certain embodiments exhibit slower clearance from circulation as compared to comparable molecules that do not exhibit pH-dependent binding characteristics. According to this aspect of the invention, multispecific antigen-binding molecules with reduced antigen binding to either T and/or E at acidic pH as compared to neutral pH are provided which exhibit at least 2 times slower clearance from circulation relative to comparable antigen-binding molecules that do not possess reduced antigen binding at acidic pH as compared to neutral pH. Clearance rate can be expressed in terms of the half-life of the antibody, wherein a slower clearance correlates with a longer half-life.

As used herein, the expression "acidic pH" means a pH of 6.0 or less. The expression "acidic pH" includes pH values of about 6.0, 5.95, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Attenuation of Target Molecule Activity

As noted elsewhere herein, and as demonstrated by the working Examples herein below, the present inventors have discovered that the simultaneous binding of a target molecule (T) and an internalizing effector protein (E) by a multispecific antigen-binding molecule attenuates the activity of T to a greater extent than the binding of T by the first antigen-binding domain (D1) component of the multispecific antigen-binding molecule alone. As used herein, the expression "attenuates the activity of T to a greater extent than the binding of T by D1 alone" means that, in an assay in which the activity of T can be measured using cells that express E, the level of T activity measured in the presence of a multispecific antigen-binding molecule is at least 10% lower than the level of T activity measured in the presence of a control construct containing D1 by itself (i.e., not physically linked to the second antigen-binding domain (D2)). For instance, the level of T activity measured in the presence of the multispecific antigen-binding molecule may be about 10%, 15%, 20%, 25%, 30%, 35%, 40%, 45%, 50%, 55%, 60%, 65%, 70%, 75%, 80%, 85%, 90%, 95%, or 100% lower than the level of T activity measured in the presence of a control construct containing D1 by itself.

A non-limiting, illustrative assay format for determining whether a multispecific antigen-binding molecule attenuates the activity of a target molecule to a greater extent than the binding of the target molecule by the D1 domain alone is shown in working Examples 1 and 2, herein below. In Example 1, for instance, "T" is the interleukin-4 receptor (IL-4R), and "E" is CD63. The multispecific antigen-binding molecule of Example 1 is a 2-antibody conjugate comprising an anti-IL-4R mAb linked to an anti-CD63 mAb via a streptavidin/biotin linker. Thus, "D1" in this exemplary construct is the antigen-binding domain (HCVR/LCVR pair) of the anti-IL-4R antibody, and "D2" is the antigen-binding domain (HCVR/LCVR pair) of the anti-CD63 antibody. For the experiments of Examples 1 and 2, a cell-based assay format was used that produces a reporter signal when IL-4R activity is stimulated by the addition of exogenous IL-4 ligand. The amount of IL-4-induced reporter activity detected in the presence of the multispecific antigen-binding molecule was compared to the amount of IL-4-induced reporter activity detected in the presence of control constructs containing the anti-IL-4R antibody either connected to an irrelevant control immunoglobulin (control 1), or combined with, but not physically connected to, the anti-CD63 antibody (control 2). The control constructs thus produce the condition in which T is bound by D1 alone (i.e., wherein D1 is not a part of the multispecific antigen-binding molecule per se). If the extent of target molecule activity (represented by the reporter signal) observed in the presence of the multispecific antigen-binding molecule is at least 10% less than the amount of target molecule activity observed in the presence of a control construct comprising the D1 component not physically linked to the D2 component (e.g., control 1 or control 2), then for purposes of the present disclosure, it is concluded that "the simultaneous binding of T and E by the multispecific antigen-binding molecule attenuates the activity of T to a greater extent than the binding of T by D1 alone."

The binding of T by D1 alone may, in some embodiments, result in partial attenuation of the activity of T (as in the case of Example 1 where the treatment of reporter cells with an anti-IL-4R antibody alone [i.e., controls 1 and 2] caused a small level of attenuation of IL-4 signaling relative to untreated cells). In other embodiments, the binding of T by D1 alone will result in no detectable attenuation of the activity of T; that is, the biological activity of T may be unaffected by the binding of T by D1 alone. In any event, however, the simultaneous binding of T and E by a multispecific antigen-binding molecule of the invention will attenuate the activity of T to a greater extent than the binding of T by D1 alone.

Alternative assay formats and variations on the assay format(s) exemplified herein will be apparent to persons of ordinary skill in the art, taking into account the nature of the specific target molecule and effector proteins to which any given multispecific antigen-binding molecule may be directed. Any such format can be used in the context of the present invention to determine whether the simultaneous binding of T and E by a multispecific antigen-binding molecule attenuates the activity of T to a greater extent than the binding of T by D1 alone.

Tumor Targeting

In another aspect of the invention, the multispecific antigen-binding molecules are useful for targeting tumor cells. According to this aspect of the invention, the target molecule "T" to which D1 binds is a tumor-associated antigen. In certain instances, the tumor-associated antigen is an antigen that is not ordinarily internalized. The internalizing effector protein "E" to which D2 binds may be tumor specific, or it may be expressed on both tumor and non-tumor cells of an individual. Any of the internalizing effector proteins mentioned elsewhere herein may be targeted for anti-tumor applications of the invention.

As used herein, the term "tumor-associated antigen" includes proteins or polypeptides that are preferentially expressed on the surface of a tumor cell. The expression "preferentially expressed," as used in this context, means that the antigen is expressed on a tumor cell at a level that is at least 10% greater (e.g., 10%, 20%, 30%, 40%, 50%, 60%, 70%, 80%, 90%, 100%, 110%, 150%, 200%, 400%, or more) than the expression level of the antigen on non-tumor cells. In certain embodiments, the target molecule is an antigen that is preferentially expressed on the surface of a tumor cell selected from the group consisting of a renal tumor cell, a colon tumor cell, a breast tumor cell, an ovarian tumor cell, a skin tumor cell, a lung tumor cell, a prostate tumor cell, a pancreatic tumor cell, a glioblastoma cell, a head and neck tumor cell and a melanoma cell. Non-limiting examples of specific tumor-associated antigens include, e.g., AFP, ALK, BAGE proteins, β-catenin, brc-abl, BRCA1, BORIS, CA9, carbonic anhydrase IX, caspase-8, CD40, CDK4, CEA, CTLA4, cyclin-B1, CYP1B1, EGFR, EGFRvIII, ErbB2/Her2, ErbB3, ErbB4, ETV6-AML, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

The multispecific antigen-binding molecule, according to this aspect of the invention, may be conjugated to a drug, toxin, radioisotope, or other substance which is detrimental to the viability of a cell. Alternatively, the drug or toxin may be a substance which does not directly kill a cell, but renders a cell more susceptible to killing by other external agents. In yet other embodiments involving tumor targeting, the multispecific antigen-binding molecule of the invention is not itself conjugated to a drug, toxin or radioisotope, but instead is administered in combination with a second antigen-binding molecule specific for the target (T) (herein referred to as an "accomplice molecule"), wherein the accomplice molecule is conjugated to a drug, toxin or radioisotope. In such embodiments, the multispecific antigen binding molecule will preferably bind to an epitope on the target molecule (T) that is distinct from and/or non-overlapping with the epitope recognized by the accomplice molecule (i.e., to allow for simultaneous binding of the multispecific antigen-binding molecule and the accomplice molecule to the target).

In a related embodiment, the present invention also includes anti-tumor combinations, and therapeutic methods, comprising: (a) a toxin- or drug-conjugated antigen-binding molecule that specifically binds a tumor-associated antigen; and (b) a multispecific antigen-binding molecule comprising (i) a first binding domain that specifically binds an internalizing effector protein (e.g., with low affinity) and (ii) a second binding domain that specifically binds the toxin- or drug-conjugated antigen-binding molecule. In this embodiment, the multispecific antigen-binding molecule functions to link the toxin- or drug-conjugated antigen-binding molecule to the internalizing effector protein, which thereby functions to physically link the tumor associated antigen to the internalizing effector protein. Internalization of the toxin-labeled anti-tumor-associated antigen antibody via its connection to the internalizing effector protein would consequently result in targeted tumor cell killing.

According to certain embodiments of the tumor-targeting aspects of the invention, the multispecific antigen-binding molecule (or accomplice antibody) may be conjugated to one or more cytotoxic drugs selected from the group consisting of: calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, larotaxel, tesetaxel, orataxel, docetaxel, dolastatin 10, auristatin E, auristatin PHE and maytansine-based compounds (e.g., DM1, DM4, etc.). The multispecific antigen-binding molecule (or accomplice antibody) may also, or alternatively, be conjugated to a toxin such as diphtheria toxin, *Pseudomonas aeruginosa* exotoxin A, ricin A chain, abrin A chain, modeccin A chain, alpha-sarcin, *Aleurites fordii* proteins, dianthin proteins, *Phytolaca americana* proteins, etc. The multispecific antigen-binding molecule (or accomplice antibody) may also, or alternatively, be conjugated to one or more radioisotope selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{121}$Pb, $^{224}$Ra and $^{223}$Ra. Thus, this aspect of the invention includes multispecific antigen-binding molecules that are antibody-drug conjugates (ADCs) or antibody-radioisotope conjugates (ARCs).

In the context of tumor killing applications, the D2 component may, in certain circumstances, bind with low affinity to the internalizing effector protein "E". Thus, the multispecific antigen-binding molecule will preferentially target tumor cells that express the tumor-associated antigen. As used herein, "low affinity" binding means that the binding affinity of the D2 component for the internalizing effector protein (E) is at least 10% weaker (e.g., 15% weaker, 25% weaker, 50% weaker, 75% weaker, 90% weaker, etc.) than the binding affinity of the D1 component for the target molecule (T). In certain embodiments, "low affinity" binding means that the D2 component interacts with the internalizing effector protein (E) with a $K_D$ of greater than about 10 nM to about 1 μM, as measured in a surface plasmon resonance assay at about 25° C.

The simultaneous binding of a multispecific antigen-binding molecule to an internalizing effector protein and a tumor-associated antigen will result in preferential internalization of the multispecific antigen-binding molecule into tumor cells. If, for example, the multispecific antigen-binding molecule is conjugated to a drug, toxin or radioisotope (or if the multispecific antigen-binding molecule is administered in combination with an accomplice antibody that is conjugated to a drug, toxin or radioisotope), the targeted internalization of the tumor-associated antigen into the tumor cell via its linkage to the multispecific antigen-binding molecule, will result in extremely specific tumor cell killing.

Pharmaceutical Compositions and Administration Methods

The present invention includes pharmaceutical compositions comprising a multispecific antigen-binding molecule. The pharmaceutical compositions of the invention can be formulated with suitable carriers, excipients, and other agents that provide improved transfer, delivery, tolerance, and the like.

The present invention also includes methods for inactivating or attenuating the activity of a target molecule (T). The methods of the present invention comprise contacting a target molecule with a multispecific antigen-binding molecule as described herein. In certain embodiments, the methods according to this aspect of the invention comprise administering a pharmaceutical composition comprising a multispecific antigen-binding molecule to a patient for whom it is desirable and/or beneficial to inactivate, attenuate, or otherwise decrease the extracellular concentration of a target molecule.

Various delivery systems are known in the art and can be used to administer the pharmaceutical compositions of the present invention to a patient. Methods of administration that can be used in the context of the present invention include, but are not limited to, intradermal, intramuscular, intraperitoneal, intravenous, subcutaneous, intranasal, epidural, and oral routes. The pharmaceutical compositions of the invention may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. For example, a pharmaceutical composition of the present invention can be delivered subcutaneously or intravenously with a standard needle and syringe. In addition, with respect to subcutaneous delivery, a pen delivery device can be used to administer a pharmaceutical composition of the present invention to a patient.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Use of a Multispecific Antigen-Binding Molecule to Induce Degradation of a Cell Surface Receptor via Linkage with an Internalizing Effector Protein As an initial proof-of-concept experiment, a multispecific antigen-binding molecule was created which is capable of binding (a) an internalizing effector molecule and (b) a cell surface receptor target molecule. In this Example, the internalizing effector protein is Kremen-2 (Krm2), and the cell surface receptor target molecule is an Fc receptor (FcγR1 [Fc-gamma-R1]).

Kremen molecules (Krm1 and Krm2) are cell-surface proteins known to mediate WNT signaling by directing the internalization and degradation of the WNT pathway signaling molecules LRP5 and LRP6. Internalization of LRP5/6 is accomplished via the soluble interacting protein DKK1. In particular, DKK1 links Kremen to LRP5/6 on the cell surface, and because of this linkage, the internalization of Kremen drives the internalization and degradation of LRP5 and LRP6. (See Li et al., PLoS One 5(6):e11014).

The present inventors sought to exploit the Kremen-binding properties of DKK1 and the internalization properties of Kremen to induce the internalization of FcγR1. To facilitate Kremen-mediated internalization/degradation of FcγR1, a multispecific antigen-binding molecule was constructed consisting of DKK1 fused to a mouse Fc (DKK1-mFc, having the amino acid sequence of SEQ ID NO:1). As explained elsewhere herein, a multispecific antigen-binding molecule is defined as a molecule comprising a first antigen-binding domain (D1) which specifically binds a target molecule, and a second antigen-binding domain (D2) which specifically binds an internalizing effector protein. In this proof-of-concept Example, the "first antigen-binding domain" is the mFc component which specifically binds the target molecule FcγR1, and the "second antigen-binding domain" is the DKK1 component which specifically binds the internalizing effector protein Kremen.

An experiment was first conducted to determine whether DKK1-mFc can be endocytosed into cells in a Kremen-dependent manner. For this experiment, two cell lines were used: Cell-1, an HEK293 cell line engineered to express FcγR1 but not Kremen-2, and Cell-2, an HEK293 cell line engineered to express both FcγR1 and Kremen-2. A 1:10 dilution of DKK1-mFc conditioned medium was added to the respective cell lines and allowed to incubate at 37° C. for 90 minutes. After the 90 minute incubation, cells were stained with Alexa-488-labeled anti-mouse IgG antibody to detect the DKK1-mFc molecule. Using fluorescence microscopy, it was observed that virtually no DKK1-mFc was localized inside Cell-1 (lacking Kremen); however, substantial amounts of DKK1-mFc were detected within Cell-2 which expresses Kremen-2. Thus, these results show that the multispecific antigen-binding molecule DKK1-mFc can be internalized into cells in a Kremen-dependent manner.

Next, a time-course experiment was conducted to determine whether DKK1-mFc can induce FcγR1 degradation in a Kremen-dependent manner. A brief description of the experimental protocol is as follows: Cell-1 (expressing only FcγR1) and Cell-2 (expressing Kremen-2 and FcγR1) were treated with 2 mg/ml NHS-Sulfo-Biotin for 15 minutes on ice to label all cell surface expressed proteins. Cells were then washed and resuspended in 400 µl of medium and divided into four-100 µl aliquots which were treated with DKK1-mFc for varying amounts of time (0 min, 15 min, 30 min and 60 min) at 37° C. Following DKK1-mFc incubation, cells were pelleted and treated with protease inhibitors. Lysates of the cells from the different incubation time points were subjected to FcγR1 immunoprecipitation. For the FcγR1 immunoprecipitation, mouse anti-FcγR1 antibody was added to cell lysates and incubated for 1 hour at 4° C. Then Protein-G beads were added and the mixture was incubated for 1 hour at 4° C. The beads were then washed and the proteins eluted and subjected to SDS-PAGE. Proteins were transferred to membrane and probed with HRP-labeled streptavidin to reveal relative amounts of remaining surface-exposed FcγR1 protein in each sample. Results are shown in FIG. 2.

Figure 2:
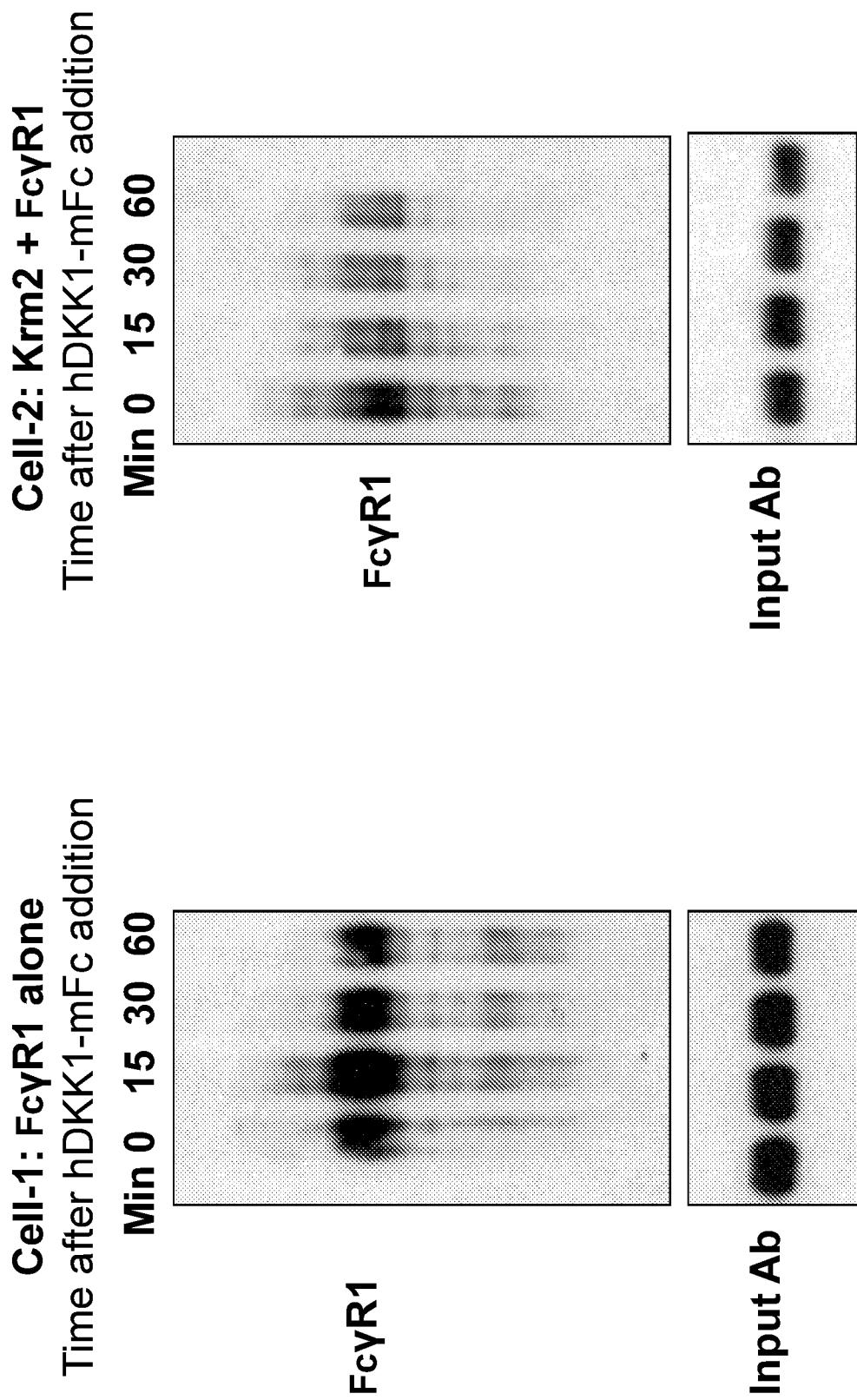
FIG. 2 shows the results of an immunoprecipation experiment performed on two different cells (Cell-1 expressing FcγR1 alone, and Cell-2 expressing Krm2 and FcγR1) following incubation for different amounts of time (0, 15, 30 and 60 minutes) with a DKK1-mFc multispecific antigen-binding molecule.

As illustrated in FIG. 2, the amount of surface-exposed FcγR1 protein in Cell-1 samples (expressing FcγR1 but not Kremen-2) remained relatively constant regardless of the amount of time the cells were exposed to DKK1-mFc. By contrast, the amount of surface-exposed FcγR1 protein in Cell-2 samples (expressing both Kremen-2 and FcγR1) decreased substantially with increasing incubation times with DKK1-mFc. Thus, this experiment demonstrates that DKK1-mFc induces degradation of cell surface expressed FcγR1 in a Kremen-2-dependent manner.

Taken together, the foregoing results show that a multispecific antigen-binding molecule that simultaneously binds a cell surface target molecule (FcγR1) and an internalizing effector protein (Kremen-2), can induce degradation of the target molecule in an effector protein-dependent manner.

Example 2. IL-4R Activity is Attenuated Using a Multispecific Antigen-Binding Molecule with Specificity for IL-4R and CD63

In a further set of proof-of-concept experiments, a multispecific antigen-binding molecule was constructed which is capable of simultaneously binding a cell surface-expressed target molecule (i.e., IL-4R) and a cell surface-expressed internalizing effector protein (i.e., CD63). The purpose of these experiments was to determine whether IL-4R activity on a cell can be attenuated to a greater extent by physically linking IL-4R to an effector molecule that is internalized and targeted for degradation within the lysosome (in this case, CD63). In other words, this Example was designed to test whether the normal internalization and degradation of CD63 could be used to force the internalization and degradative rerouting of IL-4R within a cell.

First, a multispecific antigen-binding molecule was constructed that is able to bind both IL-4R and CD63. Specifically, a streptavidin-conjugated anti-IL-4R antibody and a biotinylated anti-CD63 antibody were combined in a 1:1 ratio to produce an anti-IL-4R:anti-CD63 conjugate (i.e., a multispecific antigen-binding molecule that specifically binds both IL-4R and CD63). The anti-IL-4R antibody used in this Example is a fully human mAb raised against the IL-4R extracellular domain. (The anti-IL-4R antibody comprised a heavy chain variable region having SEQ ID NO:3 and a light chain variable region having SEQ ID NO:4). The anti-CD63 antibody used in this Example is the mouse anti-human CD63 mAb clone MEM-259, obtained from Biolegend (San Diego, Calif.), catalog. No. 312002.

Two control constructs were also created: Control-1=streptavidin-conjugated anti-IL-4R antibody combined in a 1:1 ratio with biotinylated control mouse IgG1kappa antibody; and Control-2=streptavidin-conjugated anti-IL-4R antibody combined in a 1:1 ratio with non-biotinylated anti-CD63 antibody. The anti-IL-4R antibody used in the experimental and control constructs for this Example is an antibody that is known to specifically bind IL-4R and only partially block IL-4-mediated signaling.

The experimental cell line used in this Example is an HEK293 cell line containing a STAT6-luciferase reporter construct and additional STAT6 ("HEK293/STAT6-luc cells"). The cells used in this experiment express both IL-4R and CD63 on their surface. When treated with IL-4 in the absence of any inhibitors, this cell line produces a dose-dependent detectable chemiluminescence signal which reflects the extent of IL-4-mediated signaling.

Figure 3:
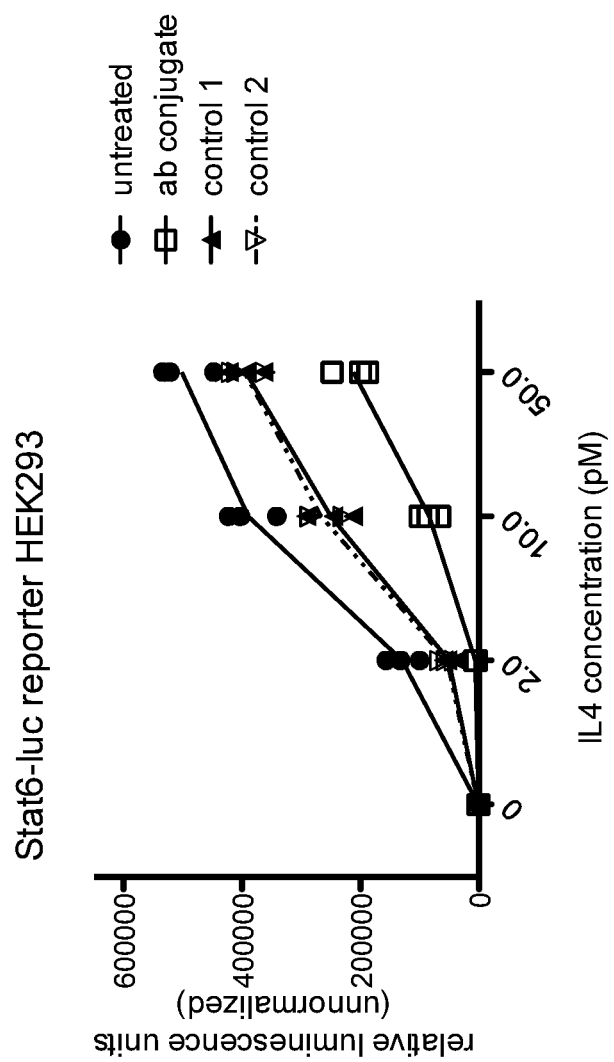
FIG. 3 shows the relative IL-4-induced luminescence produced by Stat6-luc reporter HEK293 cells in the presence and absence of an anti-IL-4R/anti-CD63 multispecific antigen binding protein ("ab conjugate") or control constructs ("control 1" and "control 2") at various concentrations of IL-4.

In an initial experiment, the experimental anti-IL-4R/anti-CD63 multispecific molecule, or the control constructs, were added to the HEK293/STAT6-luc cells so that the final concentration of anti-IL-4R antibody in the media was 12.5 nM. Reporter signal was measured at increasing concentrations of IL-4 in the presence and absence of the experimental and control constructs (FIG. 3). As seen in FIG. 3, The anti-IL-4R/anti-CD63 multispecific molecule ("ab conjugate") inhibited IL-4-mediated signaling to a significantly greater extent than either control construct.

Figure 4:
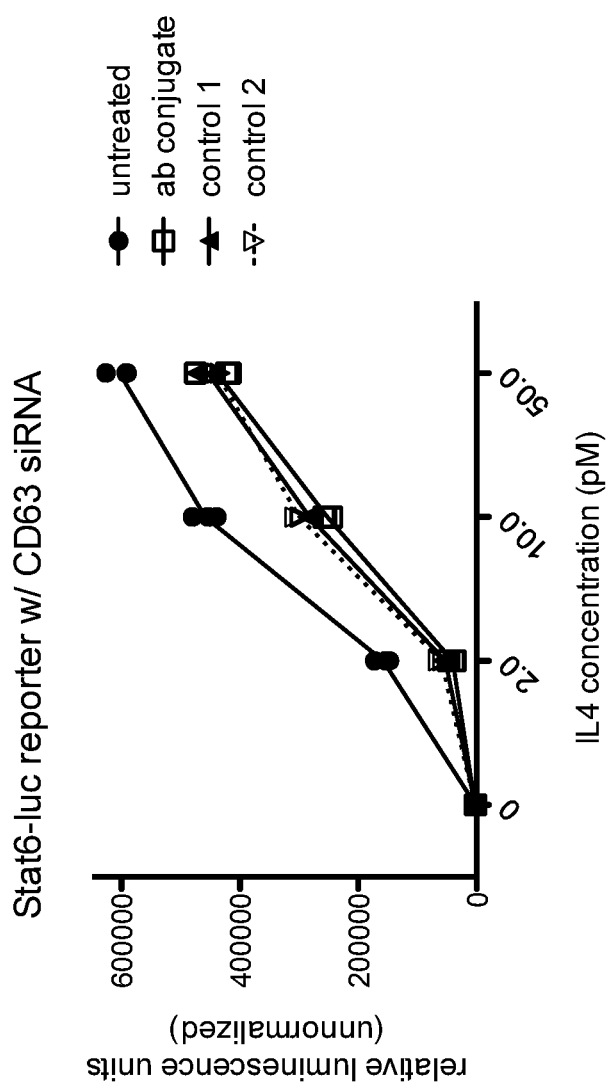
FIG. 4 shows the results of an experiment carried out in the same manner as the experiment shown in FIG. 3, except that CD63 expression was significantly reduced in the reporter cell line by an siRNA directed against CD63.

To confirm that the effect observed in FIG. 3 was dependent on CD63, the same experiment described above was carried out, except that CD63 expression was significantly reduced in the reporter cell line using an siRNA directed against CD63. With CD63 expression significantly reduced, the enhanced inhibitory activity of the anti-I L-4R/anti-CD63 multispecific molecule was no longer observed (FIG. 4). This result suggests that the ability of the anti-IL-4R/anti-CD63 multispecific molecule to attenuate IL-4-mediated signaling is due to the simultaneous binding of the multispecific molecule to IL-4R and CD63 and the consequent internalization and degradation of the entire antibody-IL-4R-CD63 complex.

Figure 5:
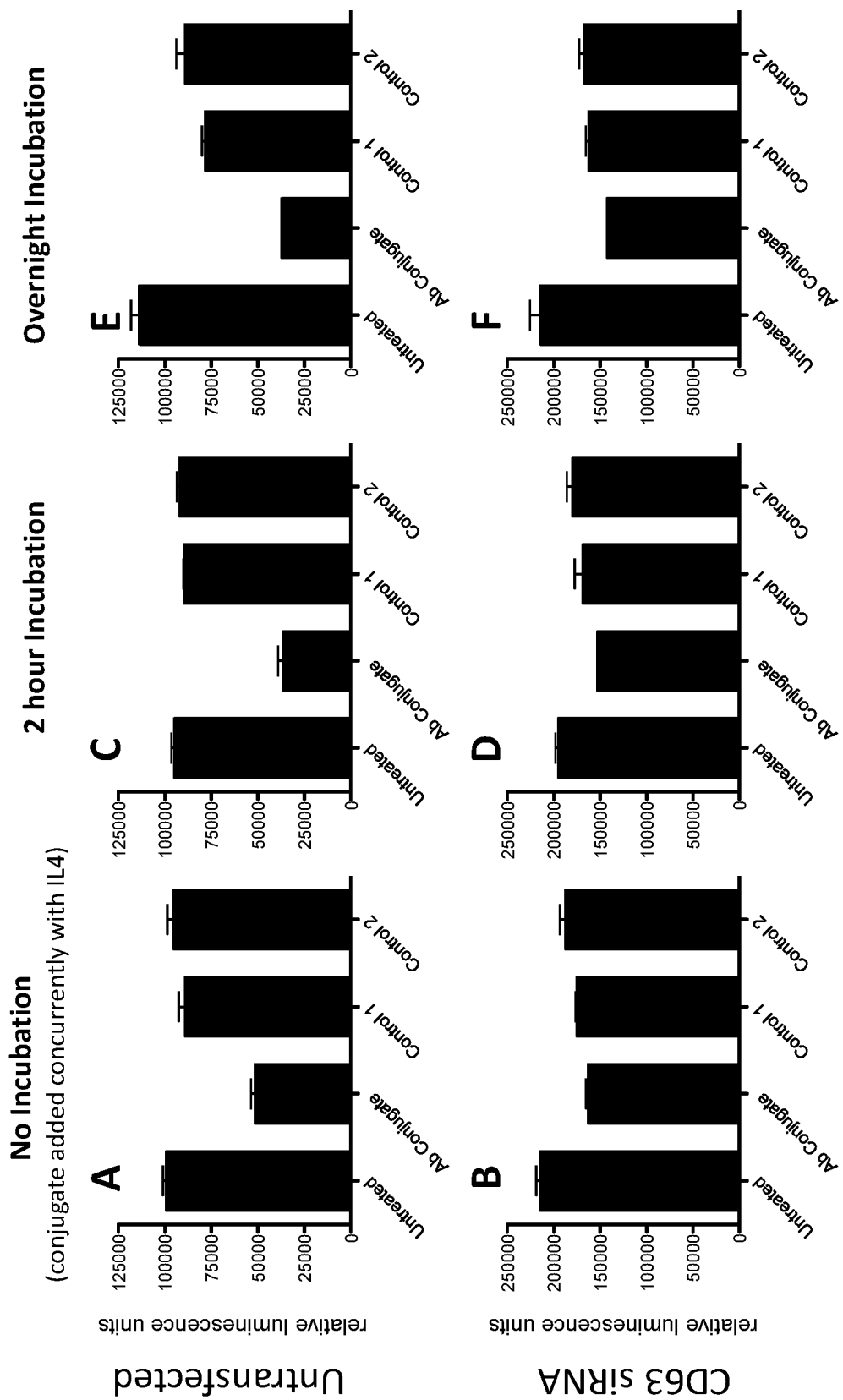
FIG. 5 shows the results of an experiment carried out in a similar manner as the experiments shown in FIGS. 3 and 4, except that the reporter cells were incubated with the multispecific antigen binding protein ("Ab conjugate") or control constructs ("control 1" and "control 2") at time zero (panels A and B), for 2 hours (panels C and D) or overnight (panels E and F) prior to the addition of IL-4 ligand. The top row of bar graphs (panels A, C, and E) represent the results of experiments conducted in cells expressing normal levels of CD63 ("untransfected"), while the bottom row of bar graphs (panels B, D, and F) represents the results of experiments conducted in cells in which CD63 expression was significantly reduced in the reporter cell line by an siRNA directed against CD63.

Similar experiments were next carried out in which the anti-IL-4R/anti-CD63 multispecific molecule, or the control constructs, were allowed to incubate with the HEK293/STAT6-luc reporter cell line for various amounts of time prior to the addition of IL-4. In a first set of such experiments, the molecules were allowed to incubate with the reporter cell line for 0 hours (i.e., added concurrently with IL-4), 2 hours, or overnight prior to the addition of 50 pM IL-4. Luciferase activity was measured six hours after the addition of IL-4. Results are shown in FIG. 5, top panel ("untransfected"). In a further set of experiments, a similar protocol was carried out, except that the experimental or control molecules were allowed to incubate with the reporter cell line for 15 minutes, 30 minutes, 1 hour or 2 hours prior to the addition of 50 pM IL-4. Results are shown in FIG. 6.

Figure 6:
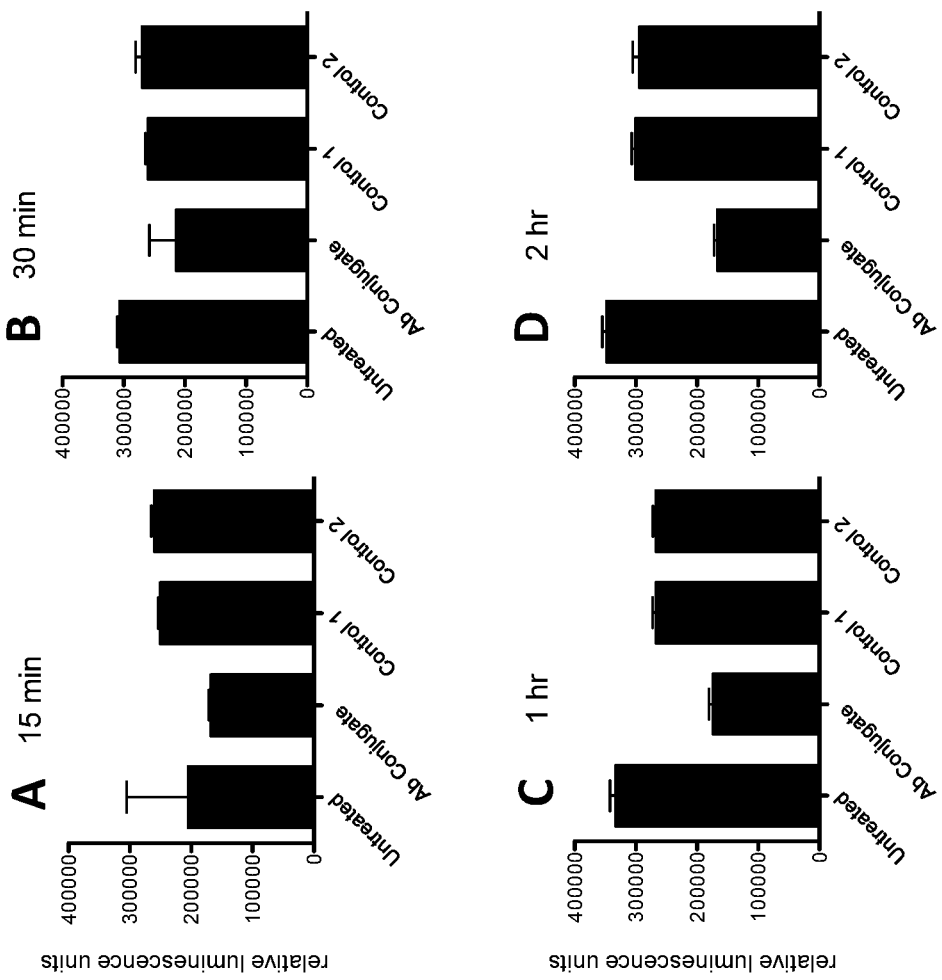
FIG. 6 shows the results of an experiment carried out in a similar manner as the experiments shown in FIGS. 3 and 4, except that the reporter cells were incubated with the anti-IL-4R/anti-CD63 multispecific antigen binding protein ("Ab conjugate") or control constructs ("control 1" and "control 2") for 15 minutes (panel A), 30 minutes (panel B), 1 hour (panel C) or 2 hours (panel D) prior to the addition of IL-4 ligand.

The results summarized in FIGS. 5 and 6 show that the anti-IL-4R/anti-CD63 multispecific molecule is able to inhibit IL-4-mediated signaling, and that this inhibitory effect is enhanced with longer incubation times. As with the initial set of experiments, it was confirmed using CD63 siRNA that the inhibitory effect of the anti-IL-4R/anti-CD63 multispecific molecule was dependent on CD63 expression (FIG. 5 bottom panel ["CD63 siRNA"]).

In summary, this Example provides further proof-of-concept for the inhibition of a target molecule activity through the use of a multispecific antigen-binding molecule that is capable of simultaneously binding both the target molecule (in this case IL-4R) and an internalizing effector protein (in this case CD63) to thereby cause the internalization and degradative rerouting of the target molecule within a cell. Stated differently, the simultaneous binding of IL-4R and CD63 by the exemplary multispecific antigen-binding molecule attenuated the activity of IL-4R to a substantially greater extent (i.e., >10%) than the binding of IL-4R by the control constructs alone.

Example 3. An Anti-IL-4R x Anti-CD63 Bispecific Antibody Attenuates IL-4R Activity in a CD63-Dependent Manner The experiments of Example 2, herein, show that an anti-IL-4R/anti-CD63 multispecific molecule inhibits IL-4-mediated signaling in a CD63-dependent manner. In those experiments, the multispecific antigen-binding molecule consisted of two separate monoclonal antibodies (anti-IL-4R and anti-CD63) that were connected via a biotin-streptavidin linkage. To confirm that the results observed with that proof-of-concept multispecific antigen-binding molecule are generalizable to other multispecific antigen-binding molecule formats, a true bispecific antibody was constructed.

Standard bispecific antibody technology was used to construct a bispecific antibody consisting of a first arm specific for IL-4R and a second arm specific for CD63. The IL-4R-specific arm contained an anti-IL-4R heavy chain paired with a CD63-specific light chain. The CD63-specific light chain was paired with the IL-4R specific heavy chain solely for purposes of convenience of construction; nevertheless, the pairing of the anti-IL-4R heavy chain with the anti-CD63 light chain retained full specificity for IL-4R and did not exhibit binding to CD63. The CD63-specific arm contained an anti-CD63 heavy chain paired with an anti-CD63 light chain (the same light chain as used in the IL-4R arm). The anti-IL-4R heavy chain (comprising SEQ ID NO:3) was derived from the full anti-IL-4R antibody as used in Example 2; However, the anti-CD63 heavy and light chains were derived from the anti-CD63 antibody designated H5C6, obtained from the Developmental Studies Hybridoma Bank (University of Iowa Department of Biology, Iowa City, Iowa). As with the full anti-IL-4R antibody used in Example 2, the anti-IL-4R component of the bispecific antibody used in this Example exhibited only moderate IL-4R blocking activity on its own.

Figure 7:
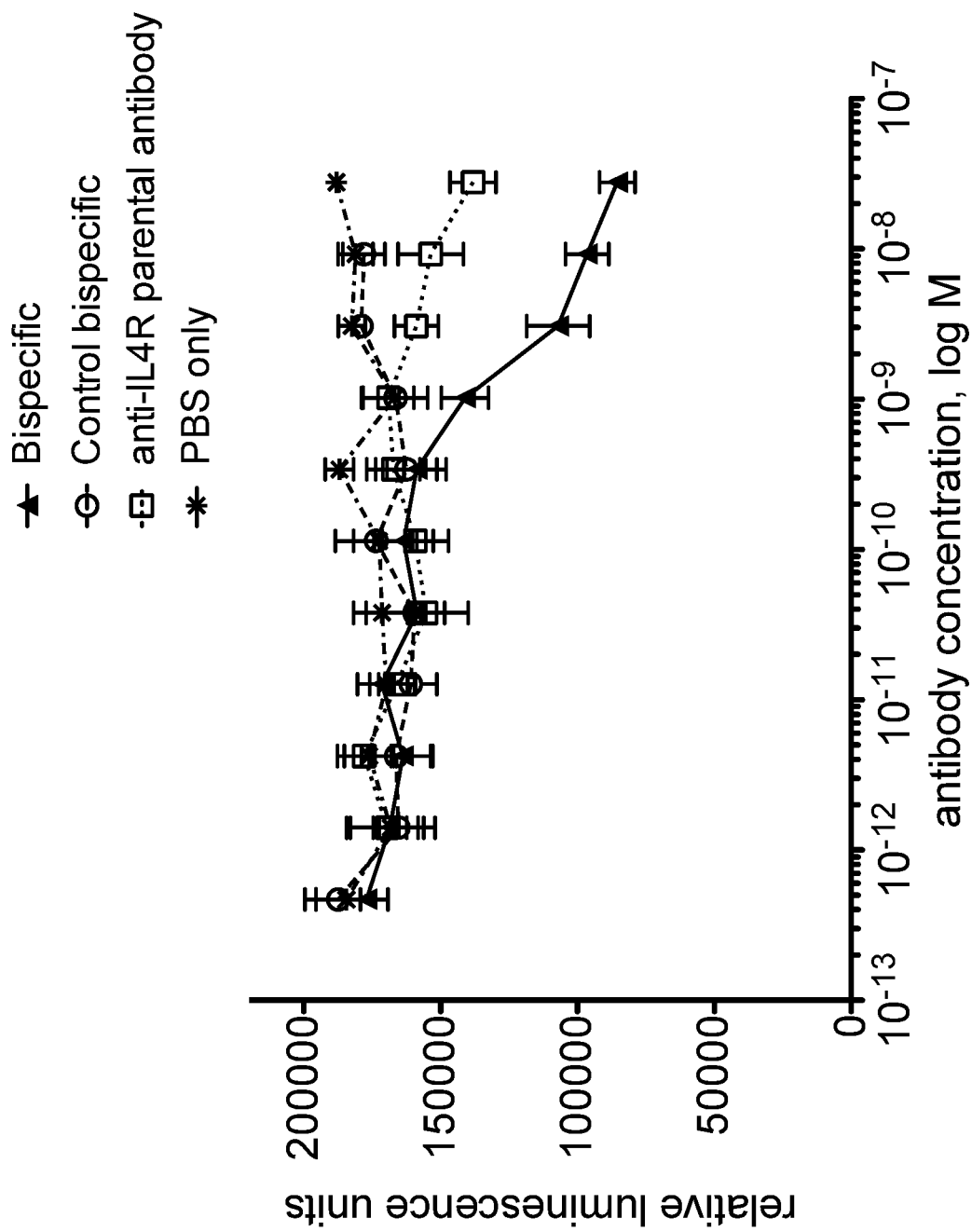
FIG. 7 shows the results of an experiment in which Stat6-luc reporter cells were treated with 10 pM IL-4 in the presence of various dilutions of an anti-IL-4R x anti-CD63 bispecific antibody ("bispecific"), or control constructs (anti-IL-4R monospecific, or mock bispecific that only binds IL-4R).

An IL-4 luciferase assay was carried out to assess the blocking activity of the anti-IL-4R x anti-CD63 bispecific antibody. Briefly, serial dilutions of anti-IL-4R x anti-CD63 bispecific antibody or control molecules were added to HEK293/STAT6-luc reporter cells (see Example 2). Under normal conditions, these cells produce a detectable luciferase signal when treated with IL-4. For this experiment, 10 pM IL-4 was then added to the cells, and luciferase activity was quantified for each dilution of antibody used. The controls used in this assay were: (a) mock bispecific antibody that binds IL-4R with one arm and has a non-functional anti-CD63 arm (i.e., containing one anti-IL-4R heavy chain and one anti-CD63 heavy chain, both paired with the anti-IL-4R light chain); (b) anti-IL-4R monospecific antibody; and (c) buffer (PBS) only (without antibody). Results are shown in FIG. 7. As shown in FIG. 7, for the control samples used, luciferase activity remained relatively high even at the highest antibody concentrations, whereas for the bispecific antibody, luciferase activity declined significantly as antibody concentration increased. These results confirm that simultaneous binding of IL-4R and CD63 by a bispecific antibody causes substantial inhibition of IL-4R activity.

Example 4. Internalization of SOST Using a Multispecific Antigen-Binding Molecule That Simultaneously Binds SOST and CD63

In this Example, the ability of multispecific antigen-binding molecules to promote the internalization of the soluble target molecule SOST (sclerostin) was assessed. For these experiments, the target molecule was a fusion protein consisting of a human SOST protein tagged with a pHrodo™ moiety (Life Technologies, Carlsbad, Calif.) and a myc tag. The pHrodo™ moiety is a pH-sensitive dye that is virtually non-fluorescent at neutral pH and brightly fluorescent in an acidic environment such as the endosome. The fluorescent signal, therefore, can be used as an indicator of cellular internalization of the SOST fusion protein. The multispecific antigen-binding molecules for these experiments were bispecific antibodies with binding specificity for both CD63 (an internalizing effector protein) and the SOST fusion protein (a soluble target molecule), as described in more detail below.

The experiments were conducted as follows: Briefly, HEK293 cells were plated at 10,000 cells/well in poly-D-lysine coated 96 well plates (Greiner Bio-One, Monroe, N.C.). After allowing the cells to settle overnight, the media was replaced with media containing antibody (5 µg/mL, as described below), pHrodo™-myc-tagged-SOST (5 µg/mL), heparin (10 µg/mL), and Hoechst 33342. The cells were then incubated for either 3 hours on ice or 3 hours at 37° C. All cells were washed twice prior to imaging in PBS, and the number of fluorescent spots per cell, as well as the corresponding fluorescence intensity, was counted to establish the extent of pHrodo-myc-tagged-SOST cellular internalization in the presence of the various antibody constructs.

The antibodies used in this Example were as follows: (1) anti-CD63 monospecific antibody (clone H5C6, Developmental Studies Hybridoma Bank, University of Iowa Department of Biology, Iowa City, Iowa); (2) anti-myc antibody (clone 9E10, Schiweck et al., 1997, FEBS Lett. 414(1):33-38); (3) anti-SOST antibody (an antibody having the heavy and light chain variable regions of the antibody designated "Ab-B" in U.S. Pat. No. 7,592,429); (4) anti-CD63 x anti-myc bispecific antibody (i.e., a multispecific antigen-binding molecule comprising an anti-CD63 arm derived from the antibody H5C6 and an anti-myc arm derived from 9E10); (5) anti-CD63 x anti-SOST bispecific antibody #1 (i.e., a multispecific antigen-binding molecule comprising an anti-CD63 arm derived from the antibody H5C6 and an anti-SOST arm derived from "Ab-B"); and (6) anti-CD63 x anti-SOST bispecific antibody #2 (i.e., a multispecific antigen-binding molecule comprising an anti-CD63 arm derived from the antibody H5C6 and an anti-SOST arm derived from the antibody designated "Ab-20" in U.S. Pat. No. 7,592,429). The bispecific antibodies used in these experiments were assembled using the so-called "knobs-into-holes" methodology (see, e.g., Ridgway et al., 1996, Protein Eng. 9(7):617-621).

Figure 8:
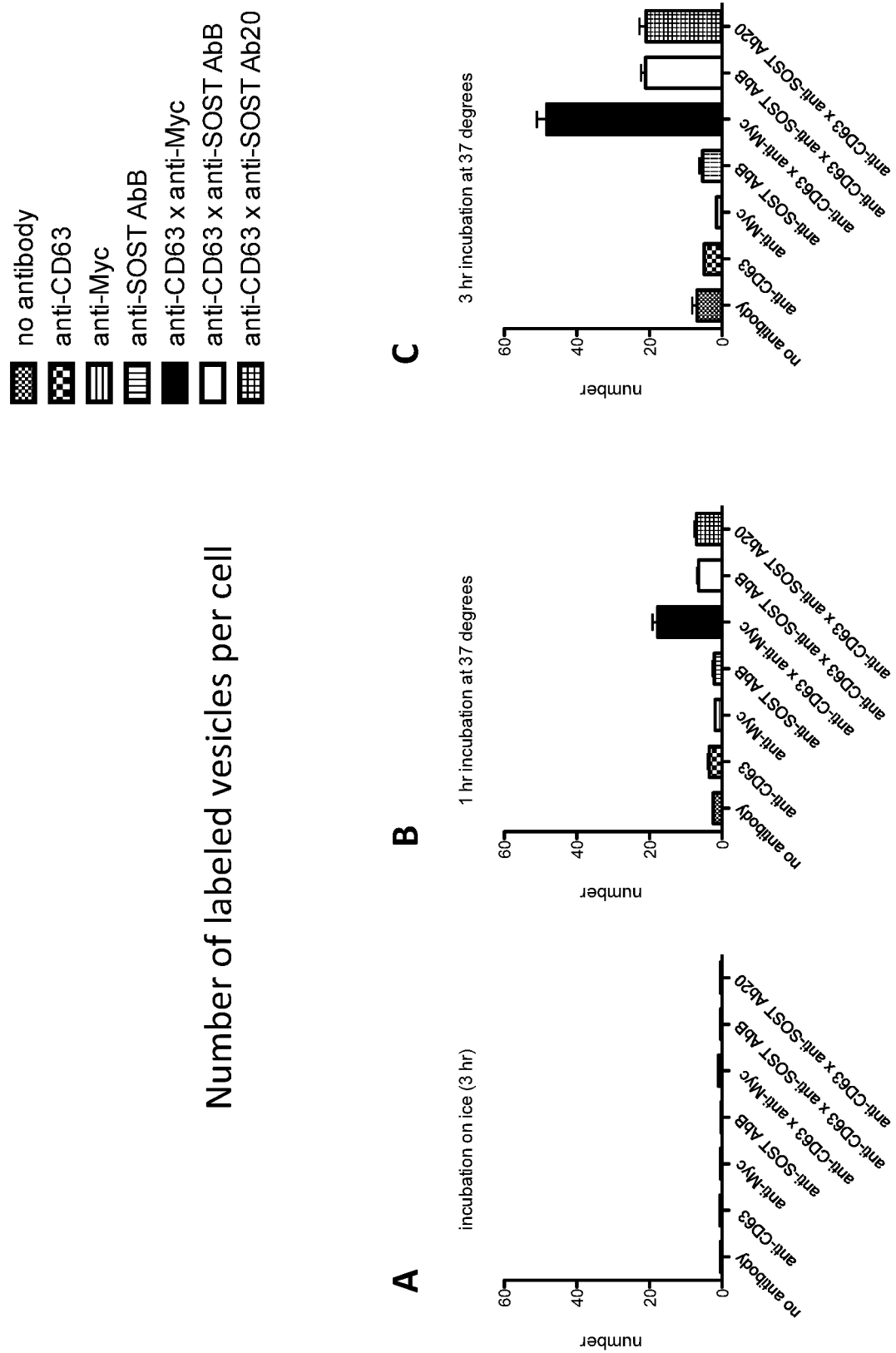
FIG. 8 shows the results of experiments in which HEK293 cells were treated with a SOST construct labeled with a myc tag and a pH-sensitive label (that produces a fluorescent signal at low pH), along with the various mono-specific and bispecific antibodies as shown. Results are expressed in terms of number of fluorescent spots (i.e., labeled vesicles) per cell. Panel A shows the results following incubation on ice for 3 hours, panel B shows the results following 1 hour incubation at 37° C., and panel C shows the results following 3 hours incubation at 37° C.

Results of the internalization experiments are shown in FIG. 8. FIG. 8 shows the number of spots (labeled vesicles) per cell, under the various treatment conditions tested. Taken together, the results of these experiments demonstrate that the bispecific constructs, which simultaneously bind CD63 and SOST (either directly or via the myc tag), caused the greatest amount of SOST internalization as reflected by the fluorescence intensity and number of fluorescent spots per cell over time at 37° C. Thus, the multispecific antigen-binding molecules used in this Example are able to effectively direct the internalization of a soluble target molecule.

Example 5. Changes in Bone Mineral Density in Mice Treated with A Multispecific Antigen-Binding Molecule that Binds CD63 and SOST An anti-CD63 x anti-SOST multispecific antigen-binding molecule, as described in Example 4, is next tested for its ability to increase bone mineral density in mice. Five groups of mice (about 6 mice per group) are used in these experiments. The treatment groups are as follows: (I) untreated negative control mice; (II) mice treated with a blocking anti-SOST monospecific antibody that is known to increase bone mineral density on its own (positive control); (III) mice treated with a bispecific antibody that specifically binds CD63 and SOST but does not inhibit SOST activity on its own or only slightly inhibits SOST activity on its own; (IV) mice treated with an anti-CD63 parental antibody (i.e., a monospecific antibody containing the same anti-CD63 antigen-binding domain as in the bispecific antibody); and (V) mice treated with an anti-SOST parental antibody (i.e., a monospecific antibody containing the same anti-SOST antigen-binding domain as in the bispecific antibody). The amount of antibody administered to the mice in each group is about 10 to 25 mg/kg.

It is expected that mice in group III (treated with an anti-SOST x anti-CD63 bispecific antibody) will exhibit an increase in bone mineral density that is at least comparable to that which is observed in the mice of group II (treated with a known blocking anti-SOST antibody), even though the anti-SOST component of the bispecific antibody does not inhibit SOST activity on its own (as confirmed by the mice in Group V which are expected to not exhibit an increase in bone mineral density). The increase in bone mineral density that is expected in the mice of group III is believed to be driven by CD63-mediated internalization of SOST, as observed in the cellular experiments of Example 4, above.

Example 6. Cellular Internalization of Lipopolysaccharide (LPS) Mediated by a Multispecific Antigen-Binding Molecule That Simultaneously Binds LPS and CD63

This Example illustrates the use of a multispecific antigen-binding molecule of the invention to direct the internalization of a non-protein target molecule, namely lipopolysaccharide (LPS). LPS is a component of the outer membrane of Gram-negative bacteria and is known to contribute to septic shock. Anti-LPS antibodies have been investigated as possible treatment agents for sepsis. The experiments of the present Example were designed to assess the ability of a multispecific antigen-binding molecule to promote the internalization of LPS.

The multispecific antigen-binding molecule used in this Example was a bispecific antibody with one arm directed to LPS (target) and the other arm directed to CD63 (internalizing effector protein). The anti-LPS arm was derived from the antibody known as WN1 222-5. (DiPadova et al., 1993, *Infection and Immunity* 61(9):3863-3872; Muller-Loennies et al., 2003, *J. Biol. Chem.* 278(28):25618-25627; Gomery et al., 2012, *Proc. Natl. Acad. Sci USA* 109(51):20877-20882; U.S. Pat. No. 5,858,728). The anti-CD63 arm was derived from the H5C6 antibody (see Example 4). The anti-LPS x anti-CD63 bispecific antibody (i.e., multispecific antigen-binding molecule) was assembled using the so-called "knobs-into-holes" methodology (see, e.g., Ridgway et al., 1996, Protein Eng. 9(7):617-621).

Two LPS species were used in these experiments: *E. coli* LPS and *Salmonella minnesota* LPS. Both versions were obtained as fluorescent-labeled molecules (ALEXA-FLUOR®-488-labeled LPS, Life Technologies, Carlsbad, Calif.).

Experiments were conducted as follows: HEK293 cells were plated in 96-well PDL-coated imaging plates. After overnight rest, media was replaced with fresh medium. Fluorescently labeled LPS (either *E. coli-* or *S. minnesota-*derived) was added in regular medium. Next, the anti-LPS x anti-CD63 bispecific antibody, or control half-antibodies paired with dummy Fc, were added to the samples. Following various incubation times at 37° C. (1 hour and 3 hours) or on ice (3 hours), cells from the LPS-treated samples were processed as follows: washed—quenched with anti-ALEXA-FLUOR®-488 antibody—washed & fixed. The anti-ALEXA-FLUOR®-488 antibody quenches fluorescence from non-internalized (i.e., surface bound) fluorophore. Thus, any fluorescence observed in the quenching antibody-treated samples is due to internalized LPS. The level of fluorescence from each sample at the various time points was measured.

Figure 9:
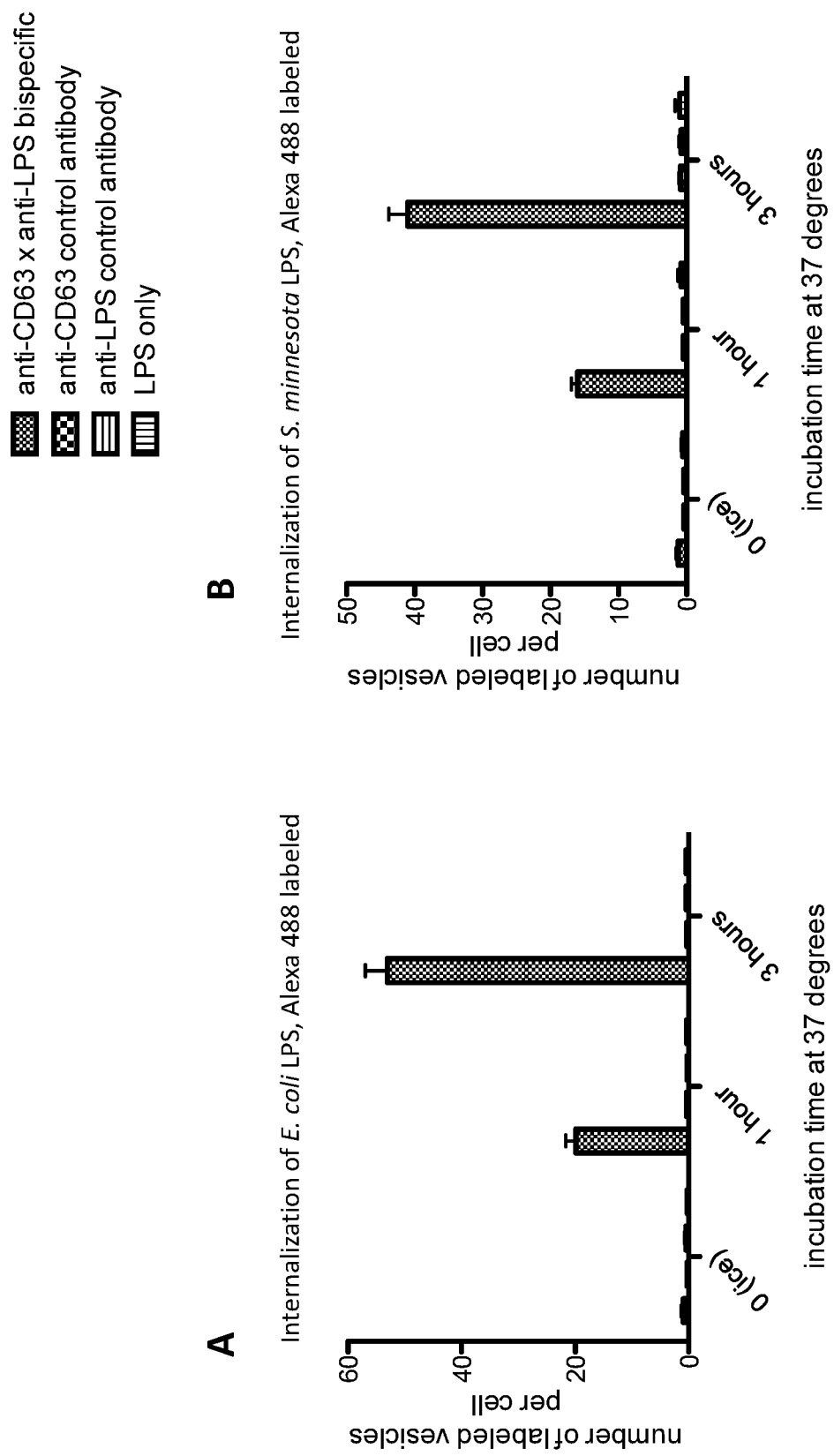
FIG. 9 shows the results of experiments in which HEK293 cells were treated with fluorescently-labeled lipopolysaccharide (LPS) from E. coli (Panel A) or S. minnesota (Panel B), along with an anti-CD63 x anti-LPS bispecific antibody, control antibodies, or LPS only, for various times, followed by quenching of non-internalized (i.e., surface bound) fluorophore. Fluorescent signal therefore reflects internalized LPS under the various conditions shown. Results are expressed in terms of number of fluorescent spots (i.e., labeled vesicles) per cell.

FIG. 9 expresses the results of these experiments in terms of the number of labeled vesicles per cell. As shown in FIG. 9, only cells treated with the anti-CD63 x anti-LPS bispecific antibody demonstrated significant numbers of labeled vesicles that increased over time. Cells treated with labeled LPS and the control antibodies did not exhibit appreciable numbers of fluorescent vesicles, indicating that LPS was not internalized under those treatment conditions.

This Example therefore demonstrates that an anti-LPS x anti-CD63 bispecific antibody causes internalization of LPS into cells in a manner that requires simultaneous binding of LPS and CD63. Accordingly, these results support the use of multispecific antigen-binding molecules of the invention to promote cellular internalization of target molecules such as LPS for the treatment of diseases and disorders such as sepsis.

Example 7. Cellular Internalization and Degradation of Her2 Mediated by a Multispecific Antigen-Binding Molecule That Simultaneously Binds Her2 and PRLR This Example includes three separate experiments which illustrate the use of a multispecific antigen-binding molecule of the invention to direct the internalization and degradation of a tumor-associated antigen (Her2). The elimination of Her2 from the surface of tumor cells would be a desirable approach for the treatment of certain types of cancers characterized by high Her2 expression (e.g., breast cancer, gastric cancer, gastro-esophageal cancers, etc.).

The multispecific antigen-binding molecules used in the experiments of this Example were bispecific antibodies with one arm directed to Her2 (target) and the other arm directed to PRLR (internalizing effector protein).

Experiment 1

As an initial experiment, the ability of an anti-Her2 x anti-PRLR bispecific antibody (referred to herein as "Her2xPRLR bsAb1") to degrade endogenous Her2 in T47D breast cancer cells was evaluated. T47D breast cancer cells express low levels of HER2 and are generally recalcitrant to anti-HER2 therapy (see Horwitz et al., "Variant T47D human breast cancer cells with high progesterone-receptor levels despite estrogen and antiestrogen resistance," Cell. 1982 March; 28(3):633-42).

The anti-Her2 arm was derived from the antibody known as trastuzumab. The anti-PRLR arm was derived from a fully human anti-PRLR antibody. The anti-Her2 x anti-PRLR bispecific antibody (i.e., multispecific antigen-binding molecule) was assembled using the so-called "knobs-into-holes" methodology (see, e.g., Ridgway et al., 1996, Protein Eng. 9(7):617-621). Other constructs used in this Experiment were trastuzumab (mono-specific antibody), anti-PRLR Ab (mono-specific antibody, referred to as H1H6958N2, as set forth in US Patent Application Publication No. 2015/0056221, the disclosure of which is incorporated by reference herein in its entirety), and a mono-specific Control antibody (directed against an irrelevant non-human antigen).

For this experiment, T47D cells expressing endogenous levels of Her2 and PRLR receptors were grown in RPMI (Irvine Scientific, 9160) supplemented with 10% FBS (ATCC, 30-2020), 10 mM Hepes, 1 mM Sodium Pyruvate, and 10 µg/ml Insulin. Cycloheximide (CHX) at 50 ug/ml was used to stop protein synthesis. T47D cells were treated with either Cycloheximide and Trastuzumab (CHX/Trastuzumab), Cycloheximide and Her2xPRLR bsAb1 (CHX/bsAb1), Cycloheximide and PRLR Ab (CHX/PRLR Ab), Cycloheximide and Control Ab (CHX/Control Ab), or with Cycloheximide, PRLR Ab and Trastuzumab for either 0, 1, 2, or 4 hours.

Cells were lysed on ice in RIPA buffer (100 mM Tris-HCl, 300 mM NaCl, 2% NP-40, 1% Sodium deoxycholate, and 0.2% SDS) (Boston BioProducts BP-116X) supplemented with protease and phosphatase inhibitors (Thermo Fisher, 1861280), followed by sonication (Qsonica Model Q55, three pulses). The sonicated lysates were diluted with 2×SDS Sample Buffer 1:1, heated at 95° C. for 10 min, followed by centrifugation at 13,000 rpm for 10 min at room temperature. Supernatants were resolved on 4-20% Novex Tris-Glycine gels and blotted to PVDF membranes.

Her2 antibodies (Dako, A0485) at 1:300 or PRLR antibodies (Life Technologies, 35-9200) at 1:250 were used for primary labeling of membranes followed by HRP-conjugated secondary antibody at 1:5000, and chemiluminescence detection with ECL (Amersham, RPN2106). Quantitation of the Western blots was performed by calculating net intensity of bands with CareStream software (Kodak). Results are shown in Table 1. Values are expressed in terms of relative units compared to background.

As shown in Table 1, upon inhibition of protein synthesis with Cycloheximide, PRLR was shown to undergo rapid and complete degradation with all treatments used; the process was not affected by any of the antibodies tested. By contrast, in the presence of Cycloheximide, Her2 was degraded in cells treated with Her2xPRLR bsAb1, but not with the mixture of Trastuzumab and anti-PRLR Ab, individual PRLR Abs, Trastuzumab, or Control Antibodies. This result suggests that Her2xPRLR bsAb1 serves to bridge Her2 to PRLR on the cell surface which is followed by degradation of the Her2-bsAb1-PRLR complex.

TABLE 1

| Treatment | Time (hr) | Her2 | PRLR |
|---|---|---|---|
| Cycloheximide + | 0 | 5.87 | 6.67 |
| Trastuzumab | 1 | 2.51 | 4.28 |
|  | 2 | 5.38 | 2.89 |
|  | 4 | 5.66 | 0.18 |
| Cycloheximide + | 0 | 3.99 | 6.48 |
| Her2 × PRLR bsAb1 | 1 | 5.79 | 3.68 |
|  | 2 | 2.36 | 1.62 |
|  | 4 | 0.70 | 0.04 |
| Cycloheximide + | 0 | 5.36 | 5.75 |
| anti-PRLR Ab | 1 | 4.48 | 1.24 |
|  | 2 | 4.24 | 0.69 |
|  | 4 | 6.32 | 0 |
| Cycloheximide + | 0 | 3.36 | 4.66 |
| Control Antibody | 1 | 3.09 | 3.10 |
|  | 2 | 4.98 | 3.30 |
|  | 4 | 4.74 | 0.23 |
| Cycloheximide + | 0 | 5.37 | 6.12 |
| Trastuzumab + | 1 | 4.22 | 2.16 |
| anti-PRLR Ab | 2 | 4.48 | 0.44 |
|  | 4 | 5.22 | 0 |

Experiment 2

In a second experiment, the dose-dependent effects of Her2 × PRLR multispecific antigen-binding proteins on Her2 degradation in vitro, as well as the potential effects on PRLR levels, were investigated. Two different Her2 × PRLR bispecific antibodies ("Her2xPRLR bsAb1" and "Her2xPRLR bsAb2") were used in this experiment. Both bispecific antibodies were constructed using the knobs-into-holes methodology. The anti-Her2 arm was identical for both bispecific antibodies and was derived from the antibody known as trastuzumab. The anti-PRLR arms of Her2xPRLR bsAb1 and Her2xPRLR bsAb2 were derived from two different fully human anti-PRLR antibodies.

For this experiment, T47D cells expressing endogenous levels of Her2 and PRLR receptors were grown in RPMI (Irvine Scientific, 9160) supplemented with 10% FBS (ATCC, 30-2020), 10 mM Hepes, 1 mM Sodium Pyruvate and 10 ug/ml Insulin. T47D cells were treated for 6 hours with either bsAb1 or bsAb2 at 10 ug/ml, 3 ug/ml, 1 µg/ml, 0.3 µg/ml, 0.03 µg/ml, or 0 µg/ml.

Cells were lysed on ice in RIPA buffer (100 mM Tris-HCl, 300 mM NaCl, 2% NP-40, 1% Sodium deoxycholate, and 0.2% SDS) (Boston BioProducts BP-116X) supplemented with protease and phosphatase inhibitors (Thermo Fisher, 1861280), followed by sonication (Qsonica Model Q55, three pulses). The sonicated lysates were diluted with 2×SDS Sample Buffer 1:1, heated at 95° C. for 10 min, followed by centrifugation at 13,000 rpm for 10 min at room temperature. Supernatants were resolved on 4-20% Novex Tris-Glycine gels and blotted to PVDF membranes.

Her2 antibodies (Dako, A0485) at 1:300, PRLR antibodies (Life Technologies, 35-9200) at 1:250, or beta-Actin antibodies (Genetex, GTX100313) at 1:10,000 were used for primary labeling of membranes followed by HRP-conjugated secondary antibody at 1:5000, and chemiluminescence detection with ECL (Amersham, RPN2106).

Quantitation of the Western blots was performed by calculating net intensity of bands with CareStream software (Kodak). To control for loading, normalization to actin was used as follows: the sample with highest actin net intensity was used as normalization control. Actin net intensity of each sample was divided by normalization control value to get a relative value of the sample. Net intensities of each target protein (Her2 or PRLR) were divided by the calculated relative actin value for the sample to get a normalized Her2 or PRLR value (arbitrary units). Results are shown in Table 2.

As shown in Table 2, both Her2xPRLR bsAb1 and Her2xPRLR bsAb2 induced Her2 degradation in a dose dependent manner in T47D cells. In contrast, the levels of PRLR were not affected by bispecific antibody treatment. This result is consistent with PRLR undergoing constitutive surface turnover on the surface of these cells.

TABLE 2

| Treatment | Concentration (µg/ml) | Her2 | PRLR |
|---|---|---|---|
| Her2 × PRLR bsAb1 | 0 | 6.47 | 2.49 |
|  | 0.03 | 3.44 | 0.95 |
|  | 0.1 | 1.46 | 1.10 |
|  | 0.3 | 1.47 | 1.33 |
|  | 1.0 | 1.10 | 1.63 |
|  | 3.0 | 1.27 | 1.64 |
|  | 10.0 | 0.98 | 1.30 |
| Her2 × PRLR bsAb2 | 0 | 6.16 | 3.48 |
|  | 0.03 | 4.37 | 2.71 |
|  | 0.1 | 3.12 | 3.64 |
|  | 0.3 | 2.43 | 3.42 |
|  | 1.0 | 1.43 | 2.85 |
|  | 3.0 | 1.55 | 2.52 |
|  | 10.0 | 1.59 | 2.70 |

Experiment 3

The foregoing experiments suggest that Her2 degradation by a Her2xPRLR bispecific antibody requires that the bispecific antibody simultaneously bind PRLR (an internalizing effector protein) and Her2 (a target protein). To confirm this principle, a third experiment was conducted to assess the effect of blocking either the PRLR- or Her2-binding arms of the Her2xPRLR bsAb1 on Her2 internalizing activity.

For this experiment T47D cells expressing endogenous levels of Her2 and PRLR receptors were grown in RPMI (Irvine Scientific, 9160) supplemented with 10% FBS (ATCC, 30-2020), 10 mM Hepes, 1 mM Sodium Pyruvate and 10 µg/ml Insulin. Her2xPRLR bsAb1 (10 µg/ml) was left untreated (i.e., both arms unblocked), or incubated with either a soluble PRLR protein construct ("PRLR.mmh" to block the PRLR-binding arm) or a soluble Her2 protein construct ("Her2.mmh" to block the Her2-binding arm) at 37° C. for 1 h (1:2 molar ratio) before adding to T47D cells for either 0, 2, 4, or 6 hours.

At the end of the incubation period, cells were lysed on ice in RIPA buffer (100 mM Tris-HCl, 300 mM NaCl, 2% NP-40, 1% Sodium deoxycholate, and 0.2% SDS) (Boston BioProducts BP-116X) supplemented with protease and phosphatase inhibitors (Thermo Fisher, 1861280), followed by sonication (Qsonica Model Q55, three pulse). The sonicated lysates were diluted with 2×SDS Sample Buffer 1:1, and heated at 95C for 10min, followed by centrifugation at 13,000 rpm for 10 min at room temperature. Supernatants were resolved on 4-20% Novex Tris-Glycine gels and blotted to PVDF membranes.

Her2 antibodies (Dako, A0485) at 1:300 or beta-Actin antibodies (Genetex, GTX100313) at 1:10,000 were used for primary labeling of membranes followed by HRP-conjugated secondary antibody at 1:5000, and chemiluminescence detection with ECL (Amersham, RPN2106).

Quantitation of the Western blots was performed by calculating net intensity of bands with CareStream software (Kodak). To control for loading, normalization to actin was used as follows: the sample with highest actin net intensity was used as normalization control. Actin net intensity of each sample was divided by normalization control value to get a relative value of the sample. Net intensity of Her2 band was divided by the calculated relative actin value for the sample to get a normalized Her2 value (arbitrary units). Results are shown in Table 3.

As shown in Table 3, Her2xPRLR bsAb1-mediated Her2 degradation was completely prevented in T47D cells by blocking either Her2 or PRLR arms of Her2xPRLR bsAb1, indicating that Her2 degradation occurred via its physical connection to PRLR which was mediated by simultaneous Her2 and PRLR binding by the Her2xPRLR bsAb1 multi-specific antigen binding protein.

Example 8. Increased Potency of Trastuzumab Emtansine Mediated by a Multispecific Antigen-Binding Molecule That Simultaneously Binds Her2 and PRLR This Example illustrates the use of multispecific antigen-binding molecules of the invention to increase the potency of an antibody-drug conjugate ("ADC"). More specifically, this Example demonstrates the use of a multispecific antigen-binding molecule comprising a first binding domain directed to an internalizing effector protein and a second binding domain directed to a tumor-associated target antigen, in combination with a second antigen-binding molecule specific for the tumor-associated antigen target (also referred to herein as an "accomplice molecule"), wherein the accomplice molecule is an ADC. In the experiments set forth herein below, the internalizing effector protein is prolactin receptor (PRLR), the tumor-associated antigen target is Her2, and the accomplice molecule is an ADC specific for Her2 (i.e., trastuzumab emtansine (T-DM1)).

Trastuzumab is a recombinant humanized monoclonal antibody that binds to the extracellular domain of Her2. Trastuzumab and its corresponding ADC, Trastuzumab-emtansine, or T-DM1, have been successfully used in patients with strong Her2 overexpression, as assessed by immunohistochemistry (IHC 3+). However, there is currently no effective therapy available for patients with Her2 IHC2+ and Her2 IHC1+ tumors.

TABLE 3

| Treatment | Time (hr) | Her2 |
|---|---|---|
| Her2 × PRLR bsAb1 | 0 | 2.84 |
| | 2 | 2.39 |
| | 4 | 1.31 |
| | 6 | 0.42 |
| Her2 × PRLR bsAb1 + PRLR · mmh | 0 | 3.06 |
| | 2 | 1.94 |
| | 4 | 2.65 |
| | 6 | 2.30 |

TABLE 3-continued

| Treatment | Time (hr) | Her2 |
|---|---|---|
| Her2 × PRLR bsAb1 + Her2 · mmh | 0 | 2.16 |
| | 2 | 2.30 |
| | 4 | 2.56 |
| | 6 | 1.47 |

In this Example, the ability of four different anti-Her2 x anti-PRLR bispecific antibodies (referred to herein as "Her2xPRLR bsAb36," "Her2xPRLR bsAb37," "Her2xPRLR bsAb42" and "Her2xPRLR bsAb45") to increase the cell-killing potency of T-DM1 on Her2-expressing cells was evaluated. The bispecific antibodies used in this Example were constructed from four different anti-Her2 arms and two different anti-PRLR arms, as summarized in Table 4.

TABLE 4

| Bispecific Antibody | Anti-Her2 Arm | Anti-PRLR Arm |
|---|---|---|
| Her2 × PRLR bsAb36 | anti-Her2 Ab-1 | anti-PRLR Ab-1 |
| Her2 × PRLR bsAb37 | anti-Her2 Ab-2 | anti-PRLR Ab-1 |
| Her2 × PRLR bsAb42 | anti-Her2 Ab-3 | anti-PRLR Ab-2 |
| Her2 × PRLR bsAb45 | anti-Her2 Ab-4 | anti-PRLR Ab-2 |

Standard methods were used to construct the anti-Her2 x anti-PRLR bispecific antibodies (i.e., multispecific antigen-binding molecules). Control experiments were also conducted using a control ADC (i.e., an antibody-drug conjugate comprising an antibody directed against an irrelevant non-human protein conjugated to DM1), or an anti-PRLR-DM1 ADC (the antibody-drug conjugate referred to as H1H6958N2 in US 2015/0056221, the disclosure of which is incorporated by reference herein in its entirety).

To evaluate the ability of Her2xPRLR bispecific antibodies to enhance the cell killing effect of T-DM1, T47D cells expressing endogenous levels of PRLR and overexpressing Her2 to intermediate levels (T47D/Her2) were first grown in RPMI (Irvine Scientific, 9160) supplemented with 10% FBS (ATCC, 30-2020), 10 mM Hepes, 1 mM Sodium Pyruvate and 10 ug/ml Insulin. Cells were then seeded on 96-well plates at 3000 cells/well. The next day cells were left untreated, or treated with a range of concentrations of either T-DM1, or Control ADC, or anti-PRLR-DM1, or a combination of T-DM1 with 10 ug/ml of either Her2xPRLR bsAb42, Her2xPRLR bsAb36, Her2xPRLR bsAb37, or Her2xPRLR bsAb45 for 3 days in triplicates.

Cell viability was assessed as follows: 3 days post-treatment cells were fixed with 0.25% PFA, 0.1% Saponin, 2 ug/ml Hoechst for 20 min, whole well images were acquired on automatic microscope ImageXpress$^{MICRO}$ at 10× and analyzed using Cell Proliferation$^{HT}$ MetzxPress™ Module (nuclear count). Results are summarized in Table 5.

TABLE 5

| Treatment | IC50 (nM) |
|---|---|
| T-DM1 | 30.0 |
| Control ADC | 200.0 |
| T-DM1 + Her2 × PRLR bsAB42 | 2.0 |
| Control ADC + Her2 × PRLR bsAB42 | 100.0 |
| Anti-PRLR-ADC | 0.9 |
| T-DM1 + Her2 × PRLR bsAB37 | 2.0 |
| T-DM1 + Her2 × PRLR bsAB36 | 2.5 |
| T-DM1 + Her2 × PRLR bsAB45 | 1.0 |

As shown in Table 5, the cell killing potency of T-DM1 was significantly enhanced by the presence of the Her2xPRLR bispecific antibodies of the present invention. Thus, this Example demonstrates the ability of the multispecific antigen binding proteins of the invention to enhance the potency and efficacy of immunoconjugate molecules directed to target proteins that are not normally internalized by cells in a rapid manner.

T-DM1 is known to be active against tumors expressing high levels of HER2, while those cells expressing low and intermediate levels of HER2 remain resistant to T-DM1 treatment. In contrast, an anti-PRLR-ADC is capable of inducing robust killing of breast tumor cells expressing low levels of PRLR. The difference in killing efficiency between anti-PRLR-ADC and T-DM1 is likely due to the difference in internalization rates and lysosomal trafficking of their targets respective targets. The intracellular trafficking of PRLR and HER2 were compared.

Figure 11:
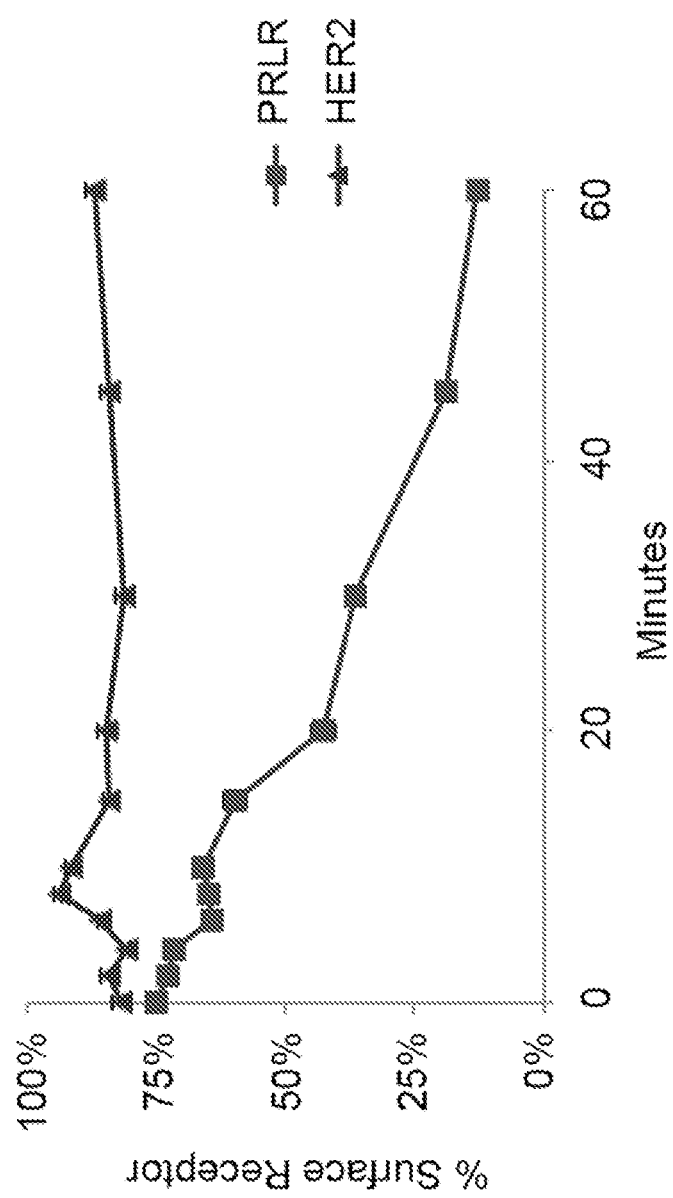
FIG. 11 depicts internalization of prolactin receptor (PRLR) and HER2 on T47D cells by measuring the amount of PRLR or HER2 remaining on the cell surface at 0 to 60 minutes after transferring cells from 4° C. to 37° C. Percent surface receptor remaining over time is shown. Squares represent PRLR and triangles represent HER2.

In those cells expressing low surface levels of PRLR and HER2, the PRLR was observed to undergo rapid constitutive lysosomal trafficking and degradation that was largely independent of prolactin ligand. HER2, however, did not undergo rapid constitutive lysosomal trafficking and degradation. For example, T47D cells, which express low levels of PRLR and HER2, internalized 80% of the PRLR within 60 minutes, whereas HER was not internalized (FIG. 11). In these experiments, T47D cells were incubated on ice with either CF™594 -labeled anti-PRLR primary antibody or CF™594 -labeled anti-HER2 primary antibody. The internalization process was initiated by adding pre-warmed (37° C.) media to the cells. At indicated times cells, the cells were fixed with 4% paraformaldehyde to stop internalization, and stained with secondary Alexa Fluor® 488-conjugated goat anti-Human Fab to detect non-internalized antibodies remaining on the cell surface (yellow). Co-localization was quantified in a pixel-by-pixel basis for all sections of the confocal stack. The results are depicted in FIG. 11)

Figure 12:
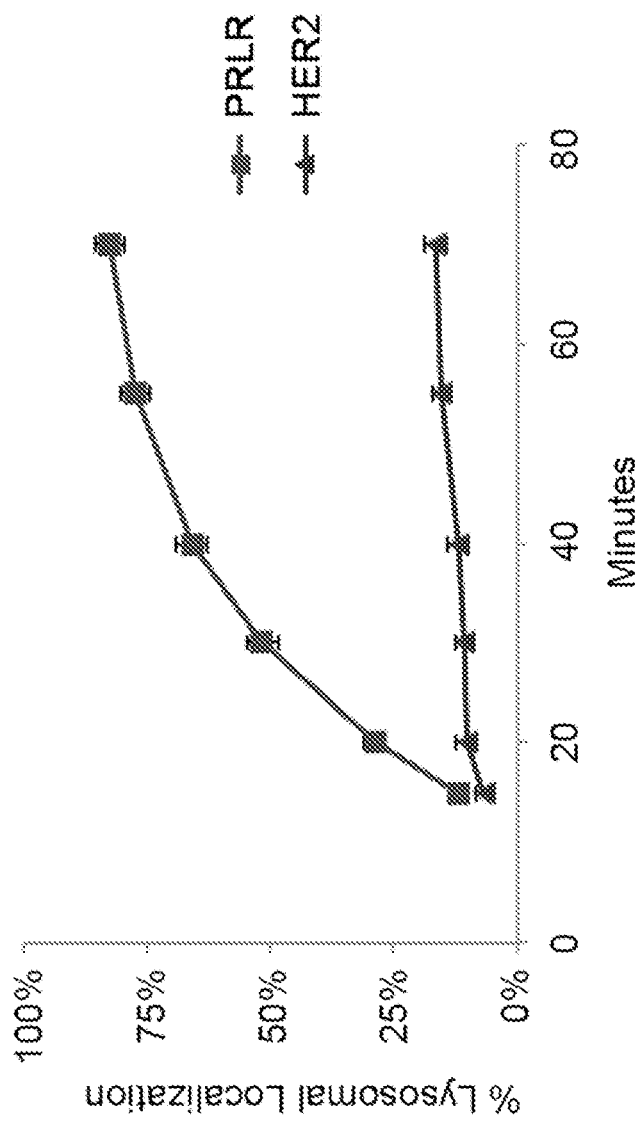
FIG. 12 depicts co-localization of prolactin receptor (PRLR) and HER2 with lysosomes in T47D cells. Percent receptor associated with lysosomes over time is shown. Squares represent PRLR and triangles represent HER2.

Likewise, PRLR, but not HER2 was observed to be rapidly internalized into the lysosomal compartment of T47D cells. CF™594-labeled anti-PRLR antibodies or CF™594-labeled anti-HER2 antibodies were added to T47D cells pre-labeled with fluorescein-3 kDa dextrans. The antibody-receptor complexes were allowed to internalize at 37° C. for indicated times (X-axis of FIG. 12), then fixed with 4% paraformaldehyde. Co-localization of internalized antibodies with dextrans-labeled lysosomes was determined. The results are depicted in FIG. 12 and essentially agree with the internalization data of FIG. 11.

Figure 13:
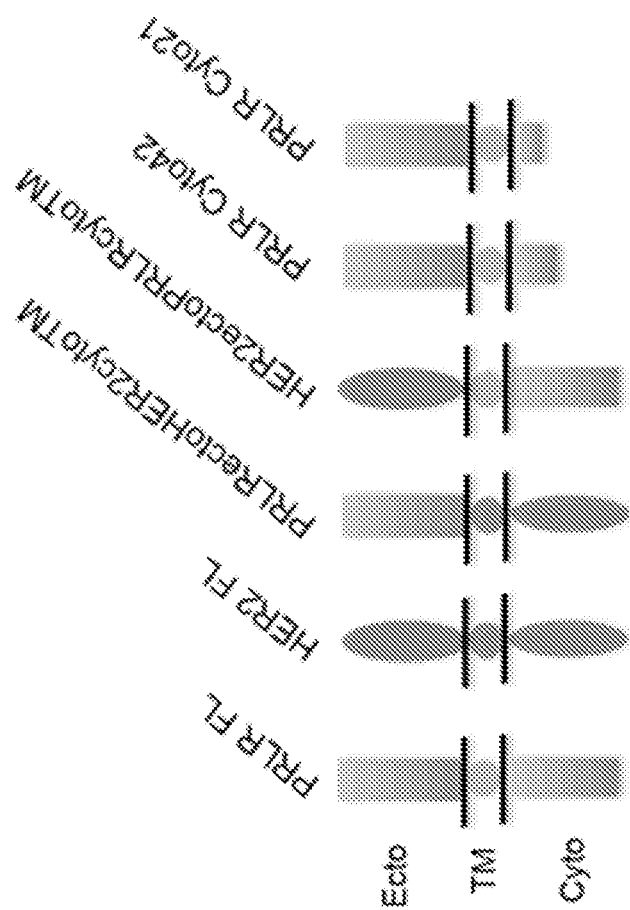
FIG. 13 depicts schematically the PRLR and HER2 truncations and chimeras.

The sequence motifs governing the constitutive turnover of PRLR were mapped to a 21 amino acid region in receptor cytoplasmic domain; PRLR turnover enabled efficient ADC-mediated cell cycle arrest and cell killing. FIG. 13 depicts the various PRLR and HER2 constructs used in the following experiments, including: (1) full length PRLR (PRLR FL), (2) full length HER2 (HER2 FL), (3) the extracellular (Ecto) domain of PRLR fused to the transmembrane (TM) and cytoplasmic (Cyto) portions of HER2 (PRLRectoHER2cytoTM), (4) the extracellular (Ecto) domain of HER2 fused to the transmembrane (TM) and cytoplasmic (Cyto) portions of PRLR (HER2ectoPRLRcytoTM), (5) PRLR with amino acids 301-622 (as measured by unprocessed protein with signal peptide remaining) deleted (PRLR Cyto42), and (6) PRLR with amino acids 280-622 (as measured by unprocessed protein with signal peptide remaining) deleted (PRLR Cyto21).

Figure 14:
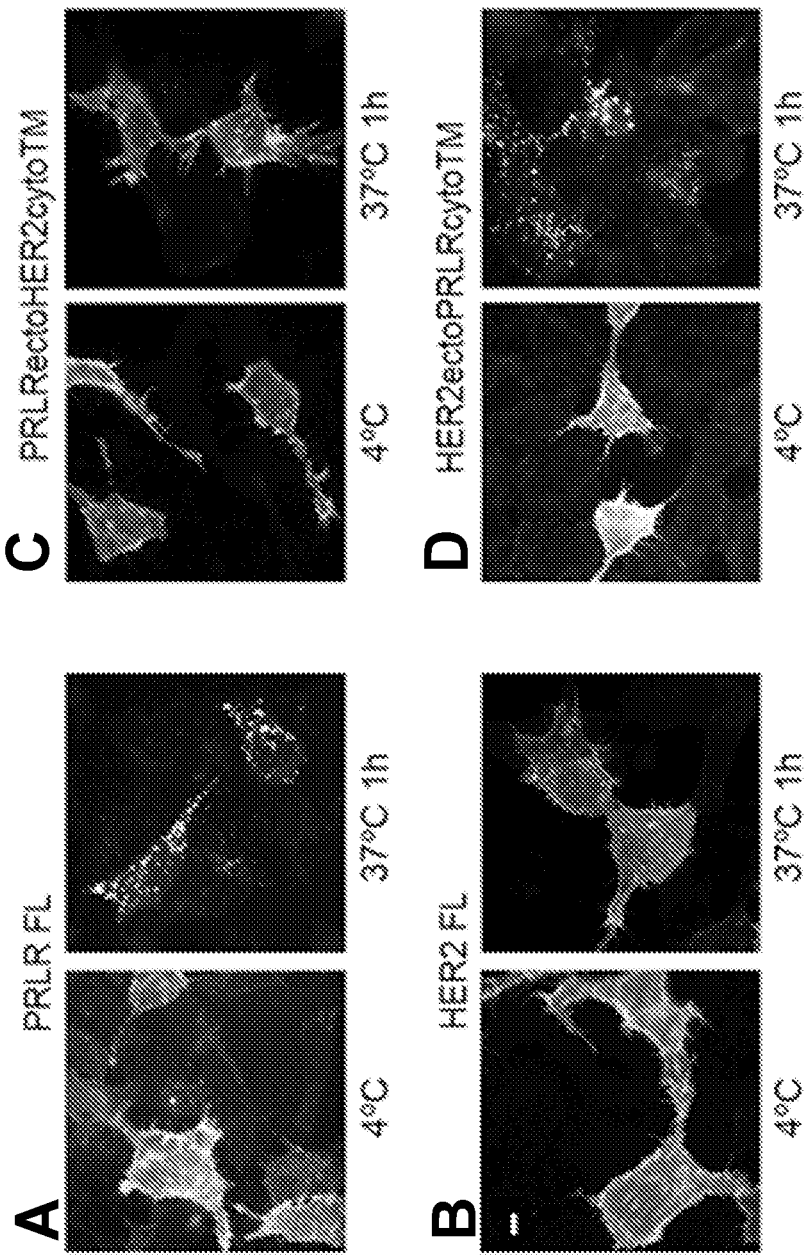
FIG. 14 depicts fluorescent micrographs of HEK293 cells expressing various PRLR and HER2 constructs and chimeras. The subpanels to the left in each panel depict cells at 4° C. before internalization. The subpanels to the right in each panel depict cells after one hour at 37° C. Panel A depicts cells expressing full-length PRLR (PRLR FL). Panel B depicts cells expressing full-length HER2 (PRLR FL). Panel C depicts cells expressing the PRLRectoHER2cytoTM construct. Panel D depicts cells expressing the HER2ectoPRLRcytoTM construct.

To map the internalization effector sequences of PRLR to one of its domains (extracellular, transmembrane, cytoplasmic) HEK293 cells were grown in 24-well optical plates and transiently transfected with a mammalian expression vector encoding PRLR, HER2, HER2ectoPRLRcytoTM, or PRLRectoHER2cytoTM for 24 hours. The transfected cells were then incubated on ice in the presence of CF™594 -labeled primary antibody, and then warmed to 37° C. and incubated for an additional hour. FIG. 14 depicts decorated cells at 4° C., when construct is not expected to be internalized), and after 37° C., when those constructs capable of being rapidly internalized would be internalized. Panel A depicts internalized PRLR FL construct at 37° C. Panel B depicts the HER2 FL construct, which essentially failed to internalize within one hour at 37° C. Panel C depicts the PRLRecto-HER2cyto/TM construct, which also essentially failed to internalize within one hour at 37° C. Panel D depicts the internalized HER2ectoPRLRcyto/TM construct at 37° C. These results suggest that the cytoplasmic domain of PRLR provides the internalization effector sequence.

Figure 15:
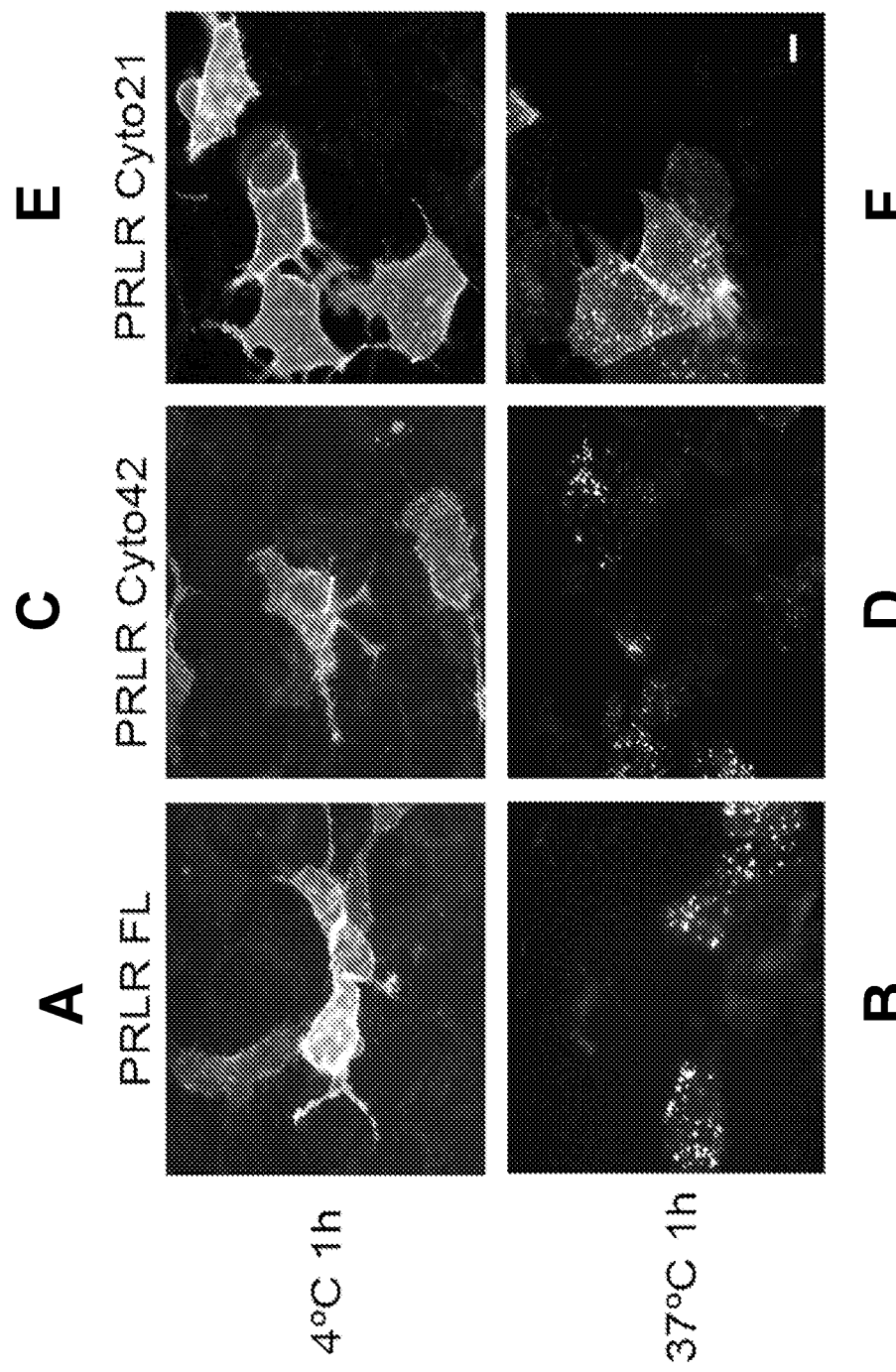
FIG. 15 depicts fluorescent micrographs of HEK293 cells expressing various PRLR constructs and truncations. Panel A depicts cells expressing full length PRLR, stained for PRLR, after 1 hour at 4° C. Panel B depicts cells expressing full length PRLR, stained for PRLR, after I hour at 37° C. Panel C depicts cells expressing truncated PRLR with 42 residues of the cytoplasmic domain, stained for PRLR, after 1 hour at 4° C. Panel D depicts cells expressing truncated PRLR with 42 residues of the cytoplasmic domain, stained for PRLR, after I hour at 37° C. Panel E depicts cells expressing truncated PRLR with only 21 residues of the cytoplasmic domain, stained for PRLR, after 1 hour at 4° C. Panel F depicts cells expressing truncated PRLR with only 21 residues of the cytoplasmic domain, stained for PRLR, after I hour at 37° C.

The internalization effector sequence was further mapped to the PRLR amino acid residues of about 280 to about 300 (e.g., residues 280 to 300 of SEQ ID NO:11; residues DAHLLEKGKSEELLSALGCQD [SEQ ID NO:12]) (a.k.a. PRLR Cyto21-42). Labeled antibody-Ice-to-37° C. experiments were performed on HEK293 cells as described above. FIG. 15 depicts the cellular uptake of those constructs containing the entire cytoplasmic domain of PRLR (PRLR FL) (panels A and B), the membrane proximal 42 amino acids (PRLR Cyto42) (panels C and D), and the membrane proximal 21 amino acids (PRLR Cyto21) (panels D and E). While the PRLR Cyto42 construct was rapidly internalized, the PRLR Cyto21 construct was not. This demonstrates that the PRLR cytoplasmic domain region between 21 and 42 amino acid proximal to plasma membrane (Cyto21-42) contains information essential for internalization and degradation of PRLR.

Figure 16:
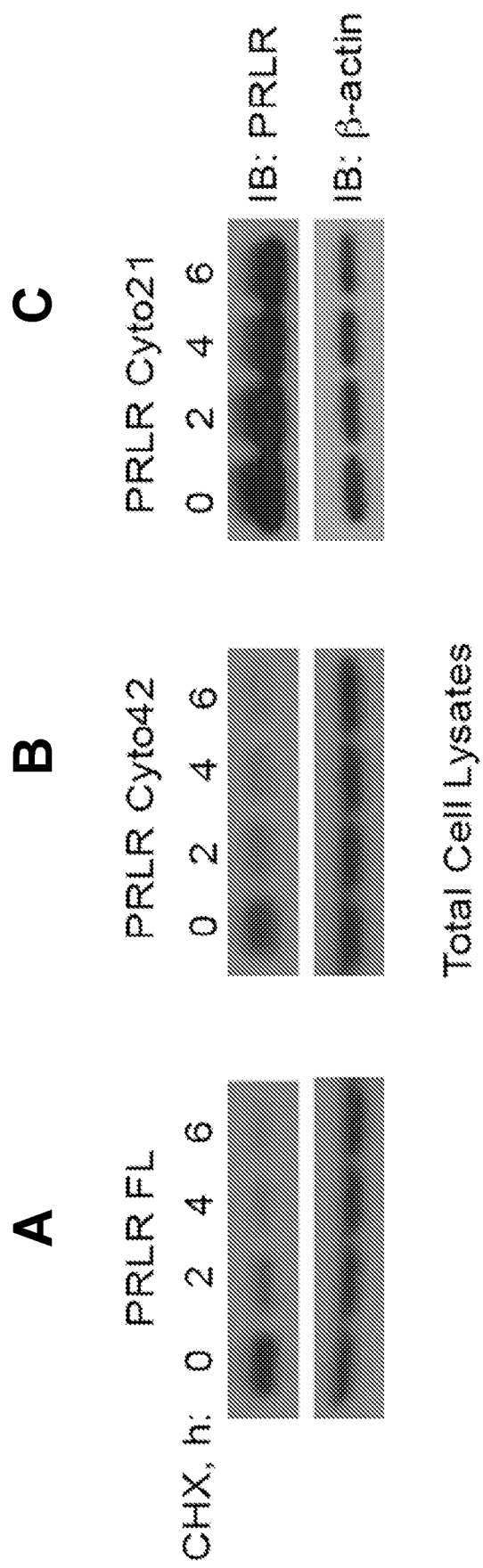
FIG. 16 depicts western blots of cell lysates of cells expressing full length PRLR (panel A), cells expressing truncated PRLR with 42 residues of the cytoplasmic domain remaining (panel B), and cells expressing truncated PRLR with 21 residues of the cytoplasmic domain remaining (panel C). The upper subpanels are stained with anti-PRLR antibody. The lower subpanels are stained for beta-actin to control for loading.

To determine whether internalized PRLR constructs were degraded (i.e., targeted to the lysosome), the transfected HEK293 cells were treated with cycloheximide (CHX) at various times post-warming (0 hours, 2 hours, 4 hours, 6 hours) to arrest protein production. As demonstrated by the western blot of total cell lysates (FIG. 16), PRLR FL and PRLR Cyto42, degraded rapidly, while almost no PRLR Cyto21 degradation was detected.

Figure 17:
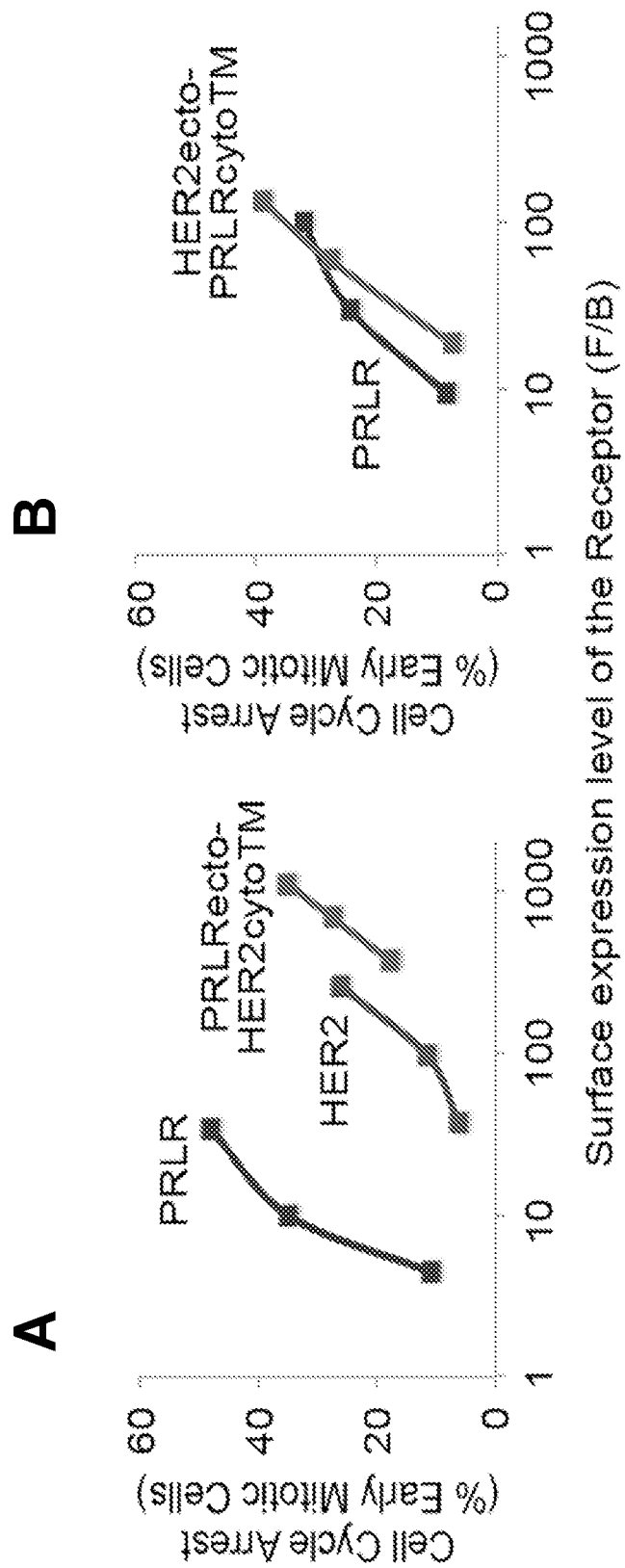
FIG. 17 depicts the percentage of cells in early mitosis versus levels of surface expression of PRLR or HER2 or PRLRectoHER2cytoTM (Panel A), PRLR or HER2ectoPRLRcytoTM (Panel B) after treatment with either PRLR-DM1 or HER2-DM1.

The effectiveness of the PRLR transmembrane and cytoplasmic domain as an internalization effector to deliver an anti-cell proliferation drug as an antibody drug conjugate (ADC) was tested on transfected HEK293 cells. HEK293 cells were engineered to express PRLR, HER2, or PRLRectoHER2cyto/TM in a tetracycline-controlled fashion (e.g., using the Lenti-X™ Tet-On® System, Clontech, Mountain View, Calif.). The transfected cells were induced for 24 hours with 0.01 ηg/ml, or 0.003 μg/ml, or 0.7 μg/ml of doxycycline to achieve different expression levels of the receptors, which were determined by flow cytometry. Either PRLR conjugated with mertansine (a.k.a. DM1, a.k.a. emtansine) (1 ηM) (panel A, FIG. 17) or HER2-DM1 (1 ηM) (panel B, FIG. 17) was added to the respectively transfected cells, which were incubated for another 24 h. Cell cycle analysis was performed using phospho-Histone H3 (Ser10) antibody to detect early mitotic cells. The results are depicted in FIG. 17, which demonstrates that the transmembrane/cytoplasmic domain of PRLR effectively mediates delivery of drug into the cells.

Figure 18:
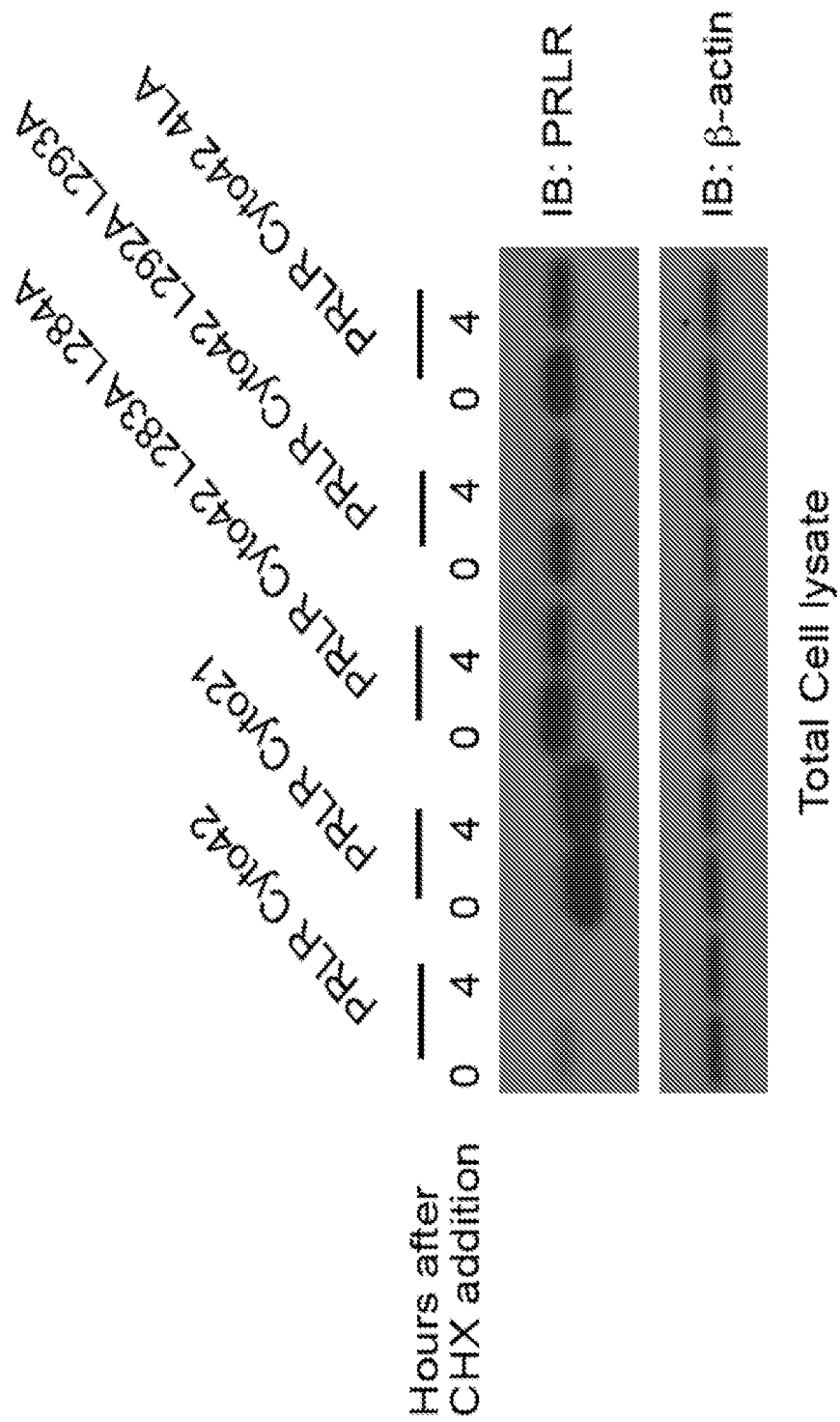
FIG. 18 depicts a western blot of whole cell lysates expressing various PRLR constructs, truncations, and substitutions at 0 hours and 4 hours post CHX treatment. The upper panel is stained for PRLR, and the lower panel is stained for beta-actin to control for loading.

Alanine mutagenesis of the cytoplasmic domain, specifically the Cyto21-24 domain, was performed to help map the residues necessary for internalization. The site directed mutagenesis of two dileucines contained in the Cyto21-42 sequence inhibited the turnover of PRLR Cyto42 on transfected HEK293 cells. T-REx™ HEK293 cells (i.e., stable Tet-On expressing cells, ThermoFisher Scientific, Waltham Mass.) were engineered to express PRLR Cyto42, PRLR Cyto21, PRLR Cyto42 L283A L284A, PRLR Cyto42 L292A L293A, or PRLR Cyto42 L283A L284A L292A L293A (a.k.a. 4LA) in a tetracycline-controlled fashion (using e.g., the Jump-In™ Cell Engineering Platform, ThermoFisher Scientific, Waltham Mass.) were induced by Doxycyclin (0.7 µg/ml) for 24 hours and treated with CHX (50 µg/ml) for 0 or 4 hours. The results are depicted in the western blot of FIG. 18, which shows a reduction in protein degradation for those constructs lacking Cyto21-42, or the di-leucine repeats. The results support the conclusion that these residues are important for lysosomal targeting.

Additional experiments demonstrated that PRLR turnover, which is mediated by its cytoplasmic domain, is the driving force directing HER2 to lysosomal degradation, when both receptors are bridged using HER2(T)xPRLR bispecific antibodies. (HER2(T) represents a trastuzumab arm.) The kinetic binding parameters of the bispecific antibody and its parent monospecific antibodies were first assessed. The bispecific antibody showed similar binding kinetics to the extracellular domains of both HER2 and PRLR as its parental antibodies (Table 6).

To demonstrate that the cytoplasmic domain of PRLR is required for HER2(T)xPRLR bsAb-mediated degradation of endogenous HER2, T-REx™ HEK293 cells were engineered to express either a full length PRLR, or a truncated PRLR lacking the entire cytoplasmic domain (lower panel). The proteins were expressed in a tetracycline-controlled fashion using the Jump-In™ Cell Engineering Platform (ThermoFisher Scientific, Waltham Mass.). Cells were induced for 24 hours with 0.7 µg/ml doxycycline followed by incubation with CHX combined with the indicated antibodies (Table 6) for different times, lysed and processed for Western Blot.

TABLE 6

| Antibody | Protein | Kinetic Binding Parameters | | | |
|---|---|---|---|---|---|
| | | $k_a$ (M$^{-1}$s$^{-1}$) | $k_d$ (s-1) | $K_D$ (M) | $T_{1/2}$ (h) |
| HER2(T) antibody | hHER2 · mmh | $2.54 \times 10^5$ | $1.01 \times 10^{-3}$ | $3.98 \times 10^{-9}$ | 11 |
| PRLR antibody | hPRLR · mmh | $1.20 \times 10^6$ | $4.15 \times 10^{-3}$ | $3.45 \times 10^{-9}$ | 3 |
| HER2(T) × PRLR bispecific | hHER2 · mmh | $1.70 \times 10^6$ | $2.86 \times 10^{-4}$ | $1.69 \times 10^{-9}$ | 40 |
| | hPRLR · mmh | $5.51 \times 10^6$ | $3.36 \times 10^{-4}$ | $6.10 \times 10^{-10}$ | 34 |

Figure 19:
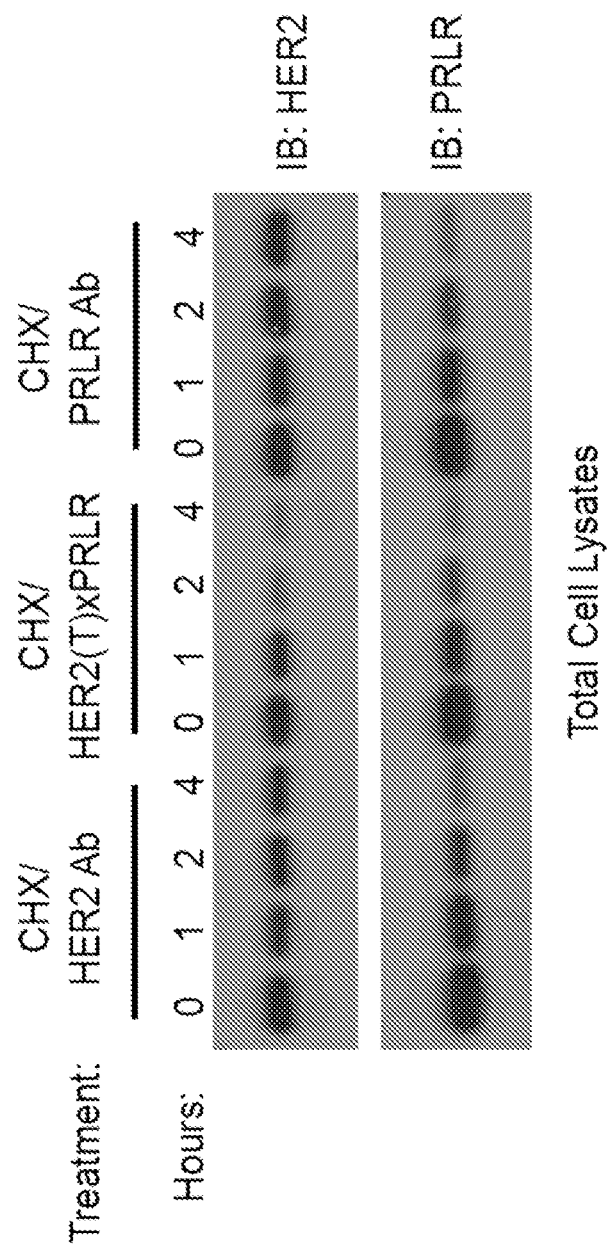
FIG. 19 depicts a western blot of whole cell lysates of HEK 293 cells induced to express full length PRLR at 0 hours, 1 hour, 2 hours, and 4 hours post CHX treatment. The upper panel is stained for HER2, and the lower panel is stained for PRLR.
Figure 20:
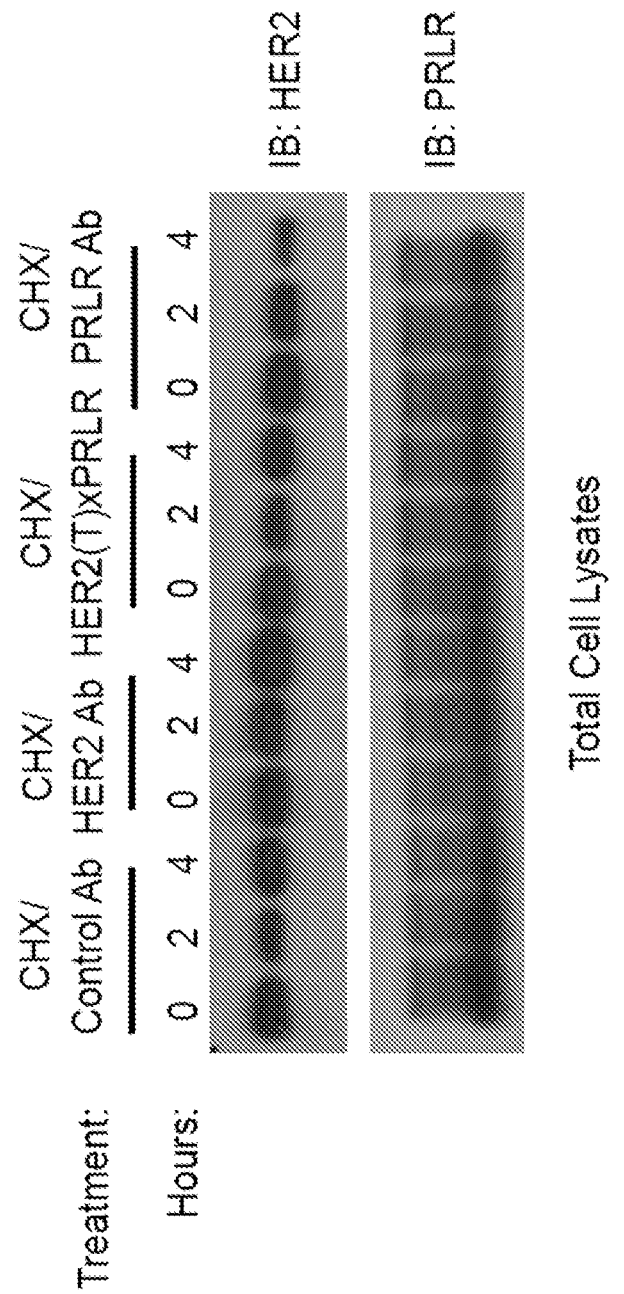
FIG. 20 depicts a western blot of whole cell lysates of HEK 293 cells induced to express the cytoplasmic truncation form of PRLR at 0 hours, 2 hours, and 4 hours post CHX treatment. The upper panel is stained for HER2, and the lower panel is stained for PRLR.

FIG. 19 depicts the western blot of lysates from cells expressing the full length PRLR construct. Note that the HER2(T) × PRLR bispecific antibody effectively targets HER2 to the lysosome, whereas the anti-HER2(T) antibody does not, demonstrating the effectiveness of PRLR as an internalization effector for low expressing HER2. FIG. 20 depicts the western blot of lysates from cells expressing the cytoplasmic truncated PRLR construct. Here, no degradation of PRLR or HER2 was noted under any treatment, thus demonstrating the necessity of the cytoplasmic domain of PRLR to target that receptor and its molecular cargo to the lysosome.

Figure 21:
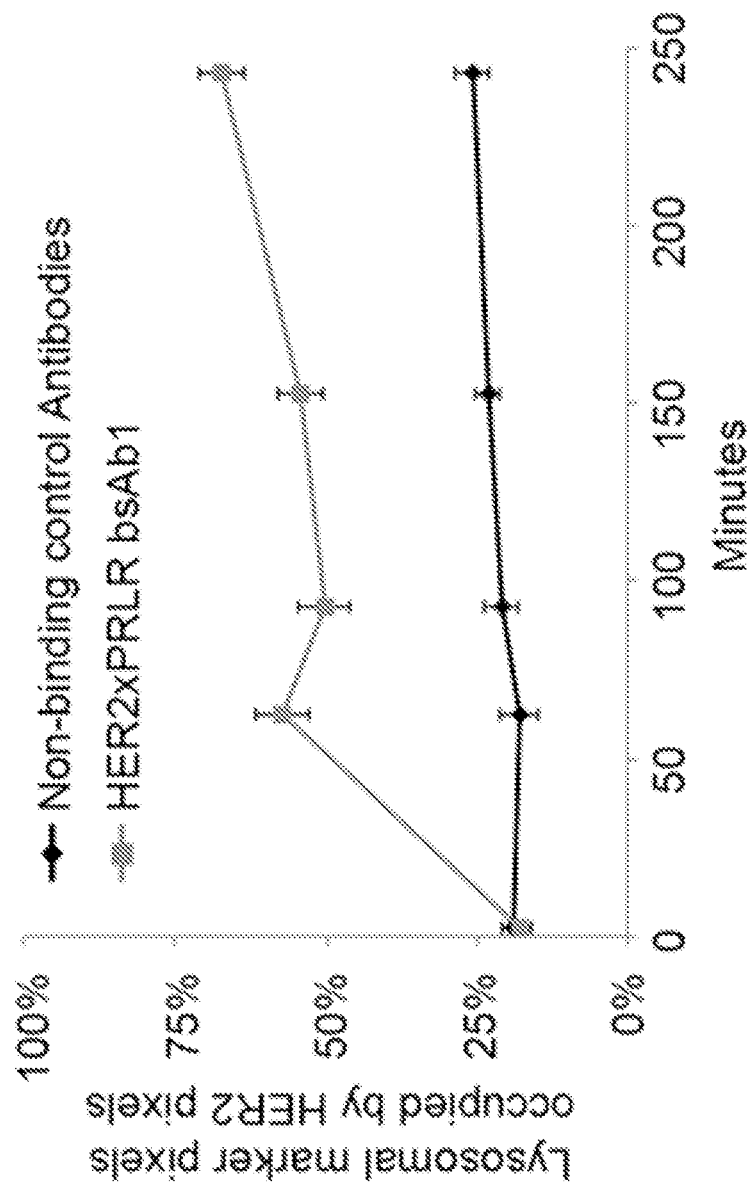
FIG. 21 depicts co-localization of HER2 with lysosomes in T47D cells treated with the HER2 x PRLR bispecific antibody. Percent lysosomes associated with the HER2 receptor is shown over time. Squares represent cells treated with the HER2 x PRLR bispecific antibody and triangles represent cells treated with non-binding control antibodies.

The HER2xPRLR bispecific antibody induced lysosomal trafficking of HER2, enhanced HER2-ADC-induced cell cycle arrest, and promoted cell killing in T47D cells. To determine lysosome targeting, the T47D cells were treated with either non-binding control antibodies or the HER2 x PRLR bispecific antibody and subjected to the Ice-to-37° C. endocytosis assay. Lysosomes and HER2 were stained and the percentage of lysosomal marker pixels occupied by HER2 pixels was determined. The results are depicted in FIG. 21, which shows the more than 50% to 60% of the HER2 was targeted to the lysosome by the HER2 x PRLR bispecific antibody within 60 minutes of warming, compared to fewer than 25% in the controls.

Figure 22:
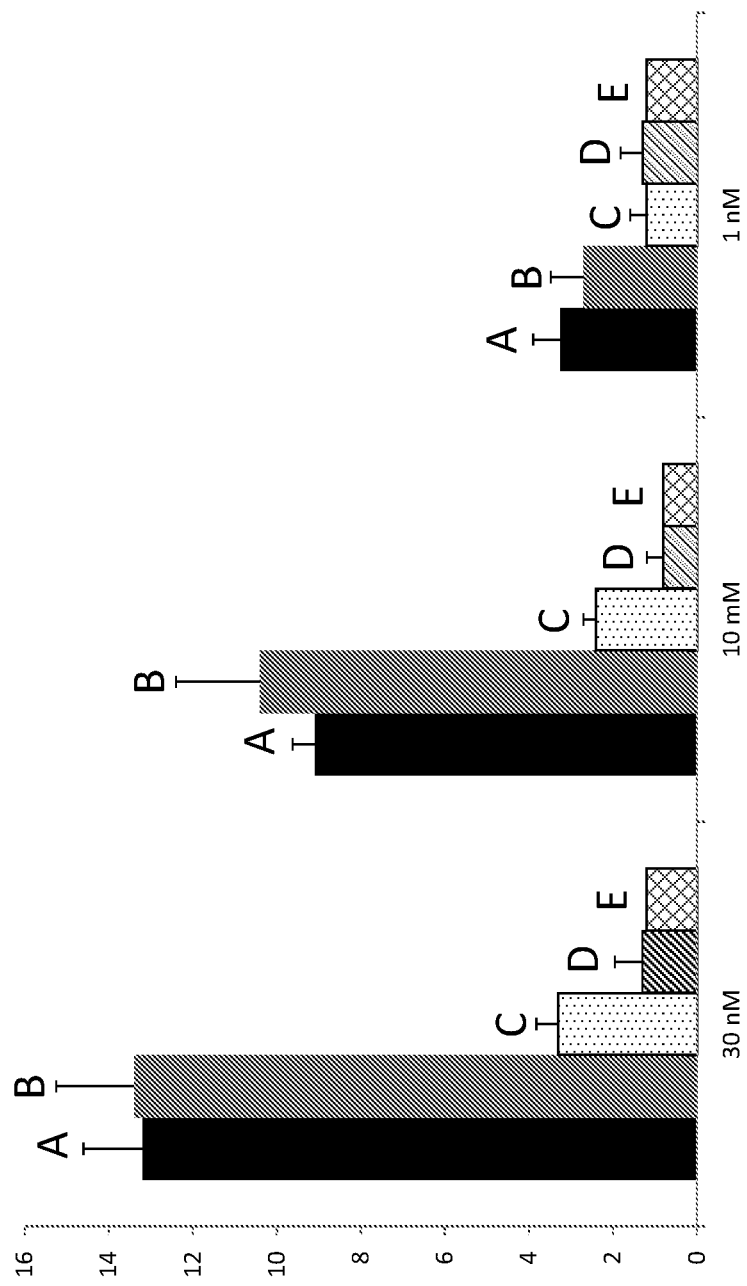
FIG. 22 is a histogram depicting the percentage of cell cycle arrested T47D/HER2 cells (Y-axis) treated with 1 nM, 10 nm, or 30 nM of PRLR-ADC (A), HER2-ADC plus HER2 x PRLR bispecific antibody (B), HER2-ADC alone (C), non-binding control ADC (D), or no treatment (E).

To determine that the HER2 x PRLR bispecific antibody enhanced HER2-DM1-mediated cell cycle arrest, T47D cells expressing HER2 were treated with 1 nM, 10 nm, or 30 nM of PRLR-ADC (A), HER2-ADC plus HER2 x PRLR bispecific antibody (B), HER2-ADC alone (C), non-binding control ADC (D), or no treatment (E). The percentage of early mitotic cells was determined by staining with anti-phospho-Histone (Ser10) antibody, an indicator of cell cycle arrest. The results are depicted in FIG. 22, which shows HER2-ADC plus HER2 x PRLR bispecific antibody (B) arresting cells more effectively than HER2-ADC alone (C).

Figure 23:
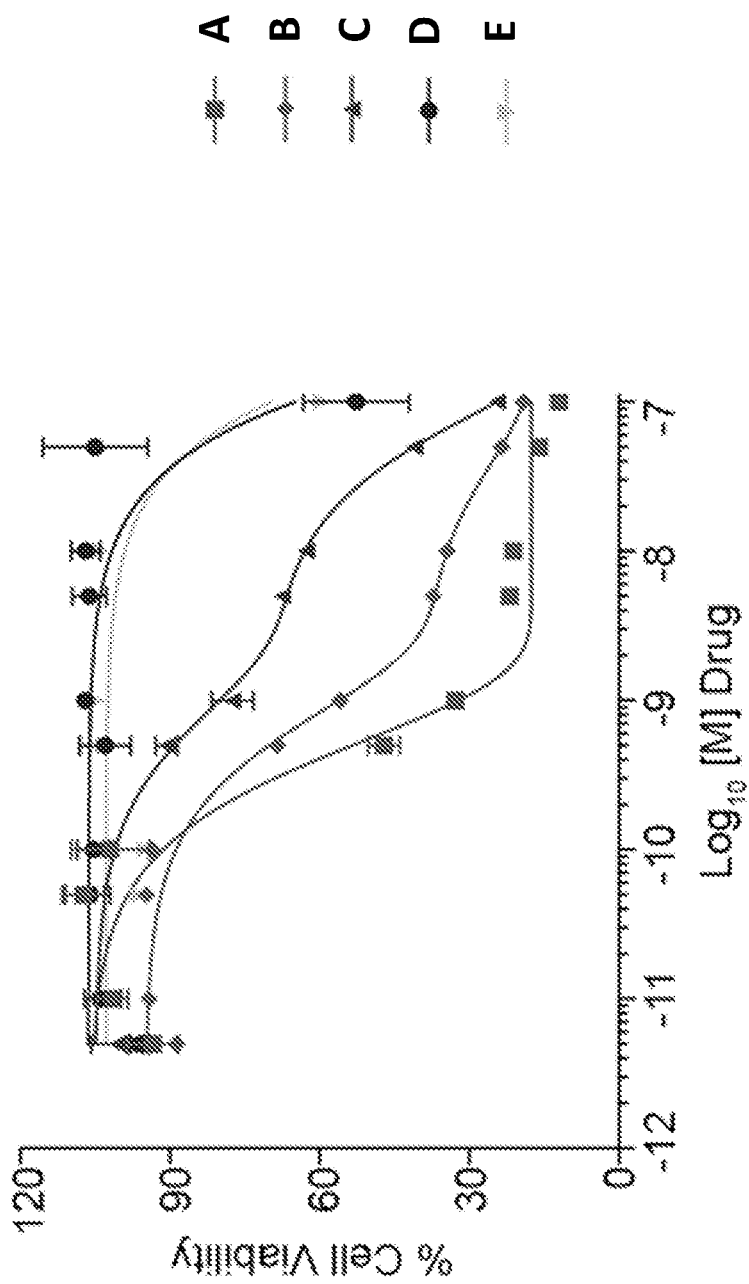
FIG. 23 is a dot blot depicting percentage of viable T47D cells expressing HER2 versus increasing amount of drug: PRLR-ADC (A; squares), HER2-ADC plus HER2 x PRLR bispecific antibody (B; diamonds), HER2-ADC alone (C; up triangles), non-binding control ADC (D; circles), or non-binding control ADC plus HER2 x PRLR bispecific antibody (E; down triangles).
Figure 24:
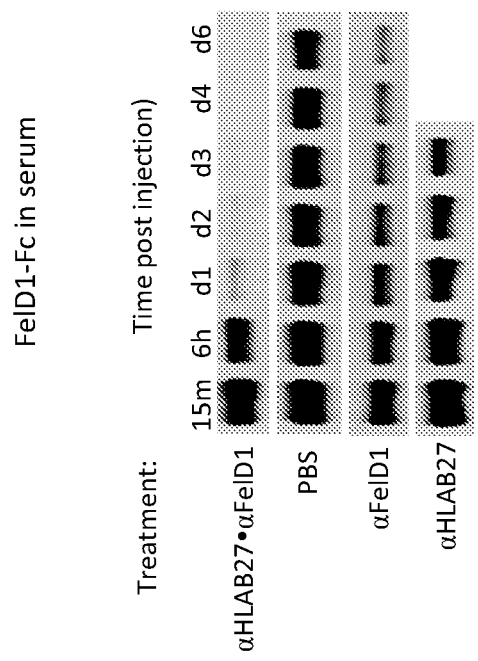
FIG. 24 shows a western blot panel of mouse serum probed with anti-FelD1 antibody at various times (15 minutes, 6 hours, 1 day, 2 days, 3 days, 4 days and 6 days) post-treatment with an anti-HLAB x anti-FelD1 bispecific antibody, phosphate buffered saline, anti-FelD1 bivalent monospecific antibody, and anti-HLAB bivalent monospecific antibody.
Figure 25:
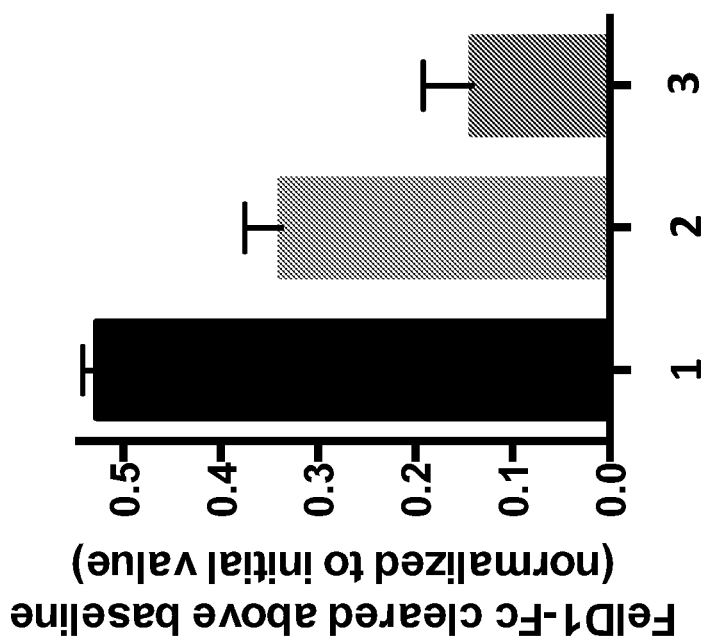
FIG. 25 shows a histogram depicting the proportion of FelD1-Fc cleared from mouse serum above baseline levels and normalized to the initial value (Y-axis). Item 1 depicts treatment with anti-HLAB x anti-FelD1 bispecific antibody; item 2 depicts treatment with anti-FelD1 bivalent monospecific antibody; and item 3 depicts treatment with anti-HLAB bivalent monospecific antibody (X-axis).

To determine that the HER2 x PRLR bispecific antibody enhanced HER2-DM1-mediated cell killing, T47D cells expressing HER2 were treated with drug as indicated in FIG. 23: PRLR-ADC (A), HER2-ADC plus HER2 x PRLR bispecific antibody (B), HER2-ADC alone (C), non-binding control ADC (D), or non-binding control ADC plus HER2 x PRLR bispecific antibody (E). FIG. 23 depicts the results and shows that the HER2 x PRLR bispecific antibody significantly reduced the IC50 for HER2-ADC.

Example 9. High Turnover Rate and Degradation of Target Using hMHC-1 Internalizer High turnover proteins were used to degrade soluble and transmembrane targets. Multispecific antigen-binding proteins (e.g., bispecific antibodies) were designed to link the target molecule with "destroyer" proteins (i) known to be rapidly turned over, (ii) demonstrating high target mediated clearance of bivalent antibodies, and (iii) known to traffic to or from the lysosome. For ease of design and manufacturing, bispecific antibodies were made containing a common light chain, a heavy chain directed to the "destroyer" protein, and a heavy chain directed to the target. One of the heavy chains contained the H95R modification.

In this example, the destroyer molecule selected was major histocompatibility complex I MHC-1, more specifically the class I, B isoform (a.k.a. HLA-B). Tight binding monoclonal antibodies to HLA are rapidly cleared, which is a hallmark of a "destroyer" molecule. As an exemplar soluble target molecule, the allergen FelD1 was selected as the target molecule. FelD1 is a tetrameric glycoprotein comprising two disulfide linked heterodimers. Two forms of soluble FelD1 were constructed and tested, a FelD1-myc-myc-his fusion protein (FelD1-mmh) and a FelD1-Fc fusion protein.

In one set of experiments, FelD1-mmh was labeled with Alexa 488 to aid in tracking the internalization of the target. A bispecific antibody comprising an HLA-B-specific arm (binds destroyer) and a FelD1-specific arm (binds target) (α-HLAB27·α-FelD1) was used as the multispecific antigen-binding protein. C1Rneo B-lymphoblastoid cells expressing HLA-B were incubated with 10 µg/ml FelD1-mmh-Alexa 488, and 10 µg/ml α-HLAB27·α-FelD1. The cells were incubated overnight to allow time for internalization of the FelD1 target protein. The cells were then stained with anti-Alexa488 antibody (Alexa-Fluor-488-Antibody-Polyclonal/A-11094, Thermo Fisher Scientific, Waltham, Mass.)), which quenches the fluorescence of Alexa488. The anti-Alexa488 antibody will not quench labeled target that has been internalized, therefore internalized target can be distinguished from target that is associated with the surface of the cell. Here, fluorescence was quantified by FACs.

Figure 10:
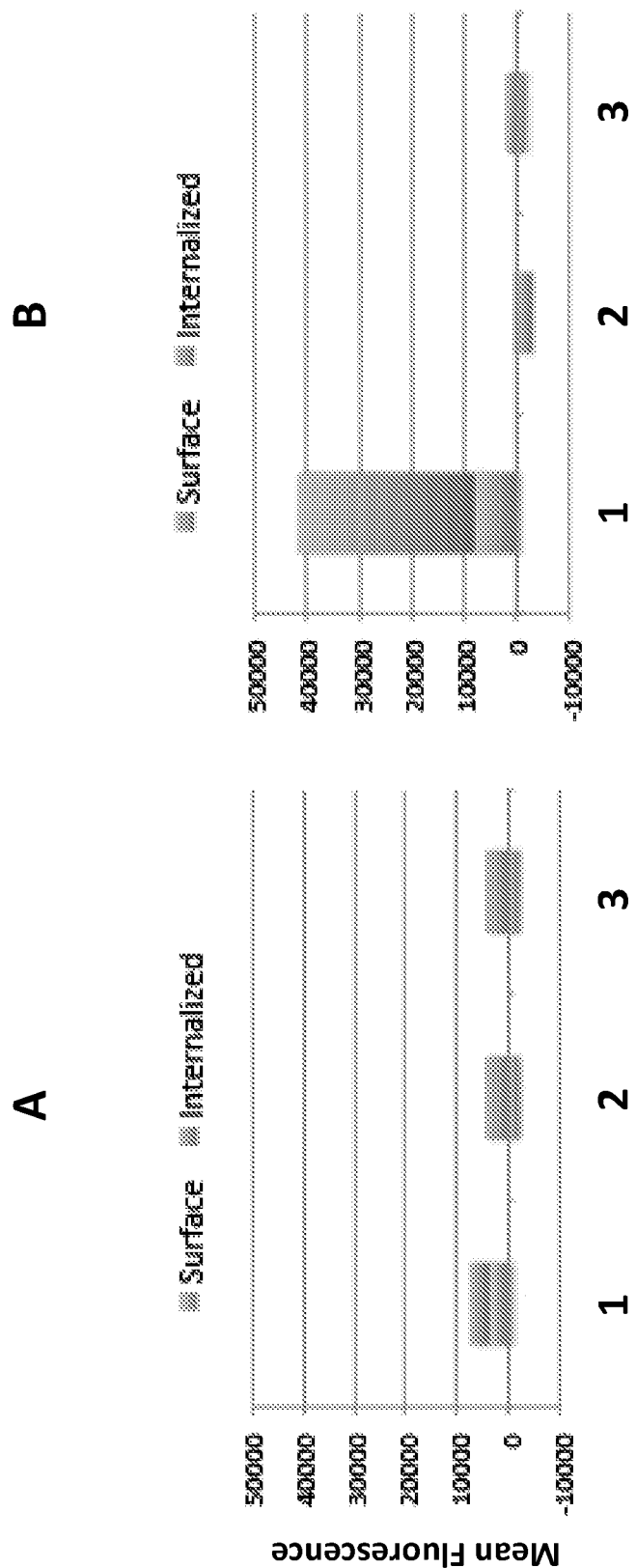
FIG. 10 shows the mean fluorescence in arbitrary units from Alexa488 labeled FelD1-mycv-myc-his. Blue histograms depict cell surface label. Red histograms depict internalized label. Group 1 on the X-axis represents cells treated with anti-HLA-B x anti-FelD1 bispecific antibody; group 2 represents cells treated with anti-HLA-B parental bivalent monospecific antibody; group 3 represents treatment with IgG isotype controls. Panel A shows binding and internalization of FelD1-mmh-488 by C1Rneo B-lymphoblastoid cells that do not express MHC1. Panel B shows binding and internalization of FelD1-mmh-488 by C1Rneo B-lymphoblastoid cells that express MHC1.

FIG. 10 depicts the mean fluorescence (arbitrary units quantified by FACS) of surface-bound target and internalized target, for both MHC1 negative cells, which serve as controls, and MHC1 positive cells. The bispecific antibody used was α-HLAB27·α-FelD1. The parent α-HLAB27·α-HLAB27 bivalent antibody and non-specific IgG isotype were used as controls. For those cells expressing the MHC1 (destroyer), the cells contacted with α-HLAB27·α-FelD1 showed an approximately four-fold increase in internalized target molecule relative to surface-associate target molecule. Essentially no effect was detected for the controls. The results are depicted in FIG. 10 and in Table 7 below.

The α-HLAB27·α-FelD1-mediated clearance of FelD1-Fc from the sera of mice expressing a human HLA-B allele was assessed. Bispecific antibody α-HLAB27·α-FelD1 and controls (PBS, anti-FelD1 bivalent monospecific, and anti-HLAB27 bivalent monospecific) were administered to mice expressing a human HLA-B allele by subcutaneous injection (10 mg/kg). The following day, 1.6 mg/kg of FelD1-Fc was administered by tail vein injection. (A 3:1 antibody:target ratio was used.) Serum samples were obtained from tail bleeds taken at 15 minutes, 6 hours, 1 day, 2 days, 3 days, 4 days, 6 days, and 8 days. FelD1 levels were detected and quantified by Western blotting using anti-FelD1 antibodies. The α-HLAB27·α-FelD1 bispecific treatment demonstrated fast FelD1 clearance with a t½ of <30 hours, similar to the clearance rate of anti-HLAB27 in the absence of FelD1 (i.e., t½ of 33 hours) and more than twice the clearance rate of α-HLAB27·α-FelD1 in the absence of FelD1 (i.e., t½ of 65 hours). The administration of anti-FelD1 did not effect MHC1-mediated clearance, but some moderate clearance was observed, which is attributed to Fc receptors. The results are depicted in FIGS. 11 and 12.

TABLE 7

Mean Fluorescence Units (FelD1-mmh-Alexa288)

| | C1R neo B-Lymphoblastoid Cells | | | |
|---|---|---|---|---|
| | MHC minus cells | | MHC plus cells | |
| Antibody | Surface | Internalized | Surface | Internalized |
| α-HLAB27 · α-FelD1 | <500 | <500 | ~825 | ~3,350 |
| α-HLAB27 · α-FelD1 | <500 | <500 | <500 | <500 |
| Isotype control | <500 | <500 | <500 | <500 |

Example 10. Degradation of Target Using APLP2/PCSK9 System

To assess whether proprotein convertase subtilisin/kexin type 9 (PCSK9) and its cell surface partners (such as LDLR and APLP2; see DeVay et al., "Characterization of proprotein convertase subtilisin/kexin type 9 (PCSK9) trafficking reveals a novel lysosomal targeting mechanism via amyloid precursor-like protein 2 (APLP2)," 288(15) J. Biol. Chem. 10805-18 (Apr. 12, 2013)) can be used as effectors for antibody-mediated target destruction, anti-target-PCSK9 fusion proteins were made. The fusion protein may be regarded as a model for a bispecific antibody that incorporates an anti-PSCK9 or anti-APLP2 binding arm in lieu of the PCSK9 fusion.

For these experiments, hemojuvelin (HJV) was used as a model target in part because the in vivo readout of efficacy, i.e., measuring an increase in serum iron one week after the start of treatment, is easy and reliable. HJV is a co-receptor for bone morphogenic protein 6 (BMP6). Blocking HJV inhibits BMP6 signaling and decreases hepcidin levels, which in turn inhibits the iron transporter ferroportin. Ultimately, blocking HJV increases serum iron. (See Core et al., "Hemojuvelin and bone morphogenetic protein (BMP) signaling in iron homeostasis," 5 Front. Pharmacol. 104 (1-9), May 13, 2014.)

Six antibody::PCSK9 fusion molecules were generated, each comprising either an anti-HJV non-blocking antibody (α-HJV-n) or anti-Myc antibody (α-Myc) in an hIgG1 backbone fused to one of three different PCSK9 (e.g., SEQ ID NO:5) variants via a 3×GGGS linker (SEQ ID NO:6). The first variant is full length PCSK9 without the signal sequence, but including the pro domain (Full Length ["PCSK9FL"]; SEQ ID NO:7). The second is the C-terminal domain only, including some internal linker sequence between the catalytic and c-term domains of PCSK9 (Long C-term ["PCSK9LC"]; SEQ ID NO:8). The third is a short variant of the C-terminal domain that does not include this internal linker sequence (Short C-term ["PCSK9SC"]; SEQ ID NO:9). The C-terminus variants are expected to bind only to APLP2 and not to the LDL receptor.

The antibody::PCSK9 fusions were expressed in and secreted by CHO cells. Plasmids containing both the heavy chain PCSK9 fusion and cognate light chain of the relevant antibody were co-transfected into CHO-K1 cells in 10 cm or 15 cm dishes. The cells were then incubated for 4-5 days to allow production and secretion of antibody::PCSK9, after which the supernatant was harvested and sterilized by filtration through 0.2 micron filters. The CHO cell supernatants containing the fusion proteins were subsequently tested for their ability to internalize soluble HJV protein in vitro.

Soluble HJV tagged with the fluorophore pHrodo was prepared as follows. The HJV ecto-domain (SEQ ID NO:10) fused to the a myc-myc-6xhis (mmh) tag via a GPG linker was expressed in CHO sups and purified. The purified protein was subsequently labeled with pHrodo® (Thermo Fisher Scientific, Waltham) using N-hydroxysulfosuccinimide (NHS) chemistry.

HepG2 cells were incubated with a solution containing 50% antibody::PCSK9-containing CHO supernatant, 50% HepG2 media with 5% Lipoprotein deficient serum and 1 μg/ml pHrodo®-labeled hHJV-mmh. HepG2 cells are a convenient model since they express both LDLR and APLP2, key proteins known to internalize PCSK9. However, for assessing the PCSK9-fusion multispecific antigen-binding proteins, the skilled artisan will appreciate that any cell line (natural, induced, ectopically transformed, and the like) in which PCSK9 is internalized, including through binding partners other than LDLR and APLP2 could potentially be used in this assay. Cells were plated at 1.5×105 cells per mL the day before the assay and incubated at 37° C. Internalization was monitored for 24 hours via imaging on an ImageXpress® high content imager (Molecular Devices, Sunnyvale, Calif.), with the 24 hour time point showing the greatest difference between the constructs and the controls most likely due to pHrodo®-HJV-mmh accumulation in cells throughout the assay. Internalized fluorescence was quantified using MetaXpress® Software (Molecular Devices).

Figure 26:
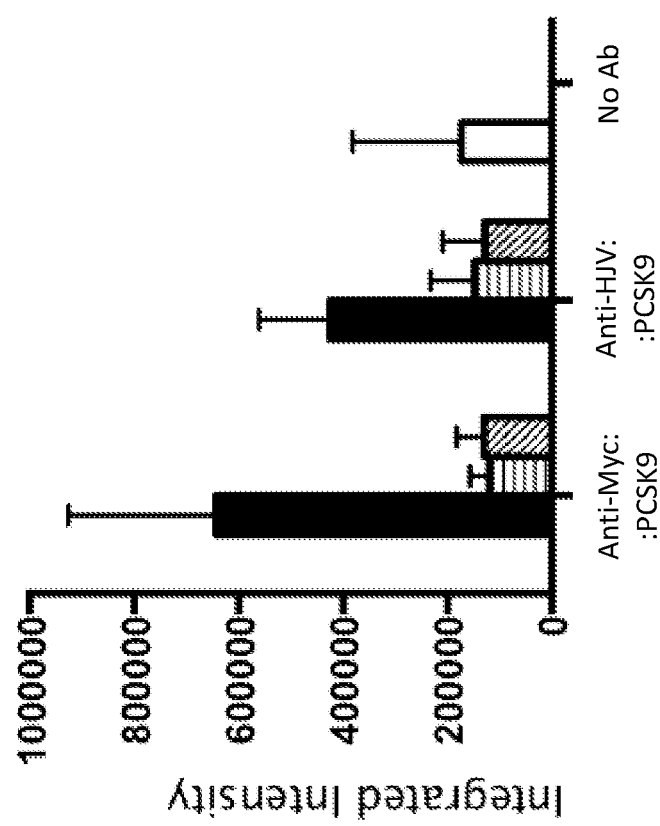
FIG. 26 is a histogram depicting pHrodo®-hHJV-mmh uptake into HEK293 cells. Y-axis depicts integrated intensity (arbitrary units) of pHrodo® signal. At the X-axis, Anti-Myc::PCSK9 depicts the effect on HJV uptake due to no antibody (open bar), α-Myc::PCSK9FL (solid filled bar), α-Myc::PCSK9LC (horizontal line filled bar), and α-Myc::PCSK9SC (stipple filled bar); Anti-HJV::PCSK9 depicts the effect on HJV uptake due to no antibody (open bar), α-HJV-N::PCSK9FL (solid filled bar), α-HJV-N::PCSK9LC (horizontal line filled bar), and α-HJV-N::PCSK9SC (stipple filled bar); and no antibody controls for background uptake.

Incubation with α-HJV-N::PCSK9FL and α-Myc::PCSK9FL increased internalization of the pHrodo®-tagged HJV-mmh protein relative to the no antibody control. Since the pHrodo-tagged HJV-mmh contains two myc-tags, α-Myc::PCSK9FL was expected to act similarly to α-HJV-N::PCSK9FL in this assay. Interestingly, the fusion proteins containing the PCSK9 C-terminal domains (i.e., α-HJV-N::PCSK9LC and α-HJV-N::PCSK9SC), failed to internalize the labeled HJV protein, possibly due to attenuated LDLR binding. Results are depicted in FIG. 26.

Example 11. Degradation of Target In Vivo Using APLP2/PCSK9 System

Figure 27:
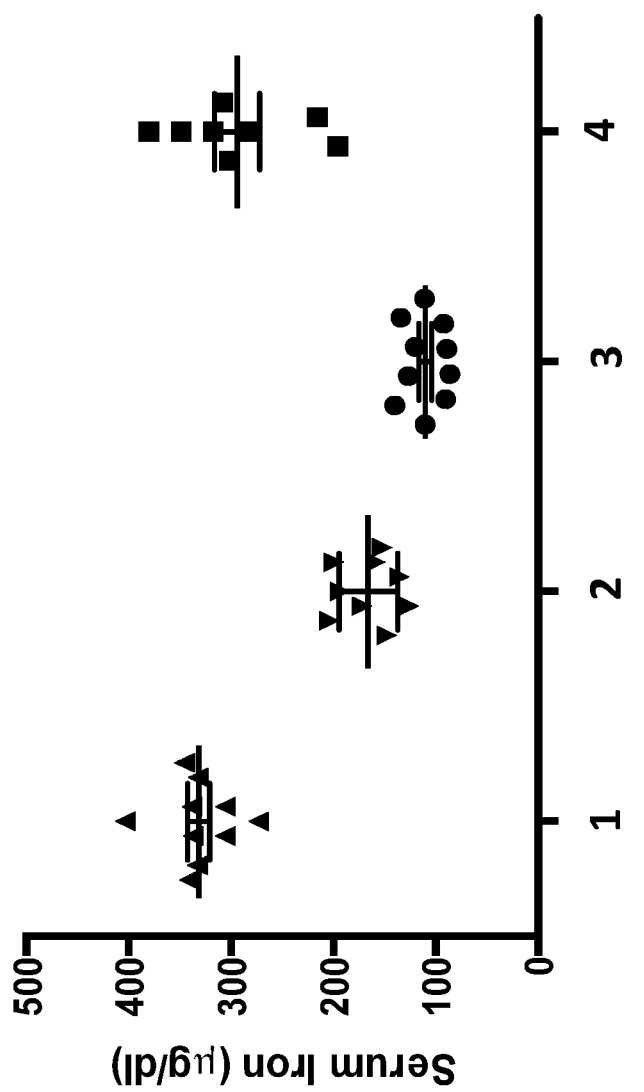
FIG. 27 is a dot blot showing serum iron levels in micrograms per deciliter serum (Y-axis) one week after treatment of hHLAB transgenic mice with anti-HJV-blocking bivalent monospecific antibody (1); anti-Myc::PCSK9 full length fusion protein (2); anti-HJV-non-blocking bivalent monospecific antibody (3); and anti-HJV-non-blocker::PCSK9 full length fusion protein (4).

The parent α-HJV-N bivalent monospecific antibody (which does not block BMP binding to HJV), an α-HJV-B bivalent monospecific antibody (which blocks BMP binding to HJV), the α-HJV-N::PCSK9FL fusion protein, and the α-Myc::PCSK9FL fusion protein were tested for their ability to block HJV signaling in vivo. The molecules were administered to mice via hydrodynamic delivery (HDD). Serum samples were taken one week later. Since endogenous HJV does not have a myc-myc-his tag, the α-Myc::PCSK9FL fusion protein functions as a negative control in vivo. As expected, HDD of the α-HJV-N bivalent multispecific antibody (the positive control) led to a significant increase in serum iron over the negative controls. HDD of α-HJV-N::PCSK9FL (the test molecule), also led to a significant increase in serum iron, of similar magnitude as the blocking antibody, suggesting that this molecule is effective at internalizing and either sequestering or destroying HJV in vivo (FIG. 27).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. A method of forcing programmed cell death protein ligand-1 (PD-L1), expressed on the surface of a breast cancer cell, to degrade in a lysosome, comprising the step of physically linking PD-L1 to prolactin receptor (PRLR) by contacting the breast cancer cell with an antibody that comprises (a) an antigen-binding fragment of an anti-PD-L1 antibody and (b) an antigen-binding fragment of an anti-PRLR antibody,
  wherein the antibody binds to PD-L1 and PRLR on the same breast cancer cell,
  wherein PD-L1 is transported to a lysosome through its physical linkage to PRLR and degraded, and
  wherein the lysosomal degradation of PD-L1 through its physical linkage to PRLR is greater than the lysosomal degradation of PD-L1 not physically linked to PRLR.

2. The method of claim 1, wherein the antibody is a bispecific antibody.

3. The method of claim 1, wherein the breast cancer cell is in vivo.

4. The method of claim 2, wherein the bispecific antibody is an anti-PD-L1 x anti-PRLR bispecific antibody.

5. A method of killing a breast cancer cell that expresses on its surface a PD-L1 molecule and a PRLR destroyer molecule, the method comprising the steps of:
  (i) contacting the breast cancer cell with an anti-PD-L1 bivalent monospecific antibody conjugated to a cytotoxic agent; and
  (ii) physically linking PD-L1 to PRLR on the breast cancer cell of part (i) by contacting the cell with an antibody that comprises (a) an antigen-binding fragment of an anti-PD-L1 antibody and (b) an antigen-binding fragment of an anti-PRLR antibody for simultaneous binding to PD-L1 and PRLR on the same cell, wherein the PD-L1 molecule and the cytotoxic agent are subsequently transported to a lysosome within the breast cancer cell through the physical linkage between the PD-L1 molecule and the PRLR destroyer molecule.

6. The method of claim 5, wherein the cytotoxic agent is a radioisotope, a toxin, or a drug.

7. The method of claim 6, wherein the toxin is a calicheamicin, an auristatin, or a maytansine-based cytotoxin.

8. The method of claim 5, wherein the breast cancer cell is a T47D cell.

9. The method of claim 5, wherein the breast cancer cell is in vivo.

10. The method of claim 5, wherein cell-killing potency of the cytotoxic agent is enhanced by the presence of the antibody.

11. The method of claim 5, wherein the antibody that physically links PD-L1 with PRLR is a bispecific antibody.

12. A method of inhibiting the growth or promoting the regression of a tumor that comprises a breast cancer cell that expresses on its surface both a PD-L1 molecule and a PRLR destroyer molecule, the method comprising killing the breast cancer cell according to the method of claim 5.

13. The method of claim 12, wherein the antibody that physically links PD-L1 with PRLR is an anti-PD-L1 x anti-PRLR bispecific antibody.

14. The method of claim 12, wherein the cytotoxic agent is a maytansinoid-based cytotoxin.

15. A method of killing a breast cancer cell that expresses on its surface a PD-L1 molecule and a PRLR destroyer molecule, the method comprising the step of physically linking PD-L1 to PRLR by contacting the cell with an antibody cytotoxic agent conjugate that comprises (a) an antigen-binding fragment of an anti-PD-L1 antibody, (b) an antigen-binding fragment of an anti-PRLR antibody, and (c) a cytotoxic agent,
wherein the PD-L1 molecule and the cytotoxic agent, through the physical linkage between the PD-L1 molecule and the PRLR destroyer molecule, are subsequently transported to a lysosome within the breast cancer cell.

16. The method of claim 15, wherein the cytotoxic agent is a radioisotope, a toxin, or a drug.

17. The method of claim 16, wherein the toxin is a calicheamicin, an auristatin, or a maytansine-based cytotoxin.

18. The method of claim 15, wherein the breast cancer cell is a T47D cell.

19. The method of claim 15, wherein the breast cancer cell is in vivo.

20. The method of claim 15, wherein cell-killing potency of the cytotoxic agent is enhanced by the presence of the antibody.

21. The method of claim 15, wherein the antibody cytotoxic agent conjugate comprises an anti-PD-L1 x anti-PRLR bispecific antibody.

22. A method of inhibiting the growth or promoting the regression of a tumor that comprises a breast cancer cell that expresses on its surface both a PD-L1 molecule and a PRLR destroyer molecule, the method comprising killing the breast cancer cell according to the method of claim 15.

23. The method of claim 22, wherein the cytotoxic agent is a maytansinoid-based cytotoxin.

24. The method of claim 22, wherein the antibody cytotoxic agent conjugate comprises an anti-PD-L1 x anti-PRLR bispecific antibody.

25. A method of forcing PD-L1, expressed on the surface of a breast cancer cell, to degrade in a lysosome, comprising the step of physically linking PD-L1 to PRLR by contacting the breast cancer cell with an antibody that comprises (a) an antigen-binding fragment of an anti-PD-L1 antibody and (b) an antigen-binding fragment of an anti-PRLR antibody,
wherein the antibody binds to PD-L1 and PRLR on the same breast cancer cell,
wherein PD-L1 is transported to a lysosome through its physical linkage to PRLR and degraded, and
wherein,
in the presence of an inhibitor of protein synthesis, at least 40% of PD-L1 in the breast cancer cell is degraded after about 2 hours of contacting the breast cancer cell with the antibody, and/or
in the presence of an inhibitor of protein synthesis, at least 80% of PD-L1 in the breast cancer cell is degraded after about 4 hours of contacting the breast cancer cell with the antibody.

26. The method of claim 25, wherein the antibody is a bispecific antibody.

27. The method of claim 26, wherein the bispecific antibody is an anti-PD-L1 x anti-PRLR bispecific antibody.

28. A method of forcing PD-L1, expressed on the surface of a breast cancer cell, to degrade in a lysosome, comprising the step of physically linking PD-L1 to PRLR by contacting the breast cancer cell with an antibody that comprises (a) an antigen-binding fragment of an anti-PD-L1 antibody and (b) an antigen-binding fragment of an anti-PRLR antibody,
wherein the antibody binds to PD-L1 and PRLR on the same breast cancer cell,
wherein PD-L1 is transported to a lysosome through its physical linkage to PRLR and degraded, and
wherein degradation of PD-L1 is dependent on the dose of the antibody.

29. The method of claim 28, wherein the antibody is a bispecific antibody.

30. The method of claim 29, wherein the bispecific antibody is an anti-PD-L1 x anti-PRLR bispecific antibody.

* * * * *